United States Patent [19]

Mills

[11] Patent Number: 5,773,592
[45] Date of Patent: Jun. 30, 1998

[54] PRO DRUGS FOR SELECTIVE DRUG DELIVERY

[76] Inventor: Randell Lee Mills, R.D. #2, Cochranville, Pa. 19330

[21] Appl. No.: 450,672

[22] Filed: May 30, 1995

Related U.S. Application Data

[63] Continuation of Ser. No. 446,439, Dec. 4, 1989, Pat. No. 5,428,163, which is a continuation-in-part of Ser. No. 948, 326, Dec. 31, 1986, abandoned, and a continuation-in-part of Ser. No. 175,970, Mar. 31, 1988, abandoned.

[51] Int. Cl.[6] .................. C07C 245/00; A01N 33/26; C12Q 1/70
[52] U.S. Cl. .................. 534/573; 544/232; 435/5; 435/6; 935/78
[58] Field of Search .................. 544/232; 534/573; 514/150, 151; 435/605, 606; 935/78

[56] References Cited

U.S. PATENT DOCUMENTS

| | | | |
|---|---|---|---|
| 2,829,148 | 4/1958 | Chalkley | 260/391 |
| 2,839,542 | 6/1958 | Chalkley | 260/391 |
| 2,839,543 | 6/1958 | Chalkley | 260/394 |
| 2,855,303 | 10/1958 | Chalkley | 96/90 |
| 2,936,235 | 5/1960 | Chalkley | 96/85 |
| 3,798,131 | 3/1974 | Rounds et al. | 435/6 |
| 4,399,131 | 8/1983 | Durckheimer | 424/246 |
| 4,599,303 | 7/1986 | Yabusaki et al. | 935/78 X |
| 4,626,501 | 12/1986 | Landes | 435/6 |
| 4,656,127 | 4/1987 | Mundy | 435/6 |
| 4,683,194 | 7/1987 | Saiki et al. | 435/6 |
| 4,716,106 | 12/1987 | Chiswell | 435/5 X |
| 5,428,163 | 6/1995 | Mills | 544/732 |

FOREIGN PATENT DOCUMENTS

078636  6/1985  European Pat. Off. .

OTHER PUBLICATIONS

Abuin, E., et al, Photochemistry and Photobiology, 30, 59–62 (1979).
Adam, W., et al, Photochemistry and Photobiology, 30, 45–48 (1979).
Adams, R., et al, "The Use of Oxalyl Chloride and Bromide for Producing Acid Chlorides, Acid Bromides or Acid Anhydrides", 599–611 (1920).
Agarwal, R.P., et al, Biochem. Pharmacol., 24, 693–701 (1975).
Agarwal, R.P., et al, Biochem. Pharmacol., 26, 359–367 (1977).
Allen, R.C., Chemical and Biological Generation of Excited States, 309–345 (1968).
Alston, T.A., et al, Biochemistry, 26, 4082–4085 (1987).
Ando, W., et al, Photochemistry and Photobiology, 30, 81–87 (1979).
Arakawa, H., et al, Chem. Pharm. Bull., 30(8), 3036–3039 (1982).
Asano, T., et al, Mol. Pharm., 13, 400–406 (1977).
Baker, B.R., "Design of Active–Site–Directed Irreversible Enzyme Inhibitors", 9 (1975).

Baker, B.R., et al, J. Med. Chem., 10, 682–685, 1101–1105, 1134–1138 (1967).
Baker, B.R., et al, J. Med. Chem., 11, 666–672 (1968).
Baldessarini, R.J., et al, Biochem. Pharmacology, 22, 247–256 (1973).
Baldwin, J.J., et al, J. Med. Chem., 18, 895–900 (1975).
Beard, N.A.., et al, Br. J. Pharmac., 54, 65–74 (1975).
Bechara, E.J.H., et al, Photochemistry and Photobiology, 30, 101–110 (1979).
Becker, Y., Pharmac. Ther., 10, 119–159 (1980).
Berger, A.W., et al, Photochemistry and Photobiology, 4, 1123–1127 (1965).
Bergstrand, H., et al, Molecular Pharmacology, 13, 38–43 (1977).
Berridge, M.J., Ann. Rev. Biochem., 56, 159–193 (1987).
Bertelli, A., et al, Experientia, 32, 361–362 (1976).
Bloxham, D.P., Biochem. J., 147, 531–539 (1975).
Bogan, D.J., et al, "Formation and Chemiluminescent Decomposition of Dioxetanes in the Gas Phase", 3–15 (1979).
Borchardt, R.T., et al, J. Medicinal Chem., 18(3), 300–303 (1975).
Bowen, E.J., et al, ed., "Luminescence in Chemistry", 183–190 (1968).
Brady, R.O., Biochim. Biophys. Acta, 70, 467–468 (1963).
Brasen, W.R., et al, Organic Syntheses, 585–589 (1952).
Bricker, L.A., et al, J. Biological Chem., 247(15), 4914–4915 (1972).
Brodbeck, U., ed., "Enzyme Inhibitors", 61–74, 223–244 (1980).
Bryan, L.E., et al, Antimicrob. Agents Chemother., 9(6), 928–938 (1976).
Burghuber, O.C., et al, Am. Rev. Respir. Dis., 131, 778–785 (1985).
Burr, J.G., "Chemi–and Bioluminescence", Marcel Dekker, Inc., N.Y., N.Y., 245–320 (1985).
Buu, N.T., et al, Br. J. Pharmac., 52, 401–406 (1974).
Carlin, S.C., et al, Mol. Pharm., 10, 194–203 (1974).
Catignani, G.L., et al, Life Sciences, 16, 1915–1922 (1975).
Chen, F.W.K., et al, Prostaglandins, 13, 115–125 (1977).
Chignard, M., et al, Prostaglandins, 14, 222–241 (1977).
Chiou, C.Y., et al, Br. J. Pharmac., 53, 279–285 (1975).
Coleman, J.E., J. Biol. Chem., 243(17), 4574–4587 (1968).
Collins, K.D., et al, J. Biol. Chem., 246(21), 6599–6605 (1971).
Collins, K.D., et al, J. Biol. Chem., 249(1), 136–142 (1974).
Counsell, R.E., et al, J. Medicinal Chem., 13(6), 1040–1042 (1970).

(List continued on next page.)

*Primary Examiner*—Johann Richter
*Attorney, Agent, or Firm*—Lahive & Cockfield, LLP; Giulio A. DeConti, Jr; Mark D. Russett

[57] ABSTRACT

A broad class of pharmaceutical agents which react directly with electron carriers or with reactive species produced by electron transport to release a pharmacologically active molecule to effect a therapeutic functional change in the organism by a receptor or nonrecepter mediated action.

26 Claims, No Drawings

OTHER PUBLICATIONS

Coward, J.K., "Drug Action and Design: Mechanism–Based Enzyme Inhibitors", 13=27 (1979).
Cushman, D.W., et al, Biochimica et Biophysica Acta, 424, 449–459 (1976).
Dalton, C., et al, Prostaglandins, 7, 319–327 (1974).
D'Amato, R.F., et al, "Rapid Manual and Mechanized/Automated Methods for the Detection and Identification of Bacteria and Yeasts", 52–65 (1976).
Dawes, E.A., Microbial Energetics, 81–93 (1974).
DeClercq, E., et al, Life Sciences, 17, 187–194 (1975).
Deibel, Jr., M.R., et al, Biochemical Medicine, 25, 288–297 (1981).
Demain, A.L., Biochem. Soc. Symp., 48, 117–132 (1983).
Diliberto, Jr., E.J., et al, Biochemical Pharmacology, 22, 2961–1972 (1973).
D'Iorio, A., et al, Canadian J. of Biochemistry and Physiology, 41, 1779–1784 (1963).
Downing, D.T., et al, Biochem. Biophys. Research Comm., 40, 218–223 (1970).
Dreyer, J.F., "Self–Attenuating Ophthalmic Filter", Report WADD–TR–60–632, Feb. 1961, AD 322820.
Dreyer, J.F., et al, "Investigation of Materials and Systems for Protection Against Flash Blindness Effects of Nuclear Detonations," Report 68–38–CM, AD 688692 (1982).
Dreyer, J.F., Polacoat Inc., Tech. Report SEG–TR–65–50, 1–40, Oct. 1965.
Dreyer, J.F., Polacoat Inc., WADD Tech. Report 60–827, Contract AF 33(616)–6715, 1–20, Feb. 1961.
Dreyer, J.F., Reprint from J. Phys. and Colloid Chem., 52(5), 809–810 (1948).
Dreyer, J.F., unpublished paper presented at the Vth Intern'l Liquid Crystal Conf., in Stockholm, Sweden, Jun. 20, 1974.
Duggan, D.E., et al, J. Med. Chem., 18(9), 900–905 (1975).
Dulin, W.E., et al, Proc. Society for Exper. Biology and Medicine, 118, 499–501 (1965).
Dulin, W.E., et al, Proc. Society for Exper. Biology and Medicine, 121, 777–779 (1966).
Edwards, J.O., et al, "On the Formation and Reactivity of Dioxirane Intermediates in the Reaction of Peroxoanions with Organic Substrates", 63–70 (1979).
Ellenbogen, L., et al, Biochem. Pharm., 18, 683–685 (1969).
Ellenbogen, L., et al, Biochem. Pharm., 22, 939–947 (1973).
ElMasry, A.H., et al, J. Medicinal Chem., 18(1), 16–20 (1975).
Evans, D.P., et al, Br. J. Pharmac., 53, 409–418 (1975).
Ewatz, L., et al, Analytical Biochemistry, 71, 564–570 (1976).
Falcon, M.G., et al, J. Gen. Virol., 36, 199–202 (1977).
Fall, R.R., et al, J. Biol. Chem., 246(22), 6913–6928 (1971).
Ferone, R., J. Biol. Chem., 245(4), 850–854 (1970).
Ferraccioli, G., et al, J. Rheumatol., 11(3), 330–332 (1984).
Fimognari, G.M., et al, Biochemistry, 4, 2086–2090 (1965).
Forster, T., "Comparative Effects of Radiation", John Wiley & Sons, Inc., N.Y., N.Y., 300–325 (1980).
Free, C.A., et al, Biochem. Pharm., 20, 1421–1428 (1971).
Froesch, E.R., et al, Mol. Pharm., 3, 429–441 (1967).
Fuller, R.W., et al, Biochem. Pharmacology, 1981–1983 (1978).
Fuller, R.W., et al, J. Medicinal Chem., 18(3), 304–307 (1975).
Gale, G.R., et al, J. Med. Chem., 13(3), 571–574 (1970).
Gel'man, N.S., et al, Respiration and Phosphorylation of Bacteria, Plenum Press, N.Y., N.Y., 140–159 (1967).
Glamkowski, E.J., et al, J. Am. Chem. Soc., 10, 852–855 (1967).
Gorman, R.R., et al, Biochem. Biophys. Research Comm., 79(1), 305–313 (1977).
Gorsuch, J.D., "Studies of the Chemiluminescence of Luminol", MIT Ph.D. Thesis (1969).
Guldberg, H.C., et al, Pharmacological Reviews, 27(2), 135–206 (1975).
Hare, L.E., et al, J. Medicinal Chemistry, 17(1), 1–5 (1974).
Hartman, W.J., et al, J. Biol. Chem., 216, 507–529 (1955).
Hashiguchi, H., et al, Mol. Pharm., 13, 362–367 (1977).
Hashimoto, T., et al, Eur. J. Biochem., 24, 128–139 (1971).
Hidaka, H., Nature, 231, 54–55 (1971).
Hidaka, H., et al, Mol. Pharm., 9, 172–177 (1973).
Hidaka, H., et al, J. Pharm. Exp. Therp., 19(3), 384–392 (1974).
Hillcoat, B.L., et al, J. Biol. Chem., 242(20), 4777–4781 (1967).
Humphrey, S.M., et al, J. Surgical Research, 43, 187–195 (1987).
Huszti, Z., et al, J. Pharm. Exp. Therp., 192, 432–440 (1975).
Inagaki, M., et al, J. Biol. Chem., 260(5), 2922–2925 (1985).
Ito, Y., et al, "Thermal and Photosensitized Decomposition of Dimeric Valerophenone Peroxide Formed by Ozonation of Valerophenone Oxime Ether", 53–57 (1979).
Iverson, L.L., et al, J. Neurochemistry, 18, 1939–1950 (1971).
Iwai, H., J. Biochem., 76, 419–429 (1974).
Iwata, H., et al, Biochem. Pharmacology, 18, 955–957 (1969).
Iwata, H., et al, Biochem. Pharmacology, 22, 1845–1854 (1973).
Johns, D.G., et al, Biochem. Pharmacology, 19, 1528–1533 (1970).
Johnson, G.A., et al, J. Pharm. Exp. Therp., 168, 229–234 (1969).
Johnston, G.A.R., et al, J. Neurochemistry, 18, 1951–1961 (1971).
Johnston, G.A.R., et al, J. Neurochemistry, 26, 1029–1032 (1976).
Jung, J.M., et al, Biochemical and Biophysical Research Comm., 67(1), 301–306 (1975).
Kamiya, I., et al, "Excited Singlet and Triplet Products Generated from Oxidation of the –CO–CH–Containing Molecules", 49–52 (1979).
Kandutsch, A.A., et al, J. Biol. Chem., 248(24), 8408–8417 (1973).
Kandutsch, A.A., et al, J. Biol. Chem., 249(19), 6057–6061 (1974).
Kasha, M., Photochemistry and Photobiology, 30, 185–186 (1979).
Kattlove, H.E., Biochimica et Biophysica Acta, 372, 135–140 (1974).
Kessel, D., et al, Biochem. Pharmacology, 24, 133–137 (1975).
Khwaja, T.A., et al, Biochemistry, 14, 4238–4244 (1975).
Kobayashi, K., et al, Febs Letters, 76(2), 207–210 (1977).
Kollonitsch, J., et al, Nature, 274, 906–908 (1978).
Ku, E.C., et al, Biochem. Pharmacology, 24, 641–643 (1975).
Kulkarni, P.S., et al, Prostaglandins, 12(3), 465–469 (1976).
Kupiecki, F.P., et al, J. Pharm. Exp. Therp., 160(1), 166–170 (1968).

Kypson, J., et al, J. Pharm. Exp. Therp., 199(3), 565–574 (1976).
LaFon, S.W., et al, J. Biol. Chem., 260, 9660–9665 (1985).
Layton, D., et al, Biochemical and Biophysical Research Comm., 59(1), 322–325 (1974).
Legg, K.D., "The Chemiluminescence of Lucigenin", MIT Ph.D. Thesis (1969).
Leinweber, F.J., et al, Mol. Pharm., 6, 146–155 (1970).
Levitt, M., et al, Biochem. Pharmacology, 16, 1313–1321 (1972).
Lienhard, G.E., Science, 180, 149–154 (1973).
Lippman, R.D., Bioluminescence and Chemiluminescence, 373–381 (1982).
Lippmann, W., et al, Biochem. Pharmacology, 18, 2507–2516 (1969).
Lippmann, W., Experientia, 30, 237–239 (1974).
Lippmann, W., et al, Experientia, 29(8), 990–991, 993–995 (1973).
Lorenz, W., et al, Bioch. Pharm., 17, 539–549 (1968).
Lowenstein, J.M., J. Biol. Chem., 246(3), 629–632 (1971).
Lukes, J.J., et al, J. Med. Chem., 18(4), 351–354 (1975).
Lytle, F.E., "Chemiluminescence and Photoluminescence of Ruthenium Chelates", MIT Ph.D. Thesis (1968).
MacNair, R.N., Photochemistry and Photobiology, 6, 779–797 (1967).
Mao, J.C-H., et al, Biochemistry, 4(25), 5475–5479 (1975).
Maragoudakis, M.E., Biochemistry, 9(2), 413–417 (1970).
Maragoudakis, M.E., et al, J. Biol. Chem., 246(2), 348–358 (1971).
Maragoudakis, M.E., J. Biol. Chem., 246(2), 348–358 (1971).
McCapra, F., et al, Chem. Commun., 15, 522–523 (1966).
McCapra, F., et al, Photochemistry and Photobiology, 4, 1111–1121 (1965).
McEwen, Jr., C.M., et al, Biochemistry, 8, 3963–3972 (1969).
Meek, E.S., et al, Nature, 220, 822 (1968).
Meister, A., ed., "Advances in Enzymology", 59–101 (1987).
Meyer, H., ed., "Calcium Antagonists and Cardiovascular Disease", Raven Press, N.Y., N.Y., 165–173 (1984).
Michelot, R.J., et al, Mol. Pharm., 13, 368–373 (1977).
Morawetz, H., Science, 240, 172–176 (1987).
Nagatsu, T., et al, Experientia, 28, 779–780 (1972).
Nagatsu, T., et al, Biochem. Pharmacology, 21, 1945–1953 (1972).
Nagatsu, T., et al, J. Biol. Chem., 239(9), 2910–2917 (1964).
Nair, M.G., et al, J. Med. Chem., 17(12), 1268–1272 (1974).
Nakamura, H., et al, Photochemistry and Photobiology, 30, 27–33 (1979).
Neilands, J.B., ed., "Microbial Iron Metabolism", Academic Press, N.Y., N.Y., 10–19 (1974).
Nikaido, T., et al, Planta Medica, 43, 18–23 (1981).
Nogrady, T., "Medicinal Chemistry, A Biochemical Approach", Oxford University Press, N.Y., N.Y., 193–203, 274–285, 358–361 (1985).
Noyes, W.A., et al, "An Efficient Apparatus for Fractional Distillation Under Diminished Pressure," 2718–2722 (1971).
O'Brien, R.A., ed., "Receptor Binding in Drug Research", Marcel Dekker, Inc., N.Y., N.Y. and Basel, 205–259 (1991).
Olsen, R.W., et al, Mol. Pharm., 11, 558–565 (1975).
Oyama, H., et al, Biochem. Pharmacology, 25, 277–280 (1976).
Panganamala, R.V., et al, Protaglandins, 14(2), 261–271 (1977).
Pereira, J.N., et al, J. Pharm. Exp. Therp., 157(2), 381–387 (1967).
Philbrook, G.E., et al, Photochemistry and Photobiology, 4, 869–876, 1175–1183 (1965).
Polacoat, Inc., "The Dynacell and Focal Plane Concepts of Phototropic Systems Application to Ophthalmic Nuclear Flash–Protective Devices", MRL–TDR–62–46 May 1962.
Polakoski, K.L., et al, J. Biol. Chem., 248(23), 8183–8188 (1973).
Porter, C.C., et al, Biochem. Pharmacology, 20, 183–191 (1971).
"Prostaglandin Synthetase Inhibitors: New Clinical Applications", Alan R. Liss, Inc., N.Y., N.Y., 231–256 (1980).
Rando, R.R., et al, Biochemical and Biophysical Research Comm., 76(4), 1276–1281 (1977).
Rando, R.R., et al, J. Am. Chem. Soc., 98(21), 6762–6764 (1976).
Rauhut, M.M., et al, Photochemistry and Photobiology, 4, 1097–1110 (1965).
Report reprinted from Chemical and Engineering News, Am. Chem. Soc., 26, 1097 (1948).
Robert, A., et al, Life Sciences, 14, 533–538 (1974).
Roberts, E., et al, Biochem. Pharmacology, 23, 2637–2649 (1974).
Roheim, P.S., et al, Biochem. Biophys. Research Comm., 20, 416–421 (1965).
Rokujo, T., et al, Life Sciences, 9, 379–385 (1970).
Rosen, B.P., ed., "Bacterial Transport", Marcel Dekker, Inc., N.Y., N.Y. and Basel, 481–493 (1964).
Saari, W.S., et al, J. Am. Chem. Soc., 10, 1008–1014 (1967).
Sabine, J.R., ed., "3–Hydroxy–3–Methylglutaryl Coenzyme A Reductase", CRC Series in Enzyme Biology, CRC Press, Inc., Boca Raton, FL, 189–208 (1976).
Sarin, P.M., et al, ed., "Inhibitors of DNA and RNA Polymerases" Intern'l Encyclopedia of Pharmacology and Therapeutics, Section 103, Pergamon Press, N.Y., N.Y., p. 41(1989).
Schaap, A.P., et al, J. Am. Chem. Soc., 99(4), 1270–1272 (1977).
Schnebli, H.P., et al, J. of Biological Chem., 242(9), 1997–2004 (1978).
Schnepp, O., et al, J. Am. Chem. Soc., 84, 172–177 (1962).
Schuster, G.B., et al, Bioluminescence and Chemiluminescence, 23–29 (1981).
Schuster, G.B., et al, Photochemistry and Photobiology, 30, 17–26 (1979).
Schwerzmann, K., et al, J. of Cell Biology, 102, 97–103 (1972).
Sheen, M.R., et al, Mol. Pharmacol., 4, 293–299 (1968).
Shimomura, O., et al, Photochemistry and Photobiology, 30, 89–91 (1979).
Simmonds, H.A., et al, The Lancet, Jan. 14, 60–63 (1978).
Simon, J.R., et al, Archives of Biochemistry and Biophysics, 157, 348–355 (1973).
Slawinska, D., et al, Photochemistry and Photobiology, 30, 71–80 (1979).
Smith, D.A., et al, Geriatics, 42(8), 55–62 (1987).
Sourkes, T.L., Arch. Biochem. Biophys., 51, 444–456 (1954).
Spector, T., et al, Biochimica et Biophysica Acta, 445, 509–517 (1976).
Spector, T., et al, J. Biol. Chem., 245(19), 5079–5085 (1970).

Springer, R.H, et al, J. Med. Chem., 19(2), 291–296 (1967).
Suhadolnik, R.J., Progress in Nucleic Acid Research and Molecular Biology, 22, 193–291 (1979).
Symes, A.L., et al, Biochem. Pharmacology, 23, 2045–2056 (1974).
Tateson, J.E., et al, Life Sciences, 18, 153–162 (1976).
Taylor, R.J., et al, Life Sciences, 6, 1463–1466 (1967).
Taylor, R.J., et al, Biochem. Pharmacology, 17, 1779–1788 (1968).
Taylor, R.J., et al, Biochem. Pharmacology, 25, 2479–2484 (1976).
Tipton, K.F., Biochem. J., 128, 913–919 (1972).
Trotta, P.P., et al, Mol. Pharm., 14, 199–209 (1978).
Tuemmler, W.B., et al, J. Am. Chem. Soc., 80, 3772–3775 (1958).
Tunnicliff, G., et al Experientia, 33, 20–22 (1977).
Umezawa, H., Ann. Rev. Microbiol., 36, 75–99 (1982).
Uretsky, N.J., et al, The J. Pharm. and Exp. Therp., 193(1), 73–87 (1975).
Van Der Schoot, J.B., et al, J. Pharm. Exp. Therp., 141, 74–78 (1963).
Van Dyke, K., Bioluminescence and Chemiluminescence, 1, CRC Press, Inc., 1–42 (1985).
Vigdahl, R.L., et al, Biochem. Biophys. Research Comm., 42(6), 1088–1094 (1971).
Walsh, C.T., Ann. Rev. Biochem., 53, 493–535 (1984).
Way, L., et al, Nature, 221, 874–875 (1969).
Weinberg, E.D., reprint from Adv. Microb. Phisiol., 4, 1–44 (1970).
Weinberg, E.D., reprint from Science, 184, 952–956 (1974).
Weinhold, P.A., et al, Biochem. Pharmacology, 18, 677–680 (1969).
Weinstock, M., Life Sciences, 19, 1453–1466 (1976).
White, D.C., et al, The J. Biological Chem., 239(11), 3956–3963 (1964).
White, E.H., et al, Photochemistry and Photobiology, 4, 1129–1155 (1965).
Wilkinson, F., Luminescence in Chemistry, 154–182 (1971).
Windmueller, H.G., et al, J. Biol. Chem., 9, 2246–2254 (1967).
Wittig, G., et al, Organic Syntheses, 40, 66–71 (1962).
Zaklika, K.A., et al, Photochemistry and Photobiology, 30, 35–44 (1979).
"Analysis of Insecticides and Acaricides", Gunther and Blinn, Inter–Science, N.Y., N.Y., 401–404 (1955).
Bernal, S.D., et al, Science, 222 (1983).
Brodbeck, U., ed., "Enzyme Inhibitors", 85–95 (1980).
Bullen, J.J., et al, Immunology, 12, 303 (1967).
Caroline, L., et al, J. Invest. Dermalology, 42, 415 (1964).
Dixon, M., et al, "Enzymes", Academic Press Inc., N.Y., N.Y., 407 (1964).
Fletcher, J., et al, Br. J. Exp. Pathol., 51, 280 (1970).
Gale, E.F., ed., "The Molecular Basis of Antibiotic Action", 258–401 (1981).
Gilman, A.G., et al, ed., "The Pharmacological Basis of Therapeutics", MacMillan Publishing Co., N.Y., N.Y., 668–681 (1980).
Inagaki, M., et al, Biochemistry, 23, 5036 (1984).
Kochan, I., Curr. Top. Microbiol. Immunol., 60, 1 (1973).
Kondo, T., et al, Diabetes Care, 5(3), 218–221 (1982).
Lampidis, T.J., Cancer Research, 43, 716–720 (1983).
Miller, L.L., J. Electroanal. Chem., 117, 267–281 (1981).
Papa, S., Cancer Research, 43, 834–838 (1983).
Polacoat, Inc., "Development of a Means to Provide Protection for Eyes Against the Dazzle Effects of Nuclear Detonations", Quart. Report No. 5 on Contract DA 19–129 qm–1534, Apr. 1961, AD 446865; AD 447113 and 298225 (1984).
Rogers, H.S., Immunology, 12, 285 (1967).
Undenfriend, S., et al, Biochem. Pharmacology, 14, 837–845 (1965).
Vrang, L., et al, Antimicrobial Agents and Chemotherapy, 29, 867–872 (1986).
Wake, A., et al, Jap. J. Med. Sci. Biol., 25, 75 (1972).

PRO DRUGS FOR SELECTIVE DRUG DELIVERY

This application is a continuation of application Ser. No. 07/446,439 filed on Dec. 4, 1989, now U.S. Pat. No. 5,428,163, which in turn is a continuation-in-part of application Ser. No. 06/948,326 filed on Dec. 31, 1986, now abandoned and application Ser. No. 07/175,970 filed Mar. 31, 1998, now abandoned. The contents of all of the aforementioned applications are expressly incorporated by reference.

FIELD OF THE INVENTION

The present invention relates to therapeutic pharmaceutical agents which are activated intracellularly by reaction with cellular electron carriers or free radicals to cause release of a free and active drug molecule.

CROSS REFERENCE TO RELATED APPLICATIONS

BACKGROUND OF THE INVENTION

The effects of the preponderance of drugs result from their interaction with functional macromolecular components of the organism. Such interaction alters the function of the pertinent cellular component and thereby initiates the series of biochemical and physiological changes that are characteristic of the response to the drug. The term receptor denotes the component of the organism with which the chemical agent interacts. There are fundamental corollaries to the statement that the receptor for a drug can be any functional macromolecular component of the organism. One is that a drug is potentially capable of altering the rate at which any bodily function proceeds; a second is that, by virtue of interactions with specific receptors, drugs do not create effects but merely modulate the rates of ongoing functions. A simple pharmacological dictum thus states that a drug cannot impart a new function to a cell. Functional changes due to a drug result from either enhancement or inhibition of the unperturbed rate. Furthermore, a drug that has no direct action can cause a functional change by competition for a binding site with another, active regulatory ligand of the receptor. Drugs are termed agonists when they cause effects as a result of direct alteration of the fundamental properties of the receptor with which they interact. Compounds that are themselves devoid of intrinsic pharmacological activity but cause effects by inhibition of the action of a specific agonist (eg. by competition for agonist binding sites) are designated as antagonists.

At least from a numerical standpoint, the proteins of the cell form the most important class of drug receptors. Obvious examples are the enzymes of crucial metabolic or regulatory pathways (eg., tyrosine hydroxylase; 3-hydroxy-3-methylglutaryl-CoA reductase), but of equal interest are proteins involved in transport processes (eg. $Ca^{2+}$-ATPase; $Na^+$-$K^+$-ATPase) or those that are protein kinases which activate other proteins as a consequence of their binding a secondary messenger such as cAMP. Specific binding properties of other cellular constituents can be exploited. Thus, nucleic acids are important drug receptors, particularly for chemotherapeutic approaches to the control of malignancy, and plant lectins shown remarkable specificity for recognition of specific carbohydrate residues in polysaccharides and glycoproteins. Small ions such as $Ca^{2+}$ which can function as a regulatory ion or $Fe^{2+}$ which can serve as an essential enazmatic cofactor can be exploited as drug receptors. And, drugs can also produce a functional change by a nonreceptor-mediated action. Certain drugs that are structural analogues of normal biological constituents may be incorporated into cellular components and thereby alter their function. This has been termed a "counterfeit incorporation mechanism" and has been implemented with analogues of purines and pyrimidines that can be incorporated into nucleir acids and that have utility in cancer chemotherapy and that have antiviral activity. Also, specific constituents of pathogens can be exploited as receptors. For example, the electron carriers of bacterial can serve as receptors as described in my previous U.S. patent application Ser. No. 948,326, and the replicative enzymes of viruses can be serve as receptors as described below for the virus HIV. Many compounds are known which have receptor or nonreceptor mediated in vitro activity as appears in *Handbook of Enzyme Inhibitors,* Mahendra Kumor Jain, 1982, Wiley Interscience, New York, hereby incorporated by reference. However, only a small percentage produce the desired functional change in vivo or have a high therapeutic ratio because they are toxic in their free form; they are rapidly inactivated or excreted; or, they cannot obtain access to their target receptor or site of action because they are impermeant to cells or biological barriers such as the blood brain barrier due to unfavorable energetics due, for example, to the possession of polar or charge groups; or, they are toxic as a consequence of being nonselective with regards to their access to and action with receptors in one biological environment or compartment relative to another. In these cases, compounds which demonstrate in vitro efficacy are ineffective therapeutics.

SUMMARY OF THE INVENTION

A broad class of pharmaceutical agents is disclosed herein as the Luminide class of pharmaceuicals. Luminide agents are three part or four part molecules where each part is a functionality with a defined purpose. Exemplary Luminides are A-B-C , D-A-B-C, A-D-B-C, and

where A represents a functionality which is activatable by the environment and capable of transferring energy from its own excited state to the B functionality which is an energy acceptor. Upon receiving energy from A, B achieves an excited state which relaxes through the heterolytic cleavage of the covalent bond of B with C where C is a drug moiety which is released into the intracellular compartment where activation of A occured. Released C can act locally or at a distant site. D serves as an electron transfer functionality which gains (loses) electrons from (to) the environment and donates (accepts) electrons to (from) A to activate it so that the energy of excited A is transferred to B with release of C as occurs for the three functionality case.

In both cases, free C is a drug molecule. The released drug molecule effects a therapeutic functional change by a mechanism which comprises receptor mediated mechanisms including reversible or irreversible competitve agonism or antagonism including a suicide substrate or transition state analogue mechanism or a noncompetitive or uncompetitve agonism or antagonism or the action is by a nonreceptor mediated mechanism including a "counterfeit incorporation mechanism".

The chemical and physical properties of the Luminide agents such as permeance and reactivity to different oxidoreductase enzymes, electron carriers, or different free radicals including those of oxygen are exploited to control the environment into which C is released. Permeance of the Luminide agent to the blood brain barrier or cell membranes, or affinity of the Luminide agent to plasma proteins which results in a decreased excretion rate relative to free C, or lack of reactivity of extracellular enzymes with the Luminide agent relative to free C are exemplary mechanism where by Luminides provide for the release of active free C in the proper biological compartment or in the presence of the target receptor so that the desired therapeutic- change is achieved. Thus, Luminides serve as therapeutic drugs. And, the present invention, Luminides, a broad class of pharmaceutical agents comprises antilipidemic drugs, anticholesterol drugs, contraceptive agents, anticoagulants, antiinflamatory agents, immuno-suppressive drugs, antiarrhythmic agents, antineoplastic drugs, antihypertensive drugs, epinephrine blocking agents, cardiac inotropic drugs, antidepressant drugs, diuretics, antifungal agents, antibacterial drugs, anxiolytic agents, sedatives, muscle relaxants, anticonvulsants, agents for the treatment of ulcer disease, agents for the treatment of asthma and hypersensitivity reactions, antithroboembolic agents, agents for the treatment of muscular dystrophy, agents to effect a therapeutic abortion, agents for the treatment of anemia, agents to improve allograft survival, agents for the treatment of disorders of purine metabolism, agents for the treatment of ischemic heart disease, agents for the treatment of opiate withdrawal, agents which activate the effects of secondary messenger inositol triphosphate, agents to block spinal reflexes, and antiviral agents including a drug for the treatment of AIDS.

DETAILED DESCRIPTION OF THE INVENTION

Electron transferring and transporting elements are ubiquitous and are necessary for life. All eukaryotic and prokaryotic organisms depend on electron transferring and transporting elements which include metal containing hemes and nonmetal containing molecules such as flavins to convert the energy stored in the chemical bonds of foodstuffs into a form utilizable for the maintenance of the highly negative entropic state of life. The chemical energy conversion process generally involves a coupled series of electron carriers which is called an electron transport chain.

Free radicals of oxygen are produced during aerobic respiration in mitochondria as electrons are carried by electron carriers of the electron transport chain to the ultimate electron acceptor, oxygen, and superoxide and peroxide, partial reduction products of oxygen, are continuously produced during cytosolic hydroxylation and oxygenation reactions as well as during other reactions which involve enzymatic reduction of oxygen. The cytosol as well as mitochondria of aerobic cells contain high concentrations of the enzyme superoxide dismutase which converts superoxide into hydrogen peroxide and molecular oxygen. Oxygen radicals which include hydrogen peroxide and superoxide are found in greater concentration in the mitochondria relative to the cytosol because reduction of oxygen occurs to a greater extent in the former compartment; however, appreciable concentration are found in both compartments.

Luminides are agents which are permeant to the desired biological compartment which undergo an oxidation reduction reaction with the target cell's electron carriers or react with free radicals produced as a consequence of electron transport and release a drug moiety into the desired compartment in active form to effect a greater therapeutic effect or therapeutic ratio relative to the free C agent as a consequence of altered pharmacokinetics or pharmacodynamics such as a desirable kinetics of release, a resistance to inactivation or excretion, greater solubility, enhanced absorption, a diminished toxicity, or greater access to the cellular or biological compartment which is the site of action of C.

Luminide agents are three or four part molecules where each part is a functionality with a defined purpose. Exemplary Luminides are A-B-C, D-A-B-C, A-D-B-C and

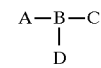

where A represents a functionality which undergoes an oxidation reduction reaction where electrons are transferred directly between A and the target cell's electron carriers or the electrons are transferred indirectly through an electron transfer functionality, D, which is described in more detail below. Alternatively, A represents a functionality which undergoes a reaction with free radicals of oxygen which are produced as a consequence of electron transport. An excited state is produced in A as a consequence of its participation in one of these reactions. Then A undergoes intramolecular energy transfer from its own excited state to the B functionality which is an energy acceptor. Upon receiving energy from A, B achieves an excited state which relaxes through heterolytic cleavage of the covalent bond of B with C where C is a drug moiety which is released into the environment. D serves as an electron transfer functionality which gains (loses) electrons from (to) the environment and donates (accepts) electrons to (from) A to activate it so that the energy of excited A is transferred to B with release of C as occurs for the three functionality case. In both cases, free C is a drug molecule. The released drug molecule effects a therapeutic functional change by a mechanism which comprises receptor mediated mechanisms including reversible and irreversible competitive agonism or antagonism including a molecle known as a suicide substrate or a transition state analogue mechanism or a noncompetitive or uncompetitive agonism or antagonism or the action is by a nonreceptor mediated mechanism including a "counterfeit incorporation-mechanism".

The energy donating funtionality, A, is a molecule which reacts as previously described to form an excited state of high enough energy so that this subsequently transferred energy is of sufficient magnitude to break the covalent bond between the drug functionality, C, and the energy acceptor functionality, B. Chemiluminescent molecules can form highly excited states of the proper magnitude of energy, can undergo oxidation reduction reactions or react with free radicals, and possess a metastable excited state from which intramolecular energy transfer can occur; thus, they can serve as the A functionality. In general, chemiluminescent molecules relevant to this invention can be placed into three categories: 1) molecules undergoing reaction involving peroxides and oxygen free radicals; 2) molecules undergoing reaction involving oxidation or reduction and 3) molecules undergoing both reaction with peroxides and oxygen free radicals followed by an oxidation or reduction reaction. Molecules of the first category include Lophine and its derivatives, acridinium esters and acridans, tetraphenylpyrrole, phthalhydrazides, acyloins, biacridinium salts, vinylcarbonyls, vinylnitriles, tetrakis (dimethylamino) ethylene, acylperoxides, indoles, tetracarbazoles and active oxalates.

Molecules belonging to the second category include ruthenium chelates 2, 6-diaminopyrene, or cation radicals and molecules which follow a Chemically Initiated Electron Exchange Luminescence mechanism such as certain dioxetans and dioxetanones. Dioxene derivatives belong to the third category. They form a dioxetan by reation with superoxide and then produce efficient chemiluminescence by a CIEEL mechanism.

As an example from the first category, the chemiluminescent compound, luminol, has a chemiluminescent maximum in the region 390–400 nm in an aqueous solution. Chemiluminescence is produced by the reaction of luminol with oxygen free radicals where a large fraction of the product molecules are formed in their excited state. The nature of the excited state is electronic, and it has a mean lifetime of the order of $10^{-8}$ seconds which is typically ten thousand times the period of a molecular vibration. Emission involves a quantum mechanically allowed singlet to singlet transition with energy of the order of 75 Kcal/mole. The quantum yield for forming the excited electronic state is 0.5. Because luminol undergoes a chemiluminescent reaction with oxygen radicals, this compound has been used as a molecular probe for these radicals by linkage to a molecule which directs the probe to a cellular compartment. For example, when luminol is attached to carnitine, the probe is transported into mitochondria and the intensity of chemiluminescence produced is proportional to the magnitude of electron transport activity which produces oxygen radicals. The chemiluminescent molecule, lucigenin, is also used as a probe for oxygen free radicals.

As for members of the second category, chemiluminescent molecules which undergo a redox reaction to produce an excited state react directly with electron carriers of the cell or undergo a redox reaction with the electron transfer functionality D.

As for the third category, a D functionality is optional. A chemiluminescent molecule of this category reacts with oxygen free radicals and forms an excited state, and chemiluminescence is produced but properties such as quantum yield or the relative ratio of singlet to triplet excited state can be altered by the transfer of electrons involving for example a D functionality. See Table 1 below for chemiluminescent molecules.

TABLE 1

Representative Chemiluminescent Molecules

| Name | Structure |
|---|---|
| 2,6-diaminopyrene | (structure) |
| Aminophthalhydrazide | (structure) |

TABLE 1-continued

Representative Chemiluminescent Molecules

| Name | Structure |
|---|---|
| Dioxene | (structure) |
| Imidazole derivatives | (structure) |
| Sulfonyloxamides | (structure) |
| Indole derivatives | (structure) |
| Tetrakis(dialkylamino)-ethylene | (structure) |
| 2,5,7,8-tetraoxabicyclo-[4.2.0.] octane | (structure) |
| Dioxetan | (structure) |
| Lucigenin | (structure) |

TABLE 1-continued

Representative Chemiluminescent Molecules

| Name | Structure |
|---|---|
| Lophine | 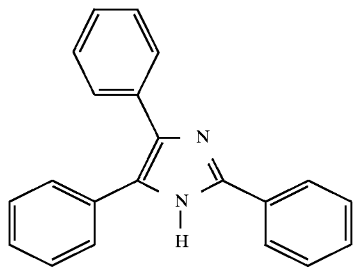 |
| Acridinium esters | 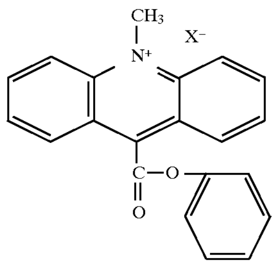 |
| Active oxalate | 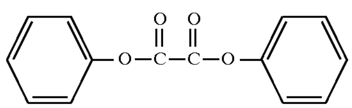 |
| Tris-2,2'-bipyridinedi-chlororuthenium (II) | 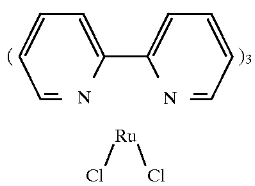 |
| Dioxetanone | 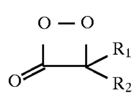 |
| Dipheyl peroxide | 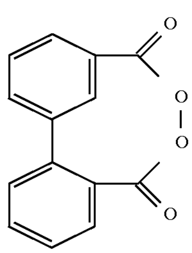 |

Exemplary energy acceptor molecules include those which demonstrate photochromic behavior with electromagnetic radiation and bleaching agents. If the A functionality is chemiluminescent, then the B functionality is such that the photodissociative drug release spectrum of B overlaps the chemiluminescence spectrum of A.

Triarylmethane dyes react with cyanide to form nitriles called leucocyanides which liberate cyanide ion with a quantum yield of approximately one when irradiated with UV light in the wavelength range of 250 to 320 nm.

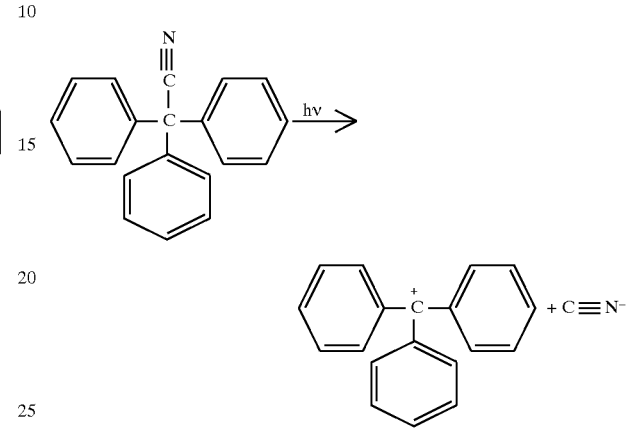

The spectrum of the photorelease reaction of cyanide ion can be extended to longer wavelengths in the case of triarylmethane dyes by substitutions of a naphthylene for an aryl group and also by using cationic polymethine dyes. The latter form nitriles, which are thermally stable, by the reaction of the carbonium ion of the dye with cyanide. The formation of the nitrile causes the colored dye to be bleached as is the case with triarylmethane dyes, and cyanide is released as the dye becomes colored upon absorption of 320–415 nm. Reversible bleaching by an agent and coloration by light is photochromic behavior.

Cationic dyes demonstrate this behavior and include di and triarylmethane dyes, triarylmethane lactones and cyclic ether dyes, cationic indoles, pyronines, phthaleins, oxazines, thiazines, acridines, phenazines, and anthocyanidins, and cationic polymethine dyes and azo and diazopolymethines, styryls, cyanines, hemicyanines, dialkylaminopolyenes, and other related dyes. See Table 2 below for structures for salt isomerism-type photochromic dyes. These photochromic molecules form covalent bonds with a number of agents called bleaching agents because they convert the compounds from colored to colorless form during bond formation. Bleaching agents are diverse and include hydroxide, cyanide, azide, bisulfide, and sulfite compounds, thiocyanate, ferrocyanide, chromate, tetraborate, acetate, nitrite, carbonate, citrate, aluminate, tungstate, molybdate, methoxide, 2-methoxyethoxide, cinnamate, and p-methoxycinnamate salts, and thiols and amines.

TABLE II

Dye Name or Structure; CI Name and Number; Other Names

| | |
|---|---|
| Malachite Green | 42000 |
| Helvetia Green | 42020 |
| Basic Blue 1 | 42025 |
| Brilliant Blue | |
| Setoglaucine | |
| Basic Green 1 | 42040 |
| Brilliant Green | |
| Acid Blue 1 | 42045 |

TABLE II-continued

| | |
|---|---|
| Xylene Blue VS | |
| Patent Blue V | |
| Alphazurine 2G | |
| Acid Blue 3 | 42051 |
| Brilliant Blue V | |
| Patent Blue V | |
| Food Green 3 | 42053 |
| FDC Green 3 | |
| Acid Green 6 | 42075 |
| Light Green SF Bluish | |
| Acid Blue 7 | 42080 |
| Xylene Blue AS | |
| Patent Blue A | |
| Acid Green 3 | 42085 |
| Acid Blue 9 | 42090 |
| Erioglaucine | |
| Acid Green 5 | 42095 |
| Light Green SF Yellowish | |
| Acid Green 9 | 42100 |
| Erioviridene B | |
| Acid Blue 147 | 42135 |
| Xylene Cyanol FF | |
| Basic Red 9 | 42500 |
| Pararosaniline | |
| Basic Violet 14 | 42510 |
| Fuchsin | |
| Magenta | |
| Basic Fuchsin | 42510B |
| Basic Violet 2 | 42520 |
| New Fuchsin | |
| New Magenta | |
| Hoffman Violet | 42530 |
| Iodine Violet | |
| Basic Violet 1 | 42535 |
| Methyl Violet | |
| Basic Violet 13 | 42536 |
| Methyl Violet 6B | |
| Basic Violet 3 | 42555 |
| Crystal Violet | |
| Gentian Violet | |
| Iodine Green | 42556 |
| Basic Blue 8 | 42563 |
| Victoria Blue 4R | |
| Acid Blue 13 | 42571 |
| Fast Acid Violet 10B | |
| Acid Blue 75 | 42576 |
| Eriocyanine A | |
| Methyl Green | 42585 |
| Ethyl Green | 42590 |
| Basic Violet 4 | 42600 |
| Ethyl Violet | |
| Acid Violet 49 | 42640 |
| Wool Violet 5BN | |
| Acid Blue 15 | 42645 |
| Brilliant Milling Blue B | |
| Acid Violet 17 | 42650 |
| Acid Violet 6B | |
| Wool Violet 4BN | |
| Formyl Violet | |
| Acid Violet 5BS Conc. | |
| Acid Violet 19 | 42685 |
| Acid Fuchsin | |
| Red Violet 5R | 42690 |
| Acid Blue 22 | 42755 |
| Aniline Blue | |
| Soluble Blue | |
| Solvent Blue 3 | 42775 |
| Acid Blue 93 | 42780 |
| Methyl Blue | |
| Aurin | 43800 |
| Mordant Blue 3 | 43820 |
| Eriochrome Cyanine R | |
| Acid Green 16 | 44025 |
| Naphthalene Green V | |
| Pontacyl Green NV Extra | |
| Basic Blue 11 | 44040 |
| Victoria Blue R | |
| Basic Blue 15 | 44085 |
| Night Blue | |

TABLE II-continued

| | |
|---|---|
| Acid Green 50 | 44090 |
| Wool Green S | |
| Kiton Green S Conc. | |
| Basic Green 3 | |
| Sevron Green B | |
| Brilliant Blue F & R Extra | |
| Brilliant Green Sulfonate | |
| Hexakis(hydroxyethyl) Pararosaniline | |

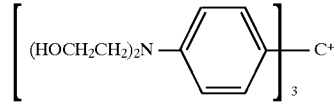

New Green

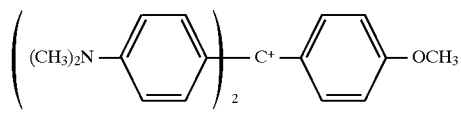

Phenolphthalein

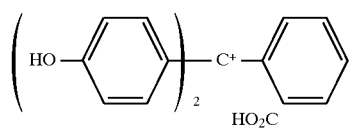

Malachite Green Ethiodide

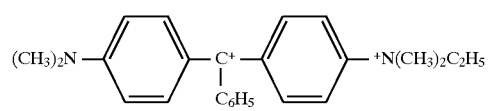

Hydroxyalkylated Pararosanilines

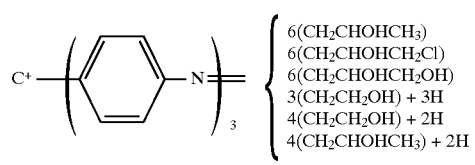

{ 6(CH$_2$CHOHCH$_3$)
6(CH$_2$CHOHCH$_2$Cl)
6(CH$_2$CHOHCH$_2$OH)
3(CH$_2$CH$_2$OH) + 3H
4(CH$_2$CH$_2$OH) + 2H
4(CH$_2$CHOHCH$_3$) + 2H }

Hydroxyalkylated New Fuchsins

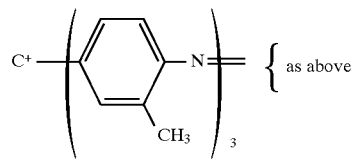 { as above }

New Yellow

Doebner's Violet

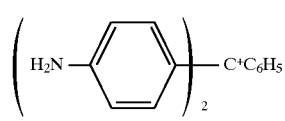

New Red

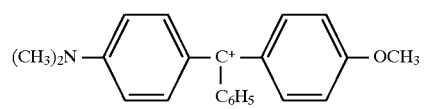

TABLE II-continued
Bis(hydroxyethyl) Doebner's Violet
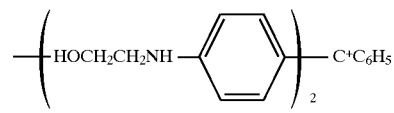
"New Magenta"
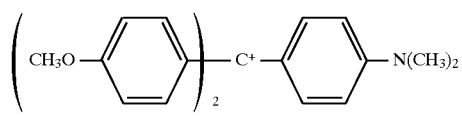
Tetrakis(hydroxyethyl) Doebner's Violet
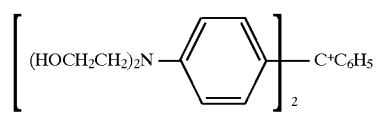
Trichloro Crystal Violet
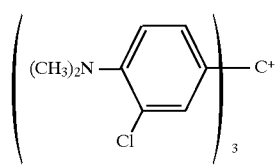
Slow Red
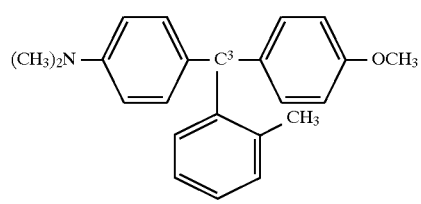
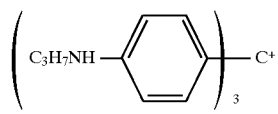
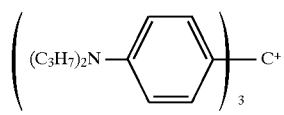
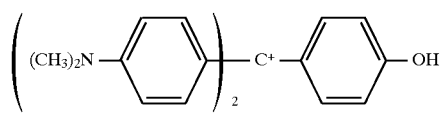
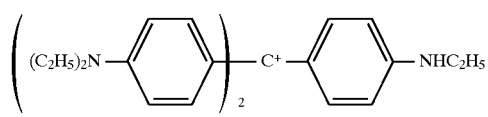
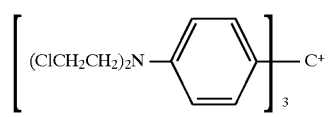
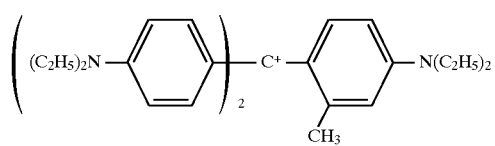

TABLE II-continued

[Structures of compounds shown:

1. ((CH₃)₂N—C₆H₄—)₂C⁺—C₆H₃(OCH₃)(NO₂)

2. ((CH₃)₂N—C₆H₄—)₂C⁺—C₆H₃(OCH₃)(NH₂)

3. ((CH₃)₂N—C₆H₄—)₂C⁺—naphthyl 4. (CH₃)₂N—C₆H₄—C⁺(—C₆H₄—F)(—naphthyl-N(CH₃)₂)

5. ((CH₃)₂N—C₆H₄—)₂C⁺—C₆H₄—C₆H₄—N(CH₃)₂

6. ((CH₃)₂N—C₆H₄—)₂C⁺—C₆H₄—C₆H₄—NHCOCH₃

7. [((CH₃)₂N—C₆H₄—)₂C⁺—C₆H₄—]₂ ]

[a] Only the cyanide, bisulfite, and hydroxide ions are considered, regardless of the other anions present in the solution.
[b] More detailed descriptions of the compositions of photochromic materials tested are given in Macnair's review [255; tables 1A–4].
[c] Ethanol.
[d] Diethyl ether.
[e] 1,2-Dichloroethane.
[f] 1,1-Dichloroethane, cyclohexane-1,1-dichloroethane, or cyclohexane-1,2-dichloroethane mixtures.
[g] Benzene.
[h] Dimethylsulfoxide, neat and aqueous.
[i] Acetone.
[j] Acetic acid.
[k] Ethyl acetate.
[l] Ethyl bromide.
[m] 2-Methoxyethanol.
[n] Chloroform.
[o] Ethanol with KCN.
[p] Ethanol wiih KOH.
[q] Carboxylic acids-acetic to stearic; hydrocinnamic acid; ethyl and butyl acid phthalates.
[r] Octadecylnitrile, tributyl phosphate, aniline, 2-(p-tert-butylphenoxy)ethanol, tetraethyleneglycol dimethyl ether, or poly(ethylene glycols).
[s] Amides-formamide to stearamide; methylformamide or methylacetamide; dimethyl- or diethyl-formamide or acetamide.
[t] Three-to-one solutions of cellulose acetate with any of the following five-to-one plasticizer mixtures:
Polyethylene Glycol 600 ®-butyl stearate, Polyethylene Glycol 600-butyl acetoxystearate,
Dowanol EP ®-butyl stearate, or Dowanol EP-butyl acetoxystearate.
[u] Water containing $SO_2$.
[v] Water containing bisulfite and papain.
[w] Poly(vinyl alcohol) with dimethylsulfoxide (5:1).

TABLE II-continued

[x] Films, containing residual solvent, cast from the following solutions: ethanol-acetone solutions of vinyl acetate-vinyl alcohol copolymer; aqueous poly(vinyl alcohol); aqueous poly(vinyl pyrrolidone); or aqueous methyl vinylether-maleic acid copolymer.

[y] Methanol-dioxane with aqueous $NH_4HSO_3$.

[z] Paper impregnated with a toluene solution of poly(methyl methacrylate), stearic acid, and 2-(p-tert-butylphenoxy)ethanol, then dried.

[aa] Intramicellar impregnation of cellulose with the following swelling agents: n-propylamine, n-butylamine, n-hexylamine, 2-aminoethanol, dimethylformamide, acetic acid, dimethylsulfoxide, methylacetamide, dimethylacetamide, or formamide.

[bb] Films cast from an approximately 4:3 mixture of a 20% solution and cellulose acetate butyrate in toluene-ethyl acetate (1:1) and triallycyanurate in dioxane.

[cc] Films cast from a 2:1 mixture of a 25% solution of cellulose acetate butyrate in toluene-ethyl acetate (1:1) and the titanium esters of N,N,N', N'-tetrakis(2-hydroxypropyl) ethylenediamine.

[dd] Pure water.

[ee] Films cast from aqueous gelatin or other hydrocolloids.

[ff] Dimethylsulfoxide with methanolic KCN.

[gg] 2-Methoxyethanol with methanolic KCN.

[hh] Water or aqueous methanol containing bisulfite.

[ii] Paper impregnated with m-dimethoxybenzene, acetonitrile, acetic acid, or phenyl methyl carbinol.

[jj] Ethanol-benzene.

[kk] Aqueous ethanol, methanol, aqueous methanol, aqueous acetone, benzene-methanol, carbon tetrachloride-methanol, cyclohexane-methanol, or chloroform-methanol.

[ll] Films cast from 3:1 solutions of cellulose acetate and either Polyethylene Glycol 600 ® or ethylene glycol phenyl ether as plasticizer.

[mm] Films, containing residual solvent, cast from solutions of either cellulose acetate in 2-methoxyethanol or poly(vinyl alcohol) in aqueous ethanol.

[nn] Films, containing residual solvent, cast from solutions of either cellulose acetate butyrate in 2-methoxyethanol or poly(vinyl acetate) in methanol.

[oo] Ethanol containing ammonia.

[pp] Aqueous methanol containing $NH_4HSO_3$ and urease.

[qq] Aqueous methanol containing $NH_4HSO_3$, with or without sodium dithionite.

[rr] Aqueous acid at pH 1.

[ss] Aqueous ammonia containing KCN.

[tt] Paper impregnated with aqueous solutions with or without hydrocolloids.

[uu] 2-Methoxyethanol containing HCl.

[vv] Aqueous methanol containing $NH_4HSO_3$, and glucose oxidase.

[ww] 9:1 Methanol-water.

[xx] Aqueous NaOH.

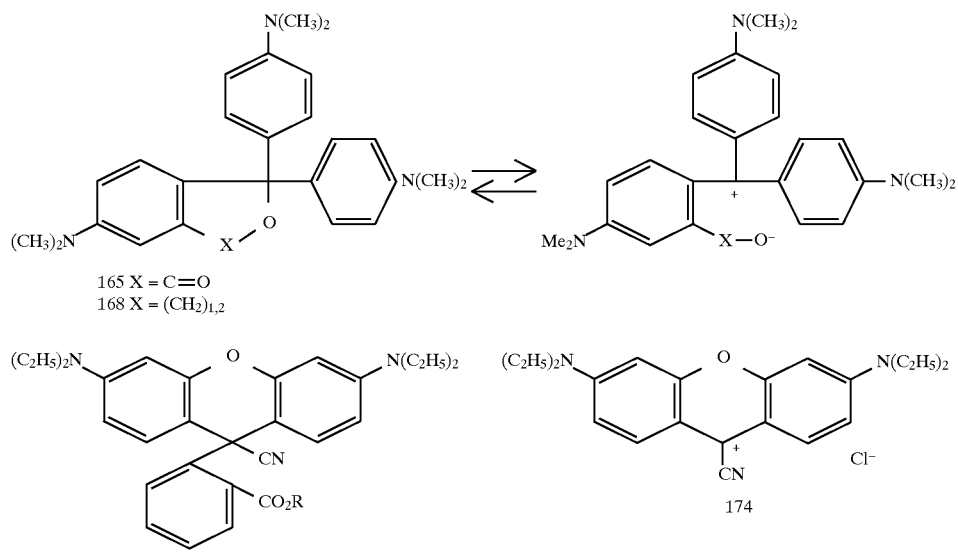

TABLE II-continued
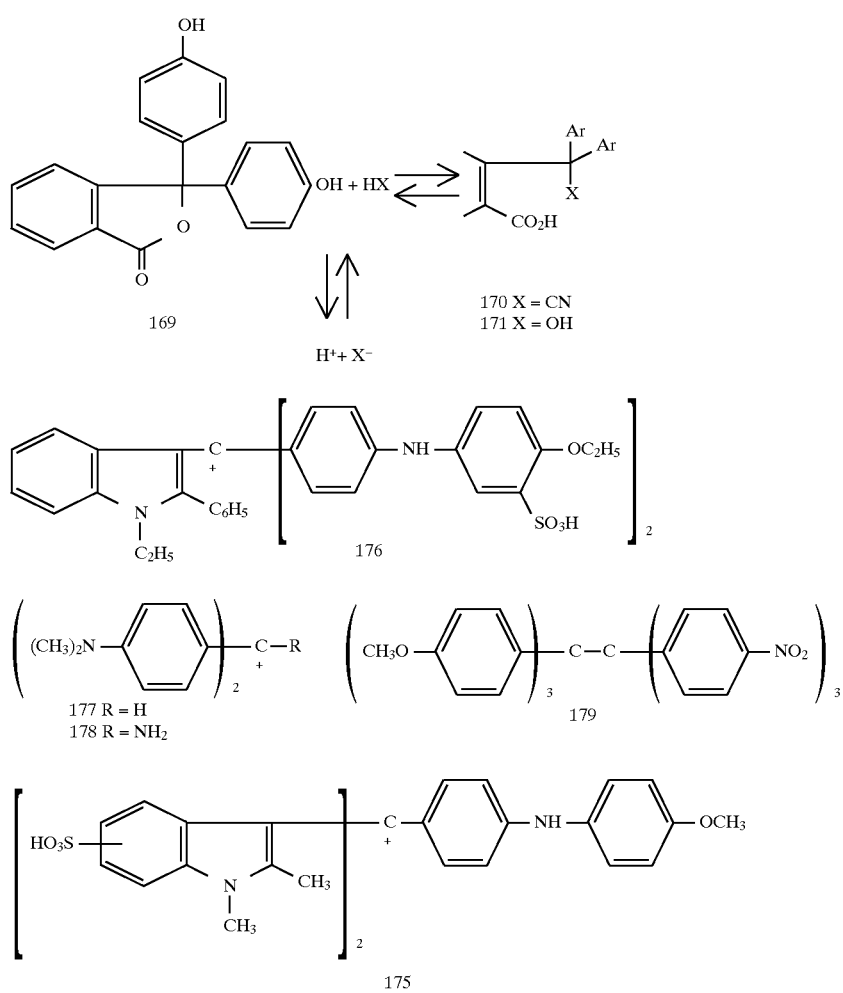
| Photochromic Polymethine Dyes |
|---|
α, ω-bis(p-Dimethylaminophenyl)polyenes
$$(CH_3)_2N-C_6H_4-\underset{Ar}{C^+}-(CH=CH)_n-CH=\underset{Ar}{C}-C_6H_4-N(CH_3)_2$$
| Ar | n |
|---|---|
| $C_6H_5$ | 0, 1, 2 |
| 4-$(CH_3)_2NC_6H_4$ | 0, 1, 2 |
| 4-$(CH_3)_2CHC_6H_4$ | 0, 1, 2, 3, 4 |
| 4-$CH_3OC_6H_4$ | 0, 1, 2 |
| 4-$C_4H_9OC_6H_4$ | 0, 1, 2 |
| 3-$CH_3C_6H_4$ | 1, 2 |
| 4-t-$C_4H_9C_6H_4$ | 1, 2 |
| 4-$C_2H_5OC_6H_4$ | 1, 2 |
| 4-$C_5H_{11}C_6H_4$ | 1, 2 |
| 4-$FC_6H_4$ | 1 |
| 4-$F_3CC_6H_4$ | 1 |
| 2-$(C_6H_5)_2NC_6H_4$ | 1 |
| 3,4-$H_2N(OCH_3)C_6H_3$ | 1 |
| 2-Naphthyl | 1, 2 |
| 4-$ClC_6H_4$ | 2 |
| 2,4-$Cl_2C_6H_3$ | 2 |
| 1-Naphthyl | 2 |

5,773,592
-continued
α, α-bis(p-dimethylaminophenyl)polyenes
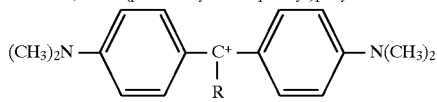
| R | R |
|---|---|
| 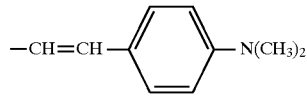 | 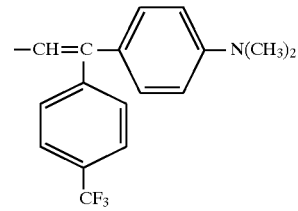 |
| 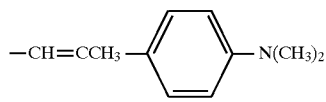 | |
| 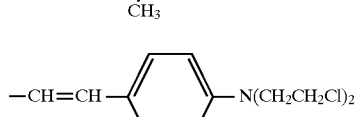 | 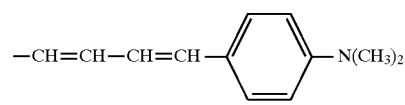 |
| 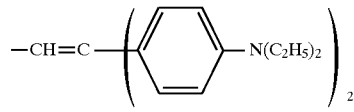 | 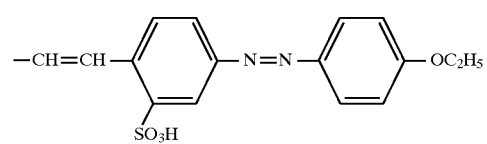 |
| | —CH=N—N(C₆H₅)₂ |
| 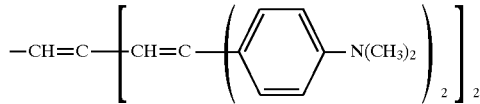 | 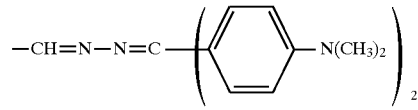 |
| | 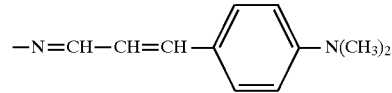 |
| 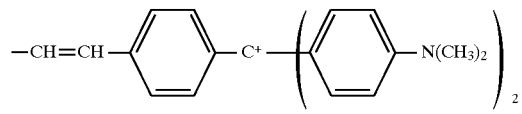 | 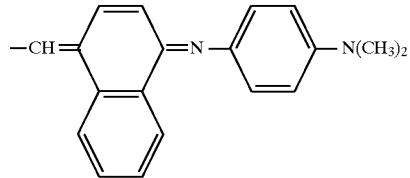 |
| 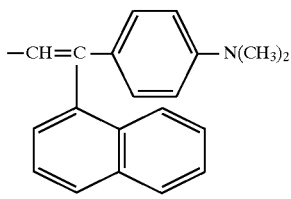 | 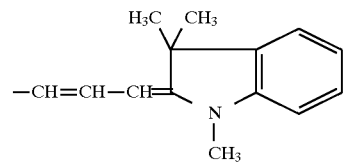 |

| | Miscellaneous polyenes |
|---|---|
| | 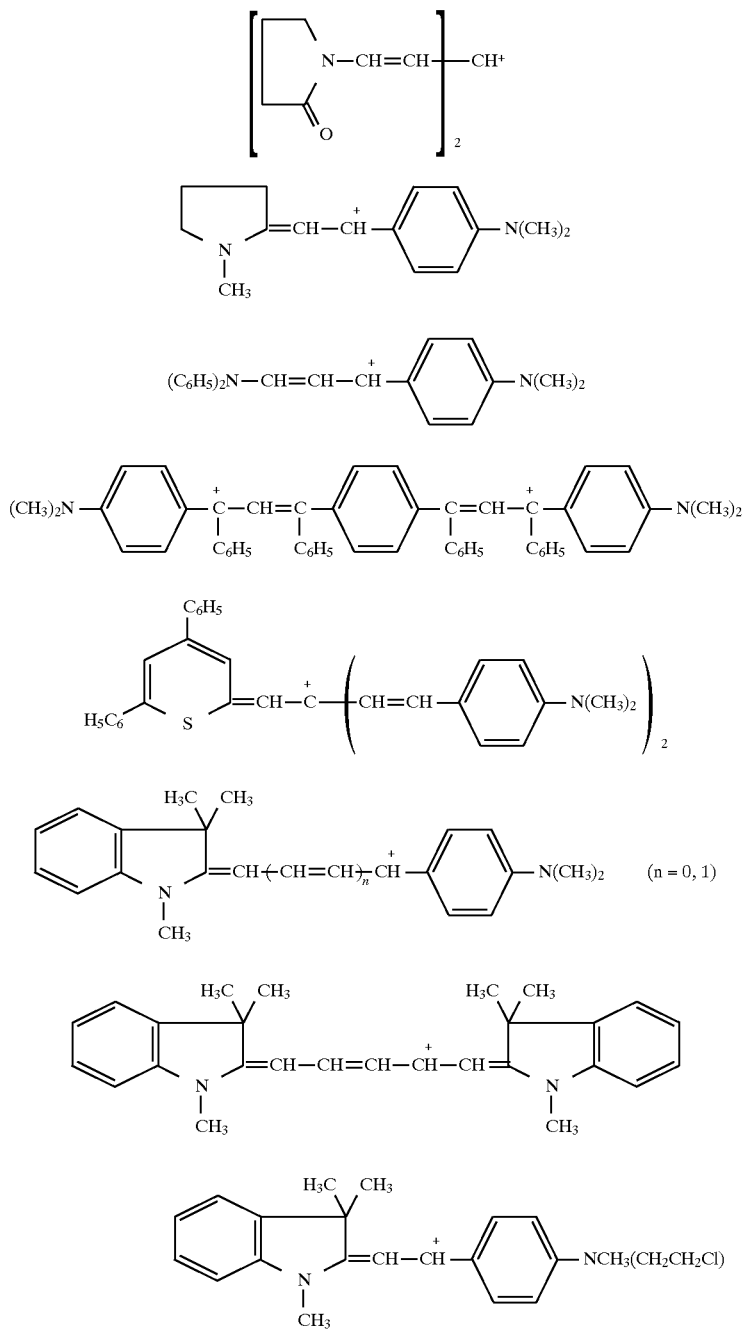 |
| Basic Red 13 | |
| Basic Violet 7 | |
| Basic Red 14<br>Basic Red 15<br>Basic Violet 15 | 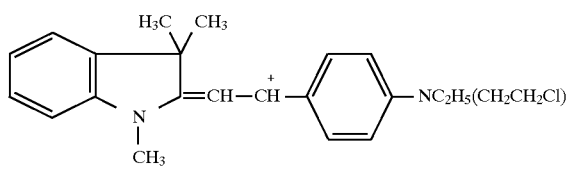 |

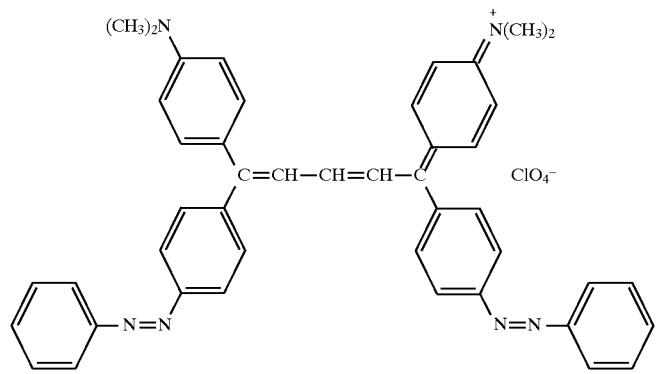
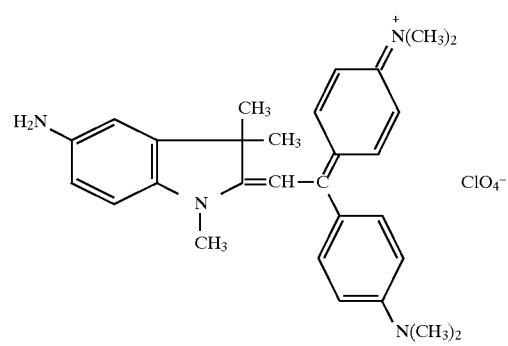
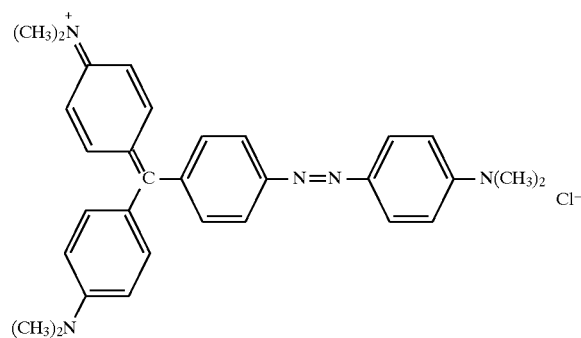
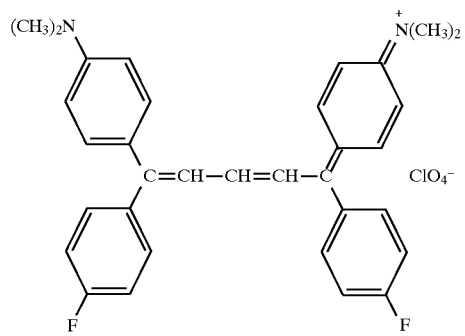

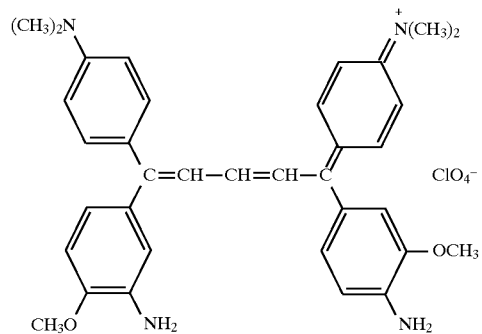
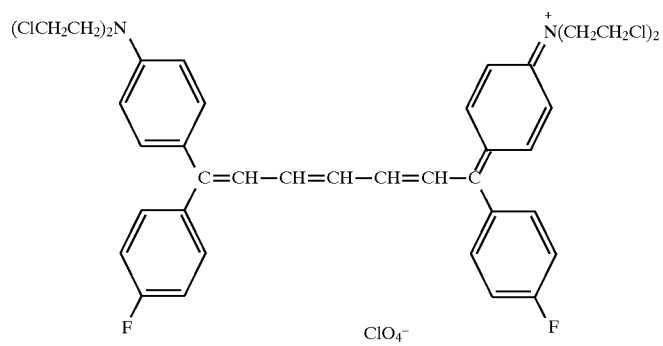
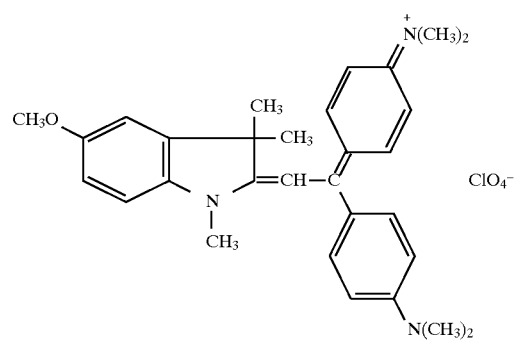
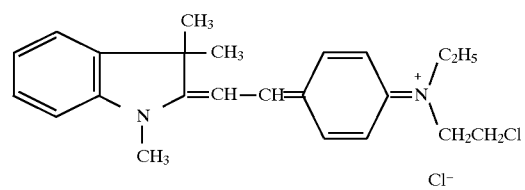
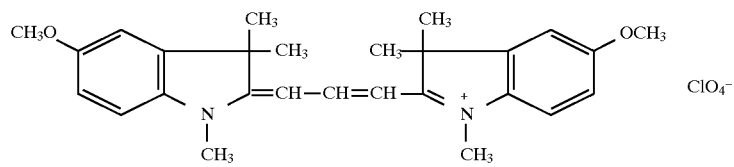

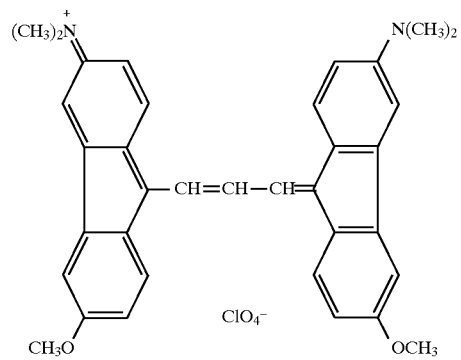
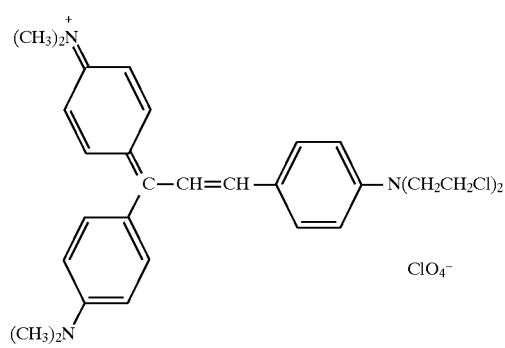
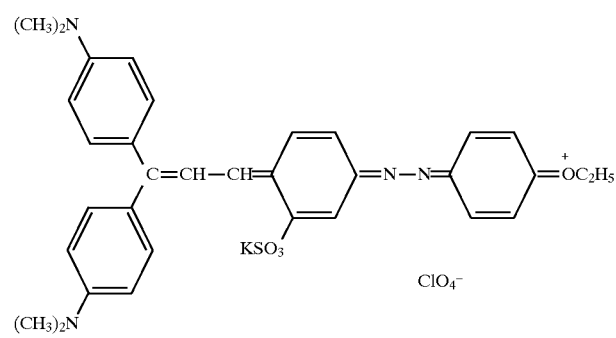
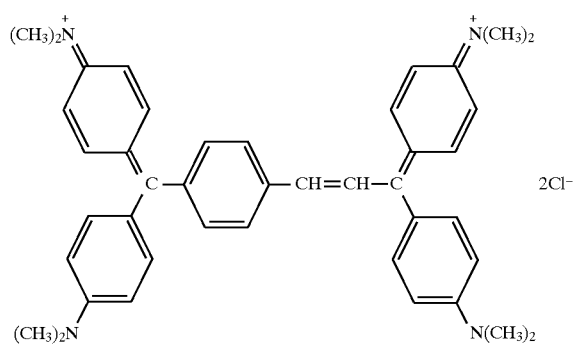

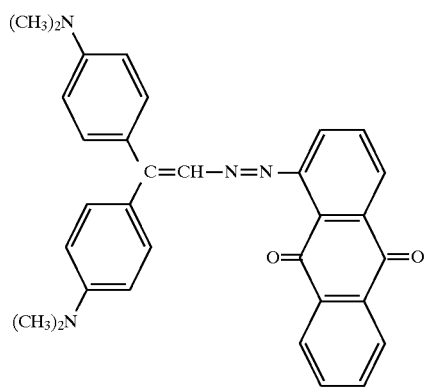
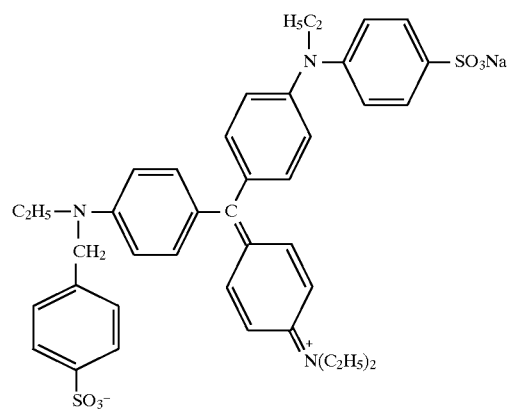
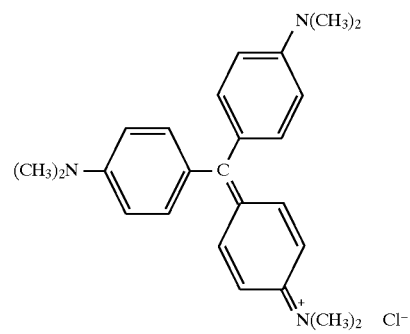
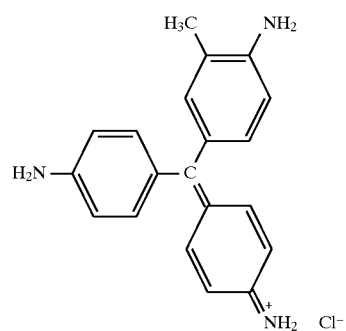

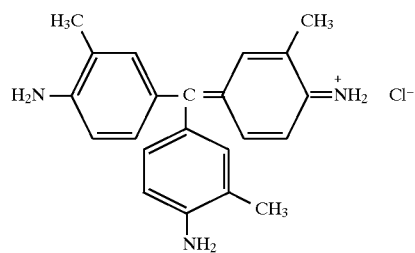
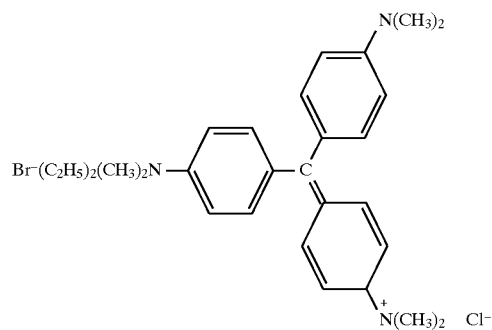
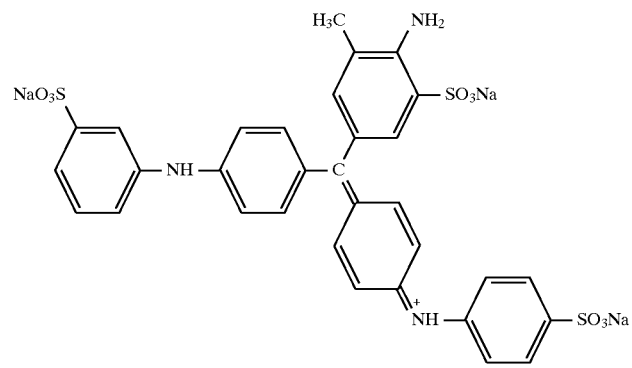
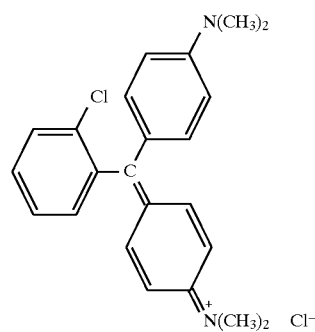
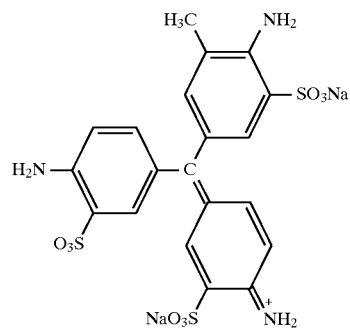

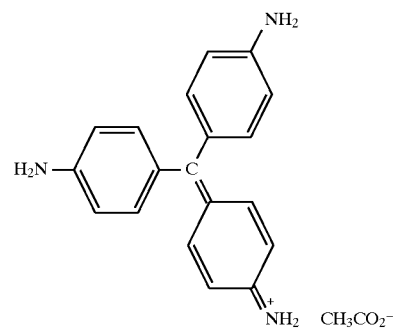
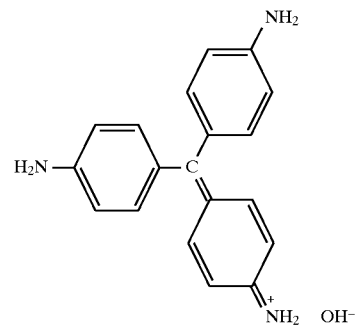
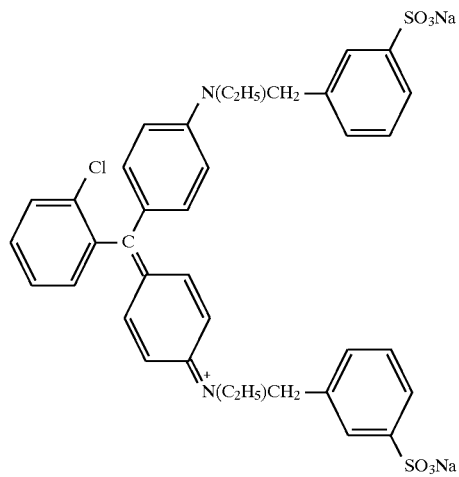
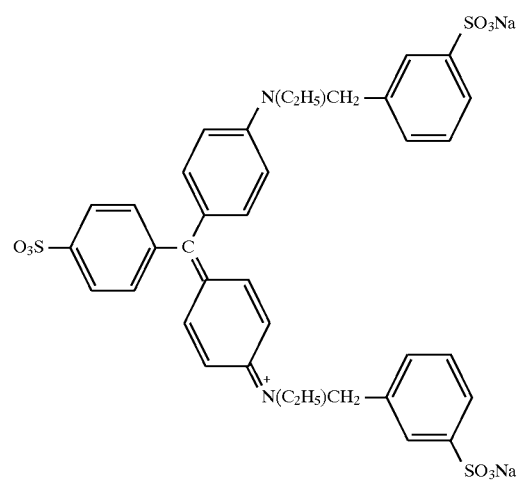

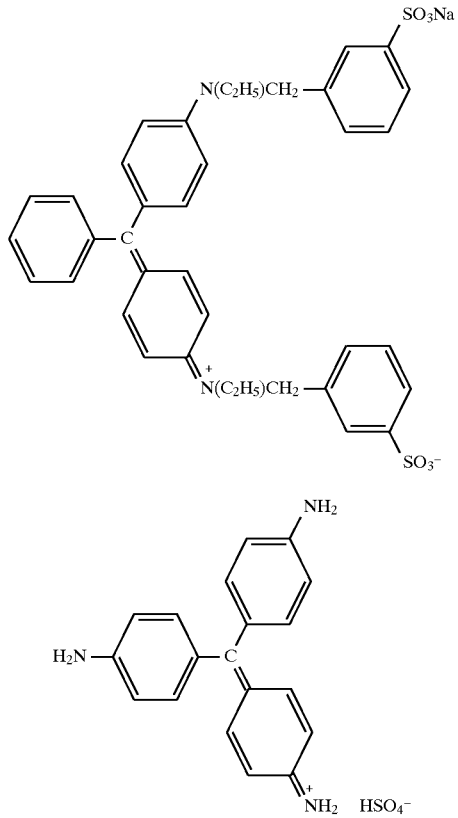
| SALT-ISOMERISM TYPE PHOTOTROPIC DYES |
|---|
Night Blue
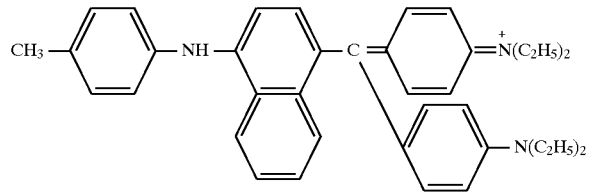
Victoria Blue R
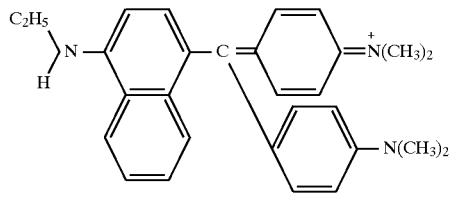
Brilliant Milling Blue B
Brilliant Blue F & R Ex.
Eriocyanine A
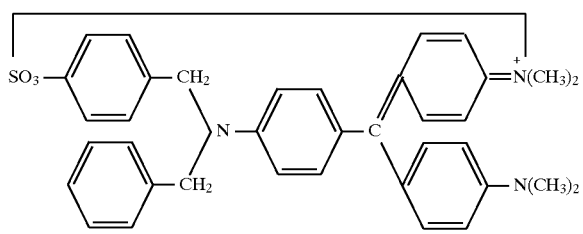

Methyl Blue
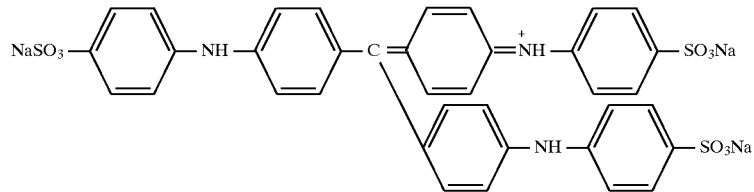
Aniline Blue
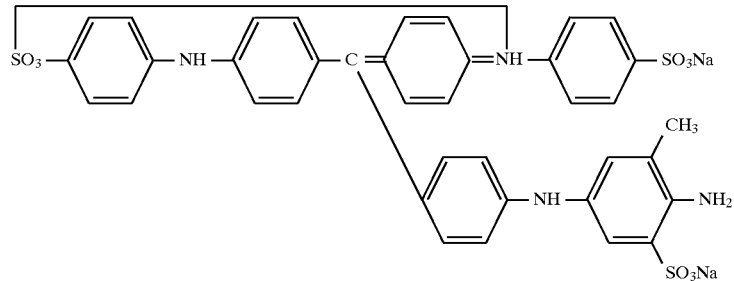
Eriochrome Cyanine R
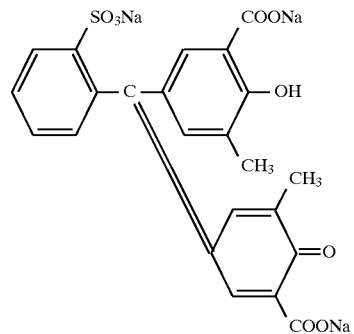
Methyl Violet 6B
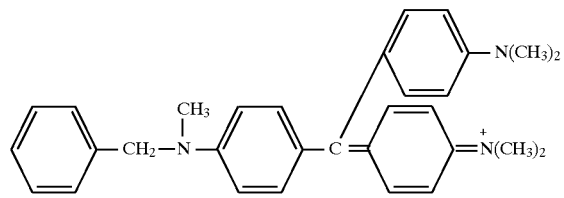
Iodine Green
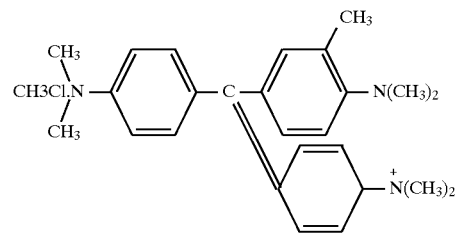
Aniline Blue
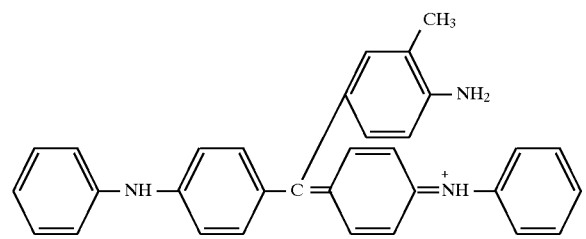

Wool Violet 5 BN
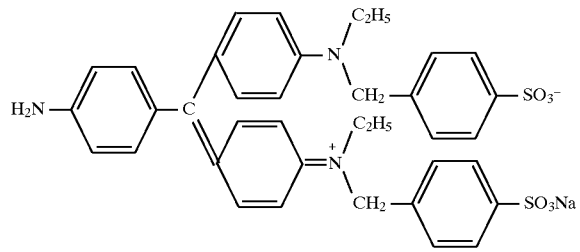
Wool Violet 4 EM
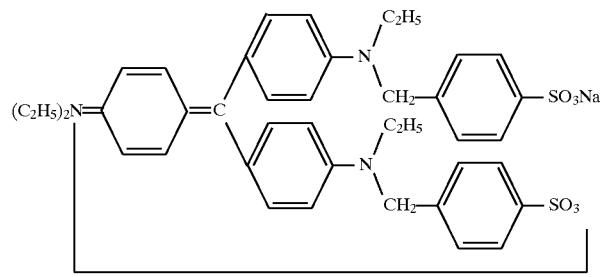
Light Green SF Yellowish
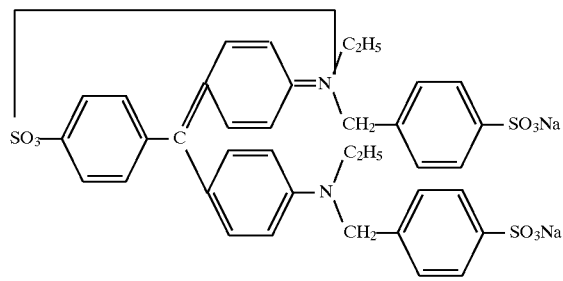
Iodine Violet
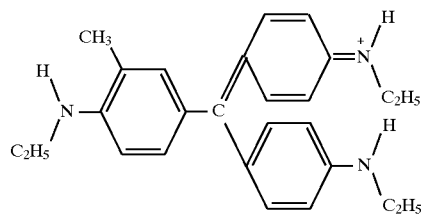
Methyl Violet
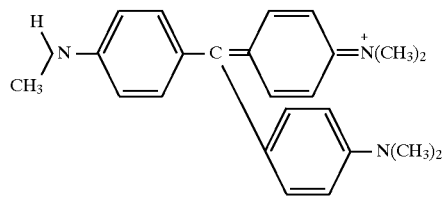
Crystal Violet
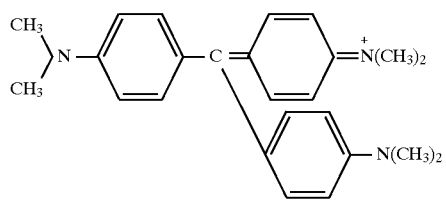

Ethyl Violet
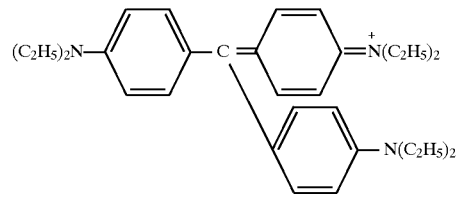
Acid Green L Extra
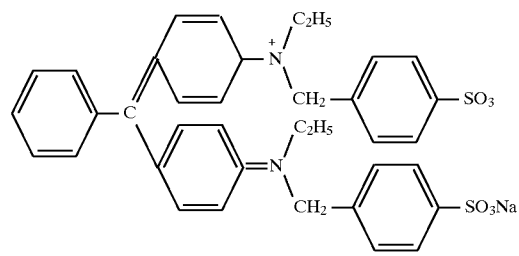
Erioviridene B
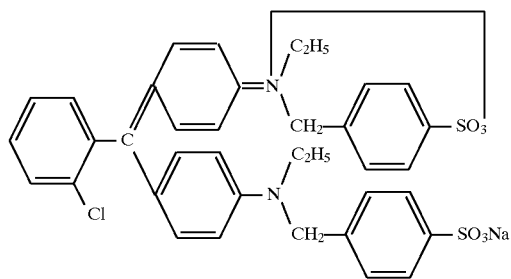
Light Green SF
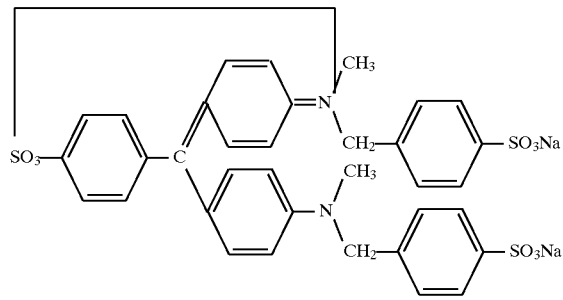
Victoria Green
(Malachite Green)
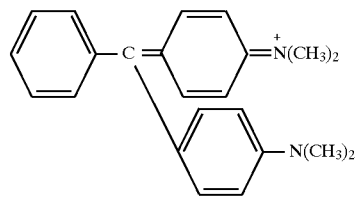

Red-Violet 5R
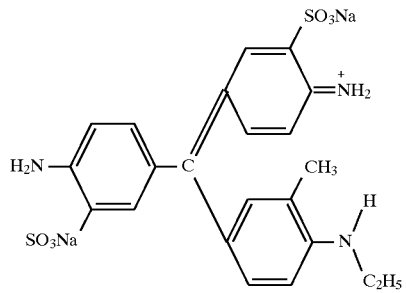
Brilliant Green "B"
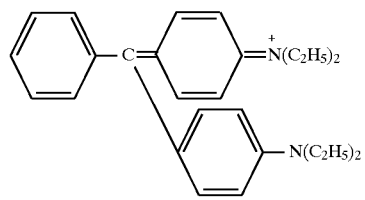
Di-[4(N,N-diethylamine)phenyl]-[4-(N,N-diethyl-
amine-2-methyl) phenyl] methyl carbonium
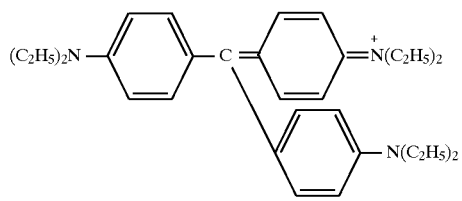
Tri-[4(N,N-dipropylamino)phenyl] methyl carbonium
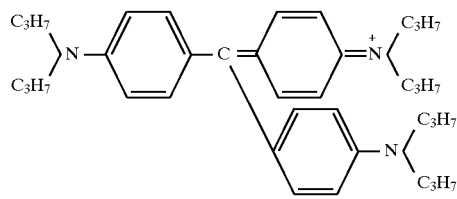
Di-[4(N,N-diethylamino)phenyl]-[4(ethylamino)-
phenyl] methyl carbonium
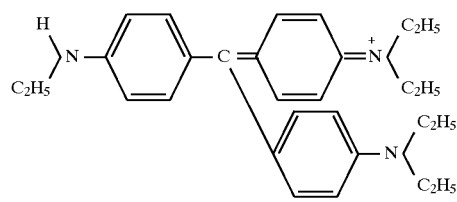
Di-[4(N,N-diethylamino)phenyl]-[4(N,N-diethyl-
amino)naphthyl] methyl carbonium
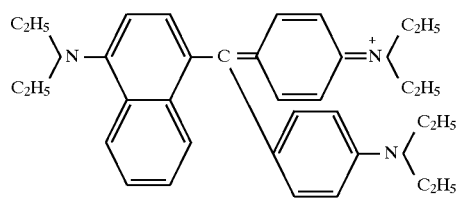

Di-[4(N,N-dimethylamino)phenyl]-[4(hydroxy)phenyl] methyl carbonium

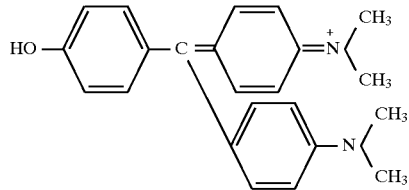

Tri-[4(N-propylamino)phenyl] methyl carbonium

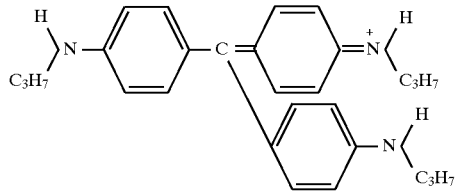

Hectolene Blue DS-1398
Hectolene Blue DS-1823
Sevron Brilliant Red 4G
Di-[4(N,N-dimethylamino)phenyl]-[4(hydroxy)phenyl] methyl carbonium

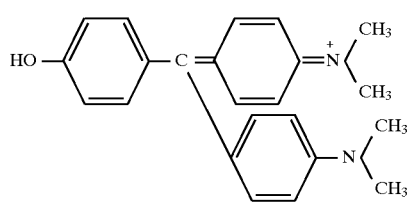

Tri-[4(N-propylamino)phenyl] methyl carbonium

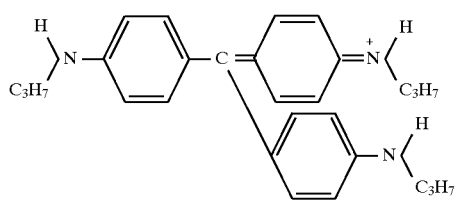

Hectolene Blue DS-1398
Hectolene Blue DS-1823
Sevron Brilliant Red 4G
Genacryl Red 6B
Genacryl Pink G
Sevron Brilliant - Red B
Sevron Brilliant - Red 3B
1,5-bis-[4(N,N-dimethylamino)phenyl]-1,5-bis-(phenyl)divinyl carbonium trifluoroacetate

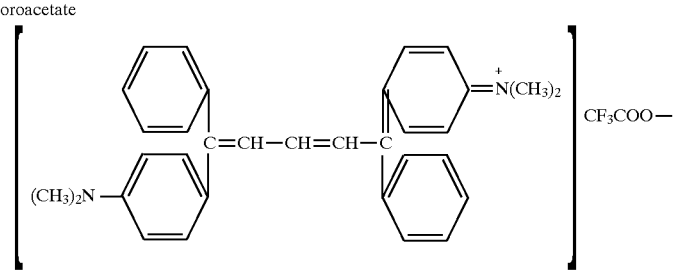

-continued 1,1,3,3-tetrakis[4(N,N-dimethylamino)phenyl] vinyl carbonium perchlorate

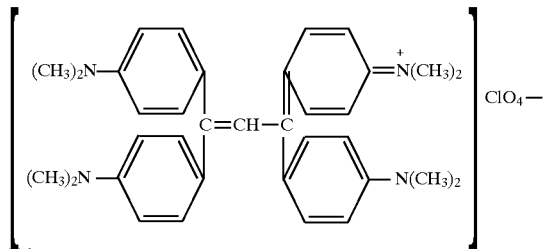

1,5-bis-[4(N,N-dimethylamino)phenyl]-1,5-bis-(phenyl) divinyl carbonium p-toluenesulfonate

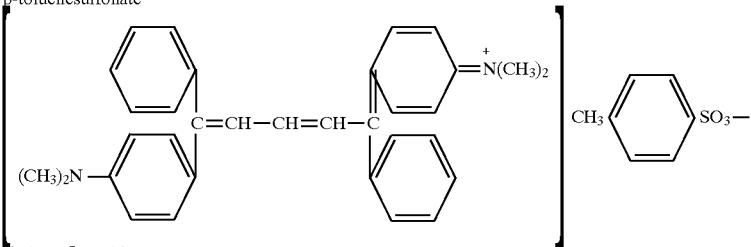

1,7-bis[4(N,N-dimethylamino)phenyl]-1,7-bis-(2,4-dichlorophenyl) trivinyl carbonium perchlorate

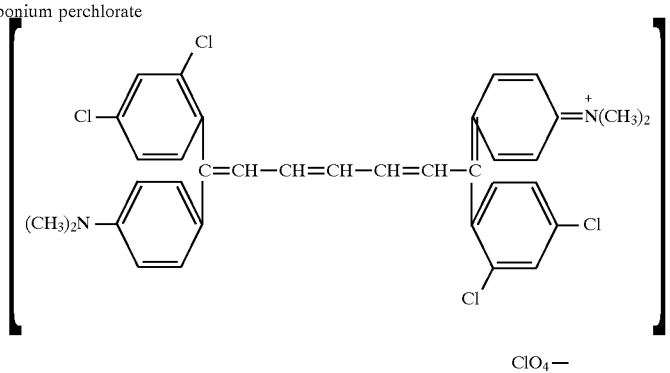

Di-[4(N,N-dimethylamino)phenyl vinyl]-[2,4-diphenyl-6-methane thiopyran] methyl carbonium perchlorate

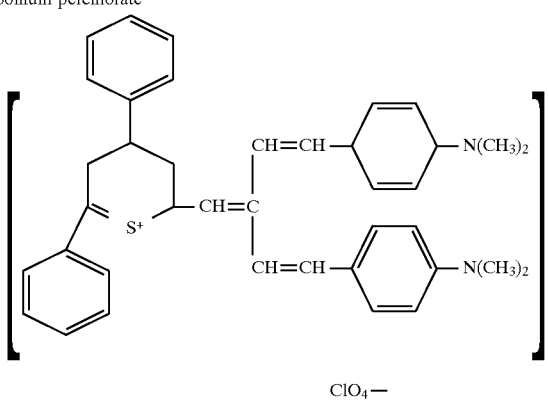

1,7-bis-[4(N,N-dimethylamino)phenyl]-1,7-bis-(4-chlorophenyl) trivinyl carbonium trifluoroacetate

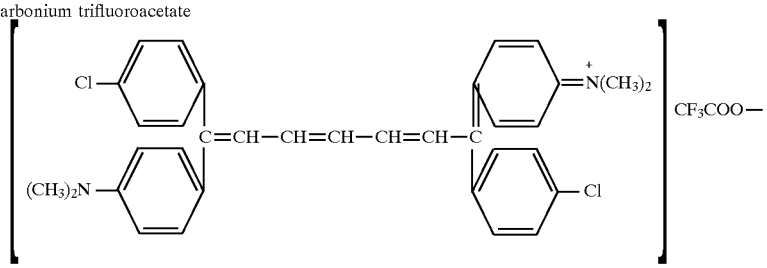

1,1,3-tris-[4-(N,N-dimethylamino)phenyl] divinyl
carbonium perchlorate
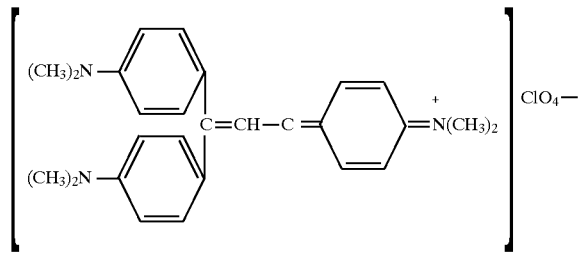
1,1,7,7-tetrakis-[4-(N,N-dimethylamino)phenyl]
trivinyl carbonium perchlorate
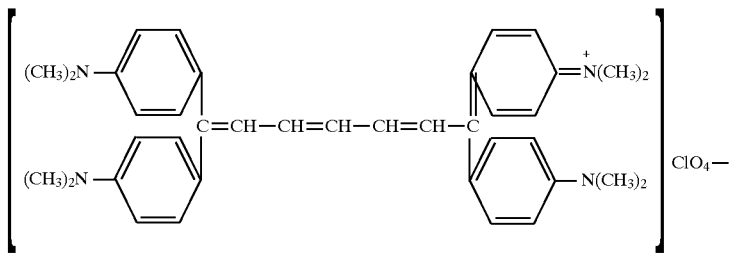
1,3-bis-[4-(N,N-dimethylamino)phenyl]-1,3-bis-
(phenyl) vinyl carbonium perchlorate
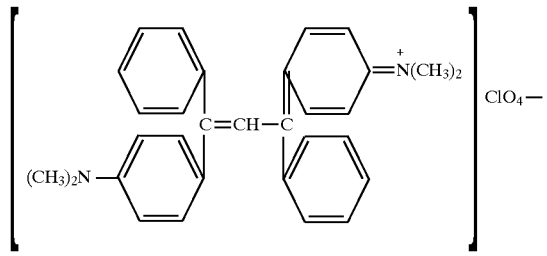
1,1,5,5-tetrakis-[4-(N,N-dimethylamino)phenyl]
divinyl carbonium perchlorate
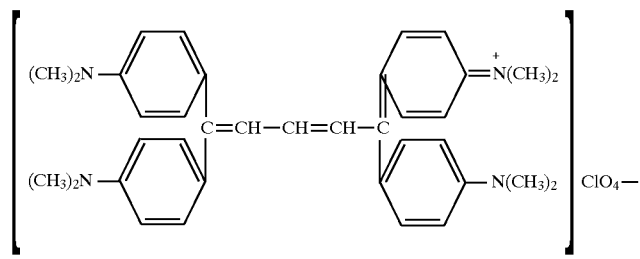
1,5-bis-[4-(N,N-dimethylamino)phenyl]-1,5-bis-
(phenyl) divinyl carbonium perchlorate
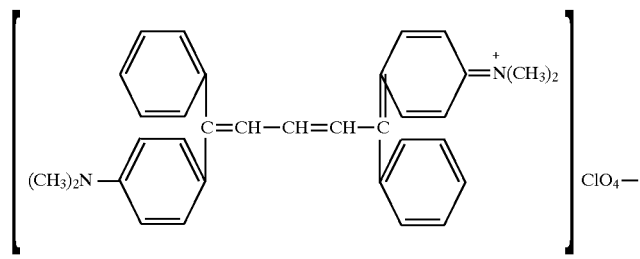

1,7-bis-[4-(N,N-dimethylamino)phenyl]-1,7-bis-
(phenyl) trivinyl carbonium trifluoroacetate

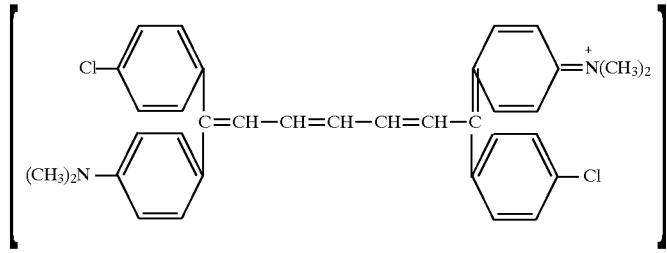

CF₃COO—

1(1,3,3-trimethyl indoline)-2-[4-(N,N-dimethyl-
amino)phenyl] ethylene carbonium perchlorate

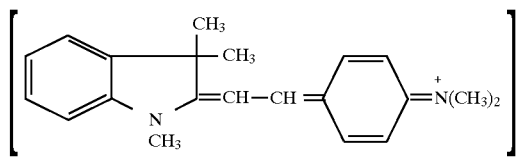

ClO₄—

1(1,3,3-trimethyl indoline)-4-[4-(N,N-dimethyl-
amino)phenyl] butylene carbonium perchlorate

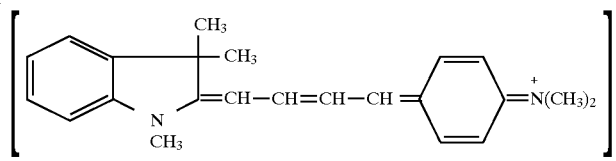

ClO₄—

1,1,3,3-tetrakis-[4(N,N-diethylamino)phenyl]
vinyl carbonium perchlorate

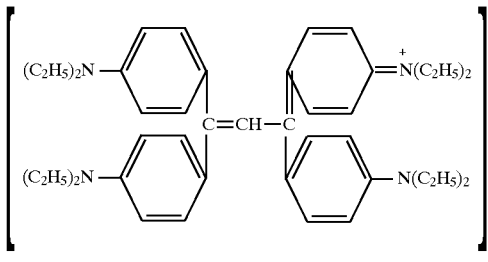

ClO₄—

1,1-bis-[4-(N,N-diethylamino)phenyl]-3,3-bis-
[4-(N,N-dimethylamino)phenyl] vinyl carbonium perchlorate

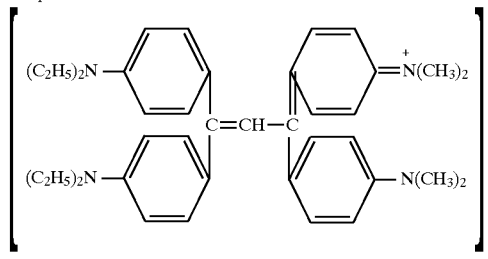

ClO₄—

1,1,5,5-tetrakis-[4-(N,N-diethylamino)phenyl] divinyl carbonium perchlorate
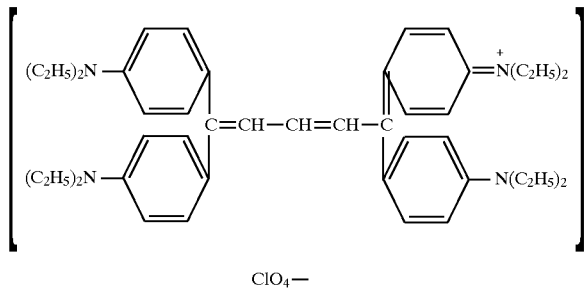
1,1-bis-[4-(N,N-dimethylamino)phenyl]-3-[4-(amino)phenyl]-3-methylvinyl carbonium perchlorate
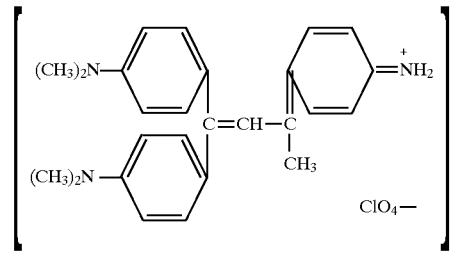
Tris-[1,1-bis-[4(N,N-dimethylamino)phenyl] ethylene] methyl carbonium perchlorate
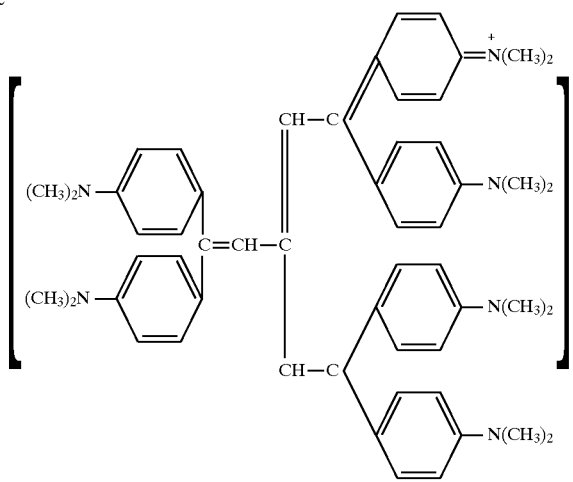
Tris-[1,1-bis-[4-(N,N-diethylamino)phenyl] ethylene] methyl carbonium perchlorate
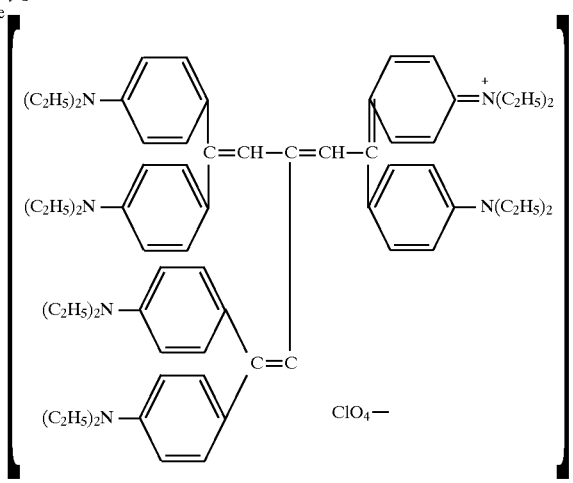

-continued
1,1,5-tris-[4-(N,N-dimethylamino)phenyl] divinyl
carbonium perchlorate
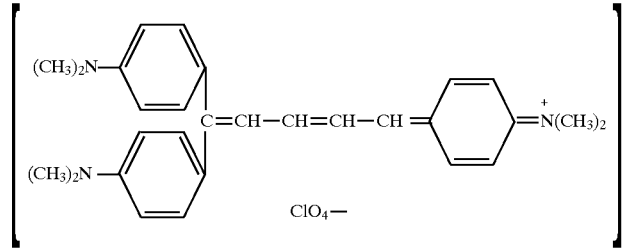
N[4-(N,N-dimethylamino) cinnamylidene] auramine
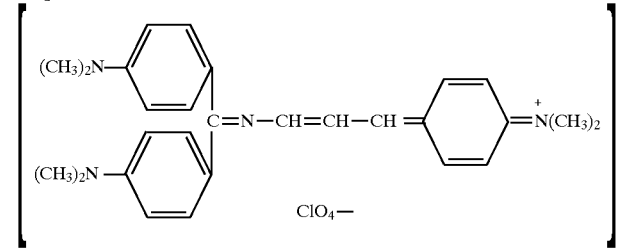
1,1-bis-[4-(N,N-dimethylamino)phenyl-3,4-bis-
(phenyl)]-3,4-diazo butene carbonium
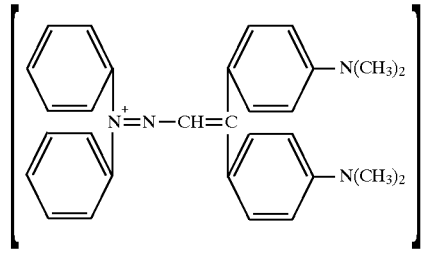
1,1,5,5-tetrakis-[4-(N,N-dimethylamino)phenyl]-
2,3-diazo pentene carbonium
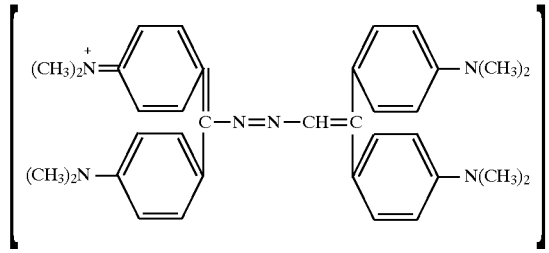
N-(N',N'-dimethylamino cinnamylidene)-N,N-diphenyl
ammonium
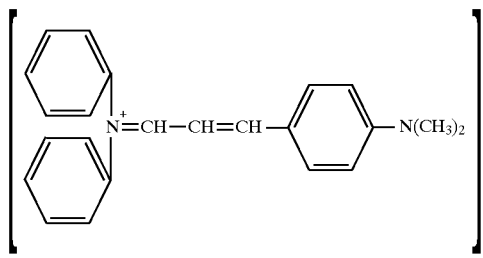
Azo Polymethines
Dyes of the general structural type
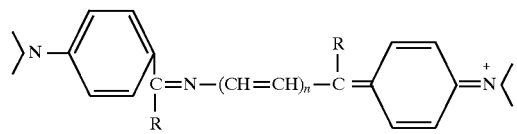

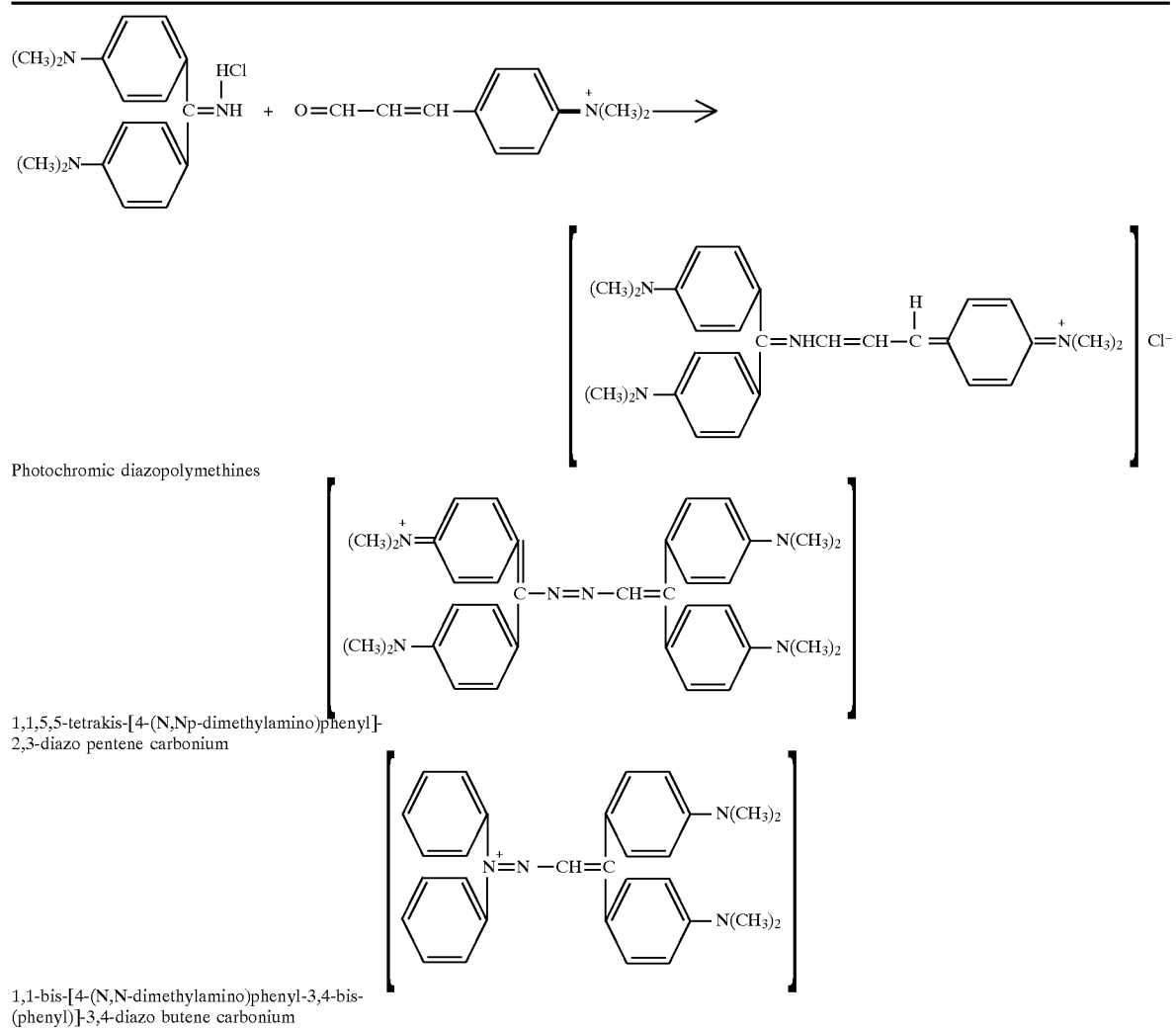

The drug functionality, C, includes any molecule which exhibits bleaching behavior with the B functionality and has an increased therapeutic effect or therapeutic ratio as a consequence of its delivery as part of a Luminide agent. For example, Foscarnet, a viral reverse transcriptase inhibitor possesses both a carboxylate and phosphate group which will bleach photochromic compounds; 4-bromocrotonyl-CoA, an acetoacetyl-CoA thiolase inhibitor, possesses a thiol group which will bleach photochromic compounds; L-3-iodo-a-methyltyrosine, a tyrosine hydroxylase inhibitor, possesses a carboxylate group which will bleach photochromic compounds, and captopril, an antihypertensive pharmaceutical, possesses both a sulfide and carboxylate group which will bleach photochromic compounds. Furthermore, the pharmacokinetics and/or pharmacodynamics of these agents are altered via delivery to the site of action by way of a luminide agent such that the therapeutic effect or therapeutic ratio is enhanced.

Other drugs which are not inherently photochromic bleaches in that they lack a nucleophilic group which will form a reversible covalent bond with the B functionality can be derivatized with a known bleaching nucleophilic group such as cinnamate, sulfite, phosphate, carboxylate, thiol, or amine group to transform them into bleaching agents of the B functionality such as a cationic dye. See Table 3 below for the structure of a exemplary drug molecules.

TABLE 3
Representative Drug Molecules.
| Name | Structure |
| --- | --- |
| Captopril | 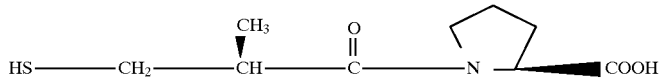 |
| Prostaglandin E$_2$ | 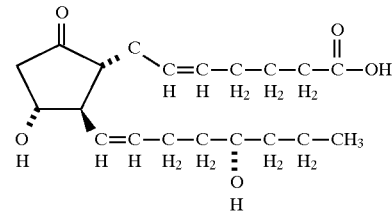 |
| 2,3-dichloro-α-methyl-benzylamine | 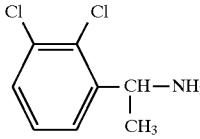 |
| 3'-deoxy-S-adenosyl-L-homocysteine | 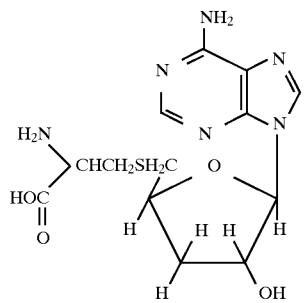 |
| Sinefungin | 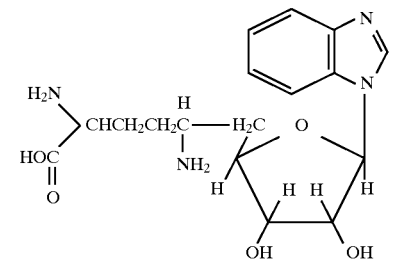 |
| 3,5-diiodo-4-hydroxy-benzoic acid | 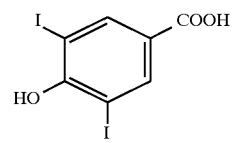 |
| 6,6'-dithiobis (9-B-D-ribofuranosylpurine) | 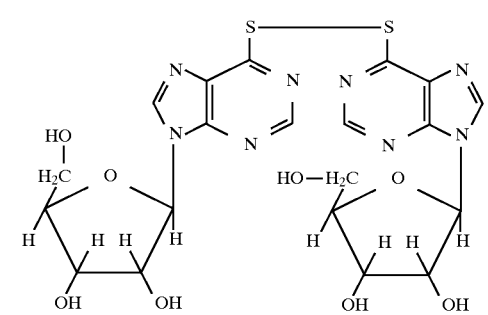 |
| γ-aminobutyric acid | H$_2$NCH$_2$CH$_2$CH$_2$COOH |

TABLE 3-continued

Representative Drug Molecules.

| Name | Structure |
|---|---|
| Gabaculine | 3-amino-cyclohexa-1,5-diene-1-carboxylic acid (benzene ring with COOH and NH$_2$) |
| N-(5'-phosphopyridoxy)-4-aminobutyric acid | Pyridoxal phosphate derivative with CH$_2$OP(=O)(OH)$_2$, CH$_2$NHCH$_2$CH$_2$CH$_2$COOH, CH$_3$, OH substituents |
| 4-amino-hex-5-enoic acid | CH$_2$=CHCH(NH$_2$)CH$_2$CH$_2$COOH |
| Baclofen | 4-Cl-C$_6$H$_4$-CH(CH$_2$NH$_2$)CH$_2$COOH |
| Adenosine | Adenine attached to ribose (standard adenosine structure) |
| 3-hydroxy-3-methyl-glutarate | CH$_3$CH$_2$C(OH)(CH$_3$)CH$_2$COOH |
| Campactin | Mevastatin-type structure: decalin with methyl, 2-methylbutanoate ester, and side chain with OH and COOH |

TABLE 3-continued

Representative Drug Molecules.

| Name | Structure |
|---|---|
| But-3-ynoyl-CoA | 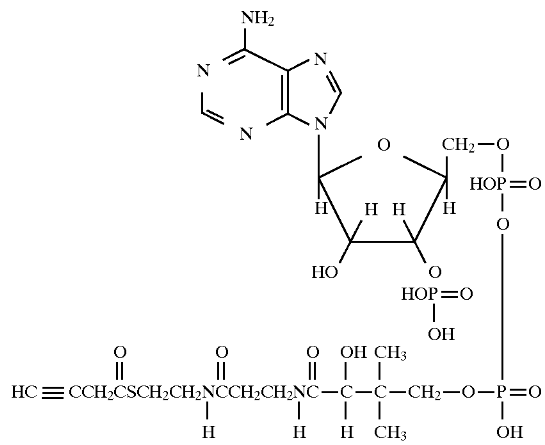 |
| Suramin | 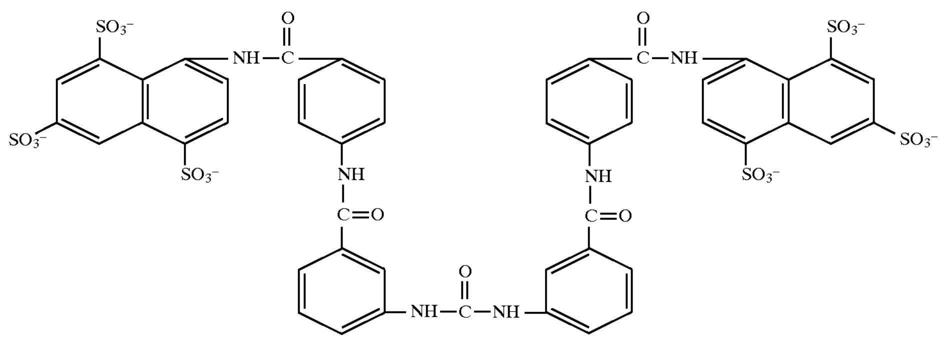 |
| L-3-iodotyrosine | 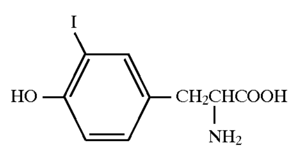 |
| L-3-iodo-α-methyltyrosine | 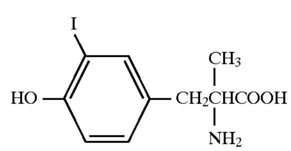 |
| Disodium cromoglycate | 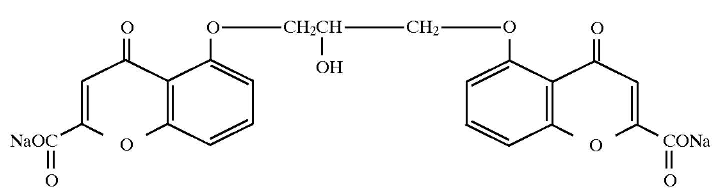 |

TABLE 3-continued

Representative Drug Molecules.

| Name | Structure |
| --- | --- |
| Adenosine 3',5'-cyclic monophosphate | 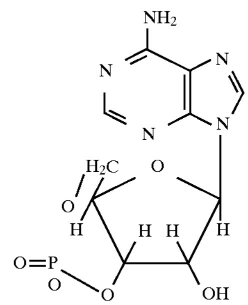 |
| D,L-B-(5-hydroxy-3-indolyl)-α-hydra-zinopropionic acid | |
| D,L-α-hydrazino-α-methyldopa | 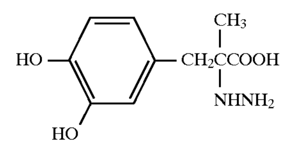 |
| α-methyldopa | 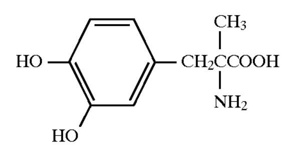 |
| 5-(3,4-dihydroxycinna-moyl)salicylic acid | |
| N-(phosphonacetyl)-L-aspartate | 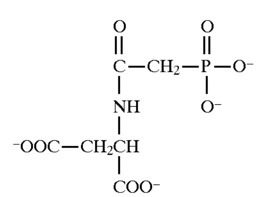 |
| P-glycolohydroxamate | 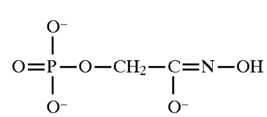 |
| 5-(p-sulfamylphenyl-azosalicylic acid | 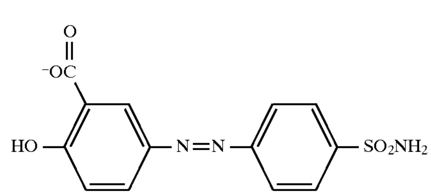 |

/ TABLE 3-continued

Representative Drug Molecules.

| Name | Structure |
| --- | --- |
| Coformycin | (structure) |
| Formycin B | (structure) |
| Thioinosinate | (structure) |
| Phosphonoformate | $^-OP(=O)(O^-)-C(=O)O^-$ |
| Phosphonoacetate | $^-OP(=O)(O^-)-CH_2-C(=O)O^-$ |
| Ridavirin | (structure) |
| Sotalol | $CH_3SO_2NH-C_6H_4-CH(OH)CH_2NHCH(CH_3)_2$ |

TABLE 3-continued

Representative Drug Molecules.

| Name | Structure |
|---|---|
| Cimetidine | (structure shown) |
| Fuscaric acid | (structure shown) |
| 2-mercaptoethylamine | $HSCH_2CH_2NH_3^+$ |
| Mimosine | (structure shown) |
| U-7130 | (structure shown) |
| Iproniazid | (structure shown) |
| Trans-4-aminoocrotonic acid | $H_2NCH_2CH=CHCOOH$ |
| NSD 1055 | (structure shown) |
| Nicotinic acid | (structure shown) |
| Kynurenic acid | (structure shown) |

TABLE 3-continued

Representative Drug Molecules.

| Name | Structure |
|---|---|
| Lentysine | 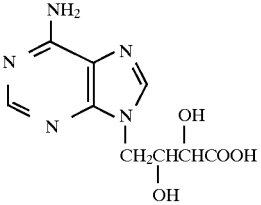 |
| Orotic acid | 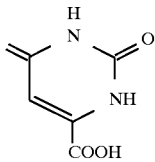 |
| Polyoxin D | 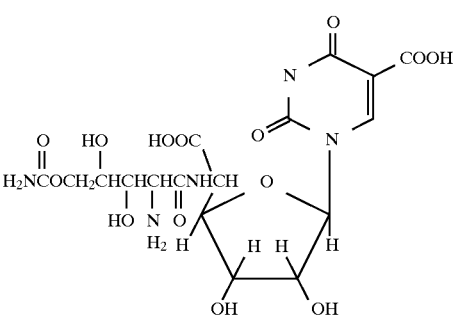 |
| Cephalosporin | 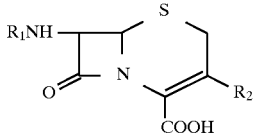 |
| Penicillin | 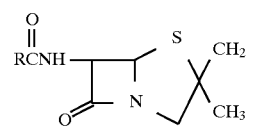 |

The electron transfer functionality, D, includes molecules which undergo a redox reaction which transfers electrons between the electron carriers and the A functionality where a redox reaction of A results in its activation to an excited energy state. The D functionality can be a natural electron carrier such as ubiquinone or a synthetic electron carrier such as methylene blue, phenazine methosulfate, or 2,6-dichlorophenolindophenol. Structures of electron transfer molecules appear below in Table 4.

TABLE 4

Representative Electron Transfer Molecules.

| Name | Structure |
|---|---|
| Methylene Blue | 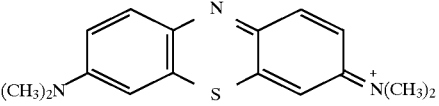 |
| Ubiquinone | 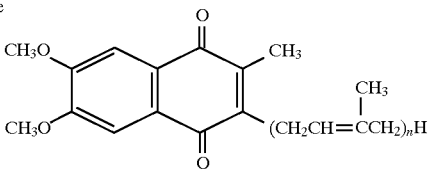 |

TABLE 4-continued

Representative Electron Transfer Molecules.

2,6-dichlorophenolindophenol

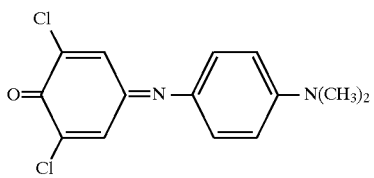

Phenazine methosulfate

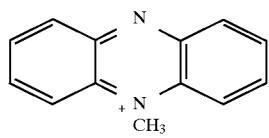

Ferricyanide

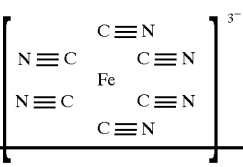

A Representative Luminide

A representative luminide is the product of the covalent linkage of the polymethine dye with a bleaching drug such as Foscarnet and with a chemiluminescent reactive molecule such as luminol. This conjugate represents a molecule which releases Foscarnet in the presence of oxygen free radicals. The energy of the reaction of luminol with oxygen radicals undergoes intramolecular electronic energy transfer by radiative and nonradiative mechanisms. The latter dominate and include coulombic interactions, dipole-dipole resonance, and exchange interaction. These processes increase the quantum yield for drug release above that which would be produced by luminescence transfer alone. For example, Forster, in a quantum mechanical treatment of resonance transfer, in the region of spectral overlap involving allowed transitions of two well separated molecules has only considered dipole-dipole interactions in deriving an experimentally verified formula which predicts a distance of 5–10 nm as the distance at which transfer and spontaneous decay of the excited donor are equally probable. The formula predicts the transfer probability is inversely proportional to the separation distance raised to the sixth power. However, the donor and accepter functionalities of a Luminide are covalently linked;

thus, since the separation distance is of the order of angstroms, the transfer probability is great. In fact, the efficiency of transfer has been studied in certain molecules which consist of two independent chromophores separated by one or more saturated bonds. In such cases, energy transfer over large distances has been observed to be in agreement with predictions from Forster's Theory.

The Luminides can be prepared by known reactions where necessary, appropriate derivatives of the subunits are formed before coupling.

Representative examples of appropriate derivatization and coupling reactions are given in the following examples, illustrating the preparation of representative Luminides. These examples are not to be taken as an exhaustive listing, but only illustrative of the possibilities according to the present invention.

Representative Luminides with Outline of Synthetic Pathway.

Luminides synthesis involves the chemical joining of three or four functionalities. A representative luminide of three functionalities comprises an energy donor molecule such as a chemiluminescent molecule, an energy acceptor molecule such as a photochromic molecule, and a drug. A representative luminide of four functionalities comprises the mentioned three functionalities and also an electron transfer functionality which can undergo an oxidation reduction reaction.

A three group Luminde can be formed by condensing a photochromic dye functionalized as an acid chloride with a chemiluminescent molecule possessing an alcoholic or amino group to form an ester or amide. The luminide pharmaceutical is then formed by addition of the drug bleaching agent. An exemplary pathway of this type appears in example 1.

Alternately, the chemiluminescent and/or electron transfer functionality can be linked to the energy acceptor functionality by formation of an ester or amide where the former functionality/functionalities is/are an acid halide as demonstrated in example 15.

Also, functionalities of the electron transfer and energy donor type can be linked to the energy acceptor part by an acylation reaction as demonstrated in examples 2, 3 and 8; by nucleophillic substitution as demonstrated in examples 4, 5, 6, 7, 9, 10, 12 and 17; by a carbanion mechanism as demonstrated in example 11; by a Grignard reaction as demonstrated in example 14, by a tosylate mechanism as demonstrated in example 13, or by a Wittig reaction as demonstrated in example 16. Similar reaction pathways can be used to link chemiluminescent molecules to energy donor molecules. The list of examples of reaction pathways is intended to be examplary and other pathways can be devised by one skilled in the art. Furthermore, only a representative number of luminides are shown and a vast number of other novel luminides can be made by one skilled in the art following the guidelines herein disclosed.

And, the disclosed exemplary luminides, and components: chemiluminescent molecules, photochromic molecules, energy transfer molecules, and drug molecules can be modified to further candidate components by addition of functional groups by one skilled in the art. Representative groups include aklyl, cycloalkl, alkoxycarbonyl, cyano, carbamoyl, heterocyclic rings containing C, O, N, S, sulfo, sulfamoyl, alkoxysulfonyl, phosphono, hydroxyl, halogen, alkoxy, alkylthiol, acyloxy, aryl, alkenyl, aliphatic, acyl, carboxyl, amino, cyanoalkoxy, diazonium, carboxyalkylcarboxamido, alkenyl, thio, cyanoalkoxycarbonyl, carbamoylalkoxycarbonyl, alkoxy carbonylamino, cyanoalkylamino, alkoxycarbonylalkylamino, sulfoalkylamino, alkylsulfamoylaklylamino, oxido, hydroxy alkyl, carboxy alkylcarbonyloxy, cyanoalkyl, carbonyloxy, carboxyalkylthio, arylamino, heteroarylamino, alkoxycarbonyl, alkylcarbonyloxy, carbomoylalkoxy, cyanoalkoxy, alkoxycarbonylalkoxy, carbamoylalkoxy, carbamoylalkyl carbonyloxy, sulfoalkoxy, nitro, alkoxyaryl, halogenaryl, amino aryl, alkylaminoaryl, tolyl, alkenylaryl, allylaryl, alkenyloxyaryl, allyloxyaryl, allyloxyaryl, cyanoaryl, carbamoylaryl, carboxyaryl, alkoxycarbonylaryl, alkylcarbonyoxyaryl, sulfoaryl, alkoxysulfoaryl, sulfamoylaryl, and nitroaryl.

EXPERIMENTAL SECTION I

Synthesis

Synthesis of MTL 7-3, and MTL J-1

Step A: Preparation of p-N,N-dimethylaminobenzoyl chloride

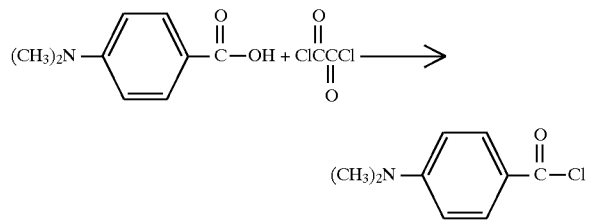

In a round bottom flask fitted with a reflux condenser is placed 4 g of p-dimethylaminobenzoic acid and 8 ml of oxalylchloride. The evolution of gas starts immediately and the spontaneous reaction is run at room temperature for 15 minutes. 8 ml of toluene is added and and the mixture is heated to gentle reflux for one hour. The reaction mixture is then distilled to dryness under reduced pressure to produce a blue-green solid which is washed with ether and dried on a watch glass.

Step B: Preparation of p-dimethylaminobenzanilide

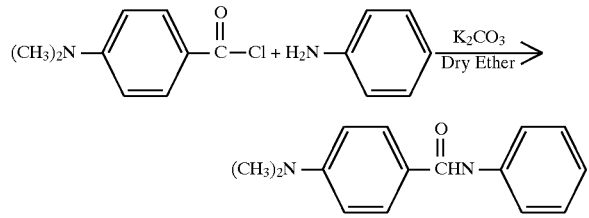

A solution of 0.95 g of aniline in 10 ml of dry ether containing 2.2 g of $K_2CO_3$ was heated to reflux temperature. To the refluxing mixture 2 g of p-dimethylaminobenzoyl chloride was added as a powder slowly through the condenser port. The reaction was refluxed for 1.5 hours and the ether distilled off. Cold water was added to the residue and the p-dimethylaminobenzanilide collected by filtration. Yield 1.51 g orange-red powder. Anilide functionality confirmed by IR.

Step C: Preparation of p-N,N dimethyl-p-N-ethyl-N-2-chloroethylbenzophenone.

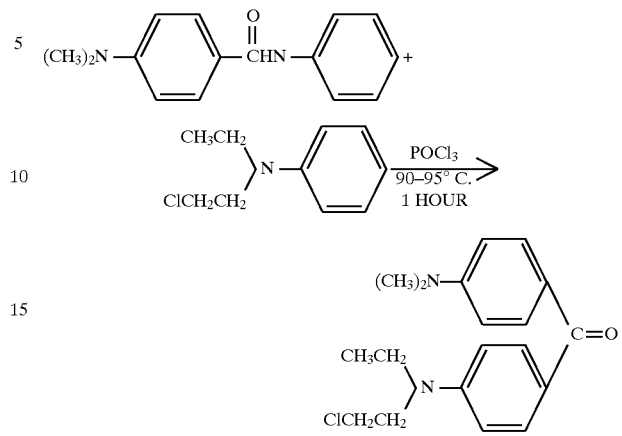

1.5 g of dry, powdered p-dimethylbenzanilide, 2.4 g of N-ethyl-N-2-chloroethylaniline, and 1.3 ml of phosphorus oxychloride were mixed in a 25 ml 2-necked flask, fitted with a thermometer immersed in the reaction mixture and a reflux condenser having a $CaCl_2$ drying tube on top. The reaction was warmed slowly until an exothermic reaction occured. The temperature was maintained at less than 100° C. by periodic immersion of the flask in ice water. The reaction was then maintained at 95 C. for one hour to yield a dark green liquid. The reaction mixture was then hydrolyzed in a 150 ml beaker with the addition of a solution of 1.36 ml of concentrated HCl to 10.4 ml of distilled $H_2O$. The beaker was covered with a watch glass and heated on a hot water bath for 1.5 hours to yield a green-yellow solution. 10:1 cold water was added to the hydrolyzed mixture to form a brilliant purple solution which was filtered. The filtered product was dissolved in a minimum volume of ethanol, and twice the volume of cold $H_2O$ was added. The ketone was then extracted in an equal volume of chloroform which was removed by distillation to dryness under reduced pressure. Brilliant purple solid product. Ketone confirmed by IR and NMR.

Step D: Preparation of 1-(4-N,N-dimethylaminophenyl)-1-(4-N-ethyl-N-2-chloroethylphenyl) ethylene.

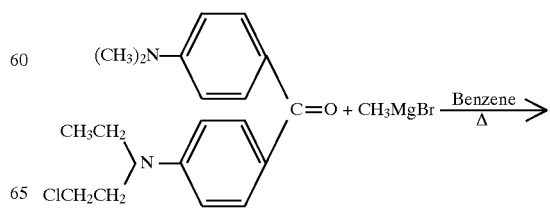

-continued

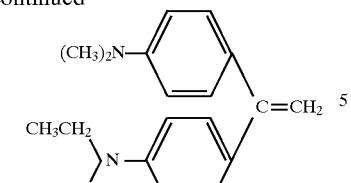

One ml of a 3 molar etherial solution of magnesium bromide was evaporated almost to dryness under reduced pressure in a 50 ml three necked flask equipped with a thermometer and nitrogen sparger. The grey moist solution was suspended in 1.3 ml of dry benzene. The flask was then equipped for refluxing by the addition of a condenser fitted with a $CaCl_2$ drying tube and an addition funnel. 0.017 moles of the ketone dissolved in 4.4 ml of boiling benzene was then placed in an addition funnel and added dropwise to the warmed methyl magnesium bromide-benzene slurry over a half hour period. The resulting solution was refluxed for one hour. The completion of the reaction was evident by the color change of the solution from brilliant purple to blue. The reaction mixture was cooled to room temperature, and 0.785 ml of saturated $NH_4Cl$ was cautiously added. Additional NH 4Cl was added until two layers were apparent with the blue alcohol product in the bottom $H_2O$ layer. $1.7 \times 10^{-3}$ g of p-toluenesulphonic acid was added, and the solution was boiled on a water bath with the addition of benzene until the evaporation of $H_2O$ was complete and only the benzene layer remained. The acid contained in the reaction mixture was then removed by the addition of $0.73 \times 10^{-3}$ g of sodium bicarbonate. The solvent was reduced to dryness under reduced pressure to yield light blue crystals.

Step E: Preparation of a perchlorate of 1,5-di-(p-N-2-chloroethyl-N-ethylaminophenyl)-1,5-bis-(p-N,N-dimethylaniline)-1,3-pentadiene.

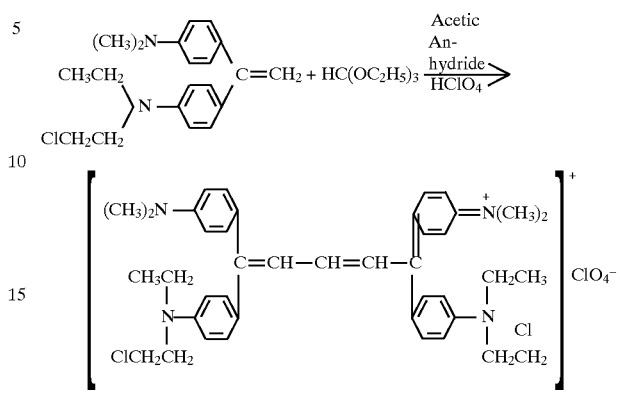

A mixture of $8.7 \times 10^{-4}$ moles of 1-(4-N,N-dimethylaminophenyl)-1-(4-N-2-chloroethyl-N-ethylaminophenyl)ethylene, 0.13 ml of ethyl orthoformate, and 0.39 ml of acetic anhydride was treated with a solution of 0.035 ml of 72 percent perchloric acid and 0.35 ml of acetic acid previously cooled to 0° C. The resulting mixture was allowed to stand at room temperature for 8 days, after which time it was treated with 0.22 ml of ether and kept an additional day at room temperature. The condensation product was washed with acetic acid, ethanol, and ether. The pale blue-green crystals were dissolved in a minimum volume of warm dry ethanol. The solution was centrifuged to pellet a white precipitate. The dark blue supernatant solution was removed and distilled to dryness under reduced pressure. The blue crystals where placed on watch glass and placed in the dark. The structure of the condensation compound was confirmed by IR and NMR.

Step F: Preparation of 1,5-di-(p-N-2-(N-(4-aminobutyl)-N-ethyl isolminol)-N-ethylaminophenyl)-1,5-bis-(p-N,N-dimethylaniline)-1,3-pentadiene.

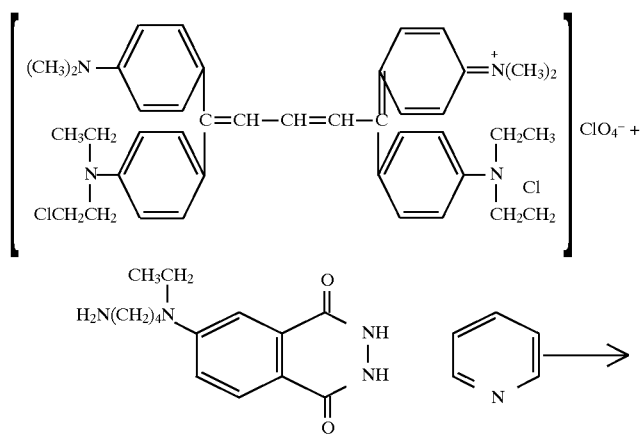

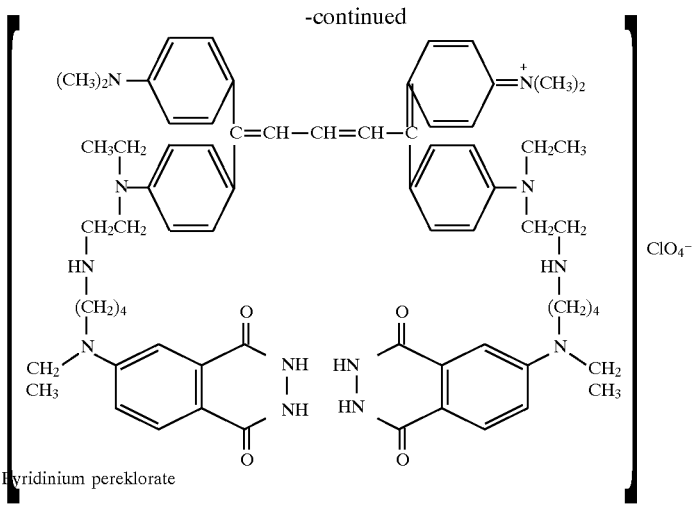

pyridinium pereklorate 5 mg (1.8 ×10 moles) of N-(4-aminobutyl)-N-isoluminol was suspended in 0.1 ml of pyridine small test tube. 30 mg (3.6 ×10 5 moles) of the pentadiene was dissolved in 0.5 ml of pyridine and 0.25 5 ml of DMSO. This latter solution was added dropwise to the former while vigorously stirring at room temperature initially then with intermittant imersion in a water bath at 35 ° C. The isoluminol which was only slightly soluble in pyridine went into solution as the reaction progressed. The reaction mixture was stirred and intermittantly immersed in the water bath at 35 C. until the reaction was complete. This reaction and all subsequent reactions were protected from direct light.

Step G: Preparation of Luminide, MTL 7–3 (2,6-di-(p-N-2-(N-(4-aminobutyl)-N-ethylisoluminol)-N-ethylaminophenyl)-2,6-bis-(p-N,N-dimethylanilino)-3,5-hexadinenitrile).

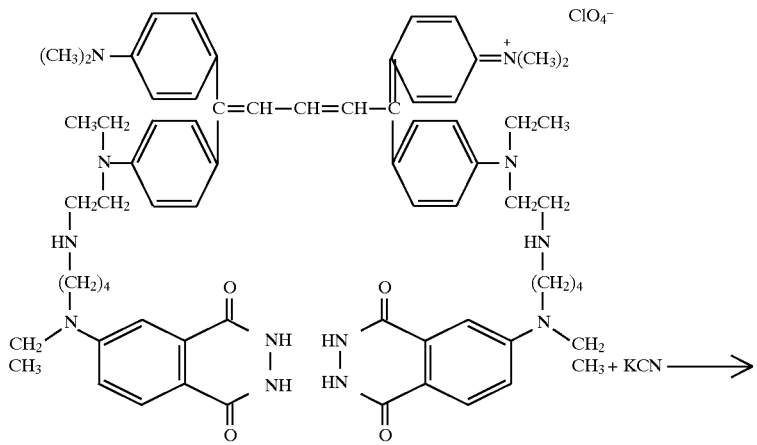

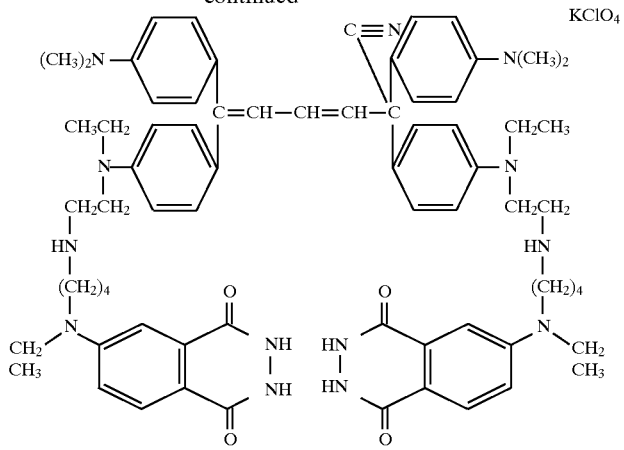

5 mg of solid KCN and 1 ml of distilled $H_2O$ were added to the blue-grey solution of 1,5-di-(p-N-2-(N-(4-aminobutyl)-N-ethylisoluminol)-N-ethylaminophenyl)-1,5-bis-(p-N,N-dimethylanilino)-1,3-pentadiene in pyridine/DMSO solvent. The solution was acidified by addition of sulphuric acid and the evolving HCN gas was removed by evaporating the solvent to dryness under reduced pressure. The pale green crystals were redissolved in DMSO to yield a pale green liquid. IR and NMR confirmed the structure.

Step H: Preparation of Luminide MTL J-1

(5-phosphonoformate-1,5-di-(p-N-2-(N-(4-aminobutyl)-N-ethylisoluminol)-N-ethylaminophenyl)-1,5-bis-(p-N,N-dimethylaniline)-1,3-pentadiene).

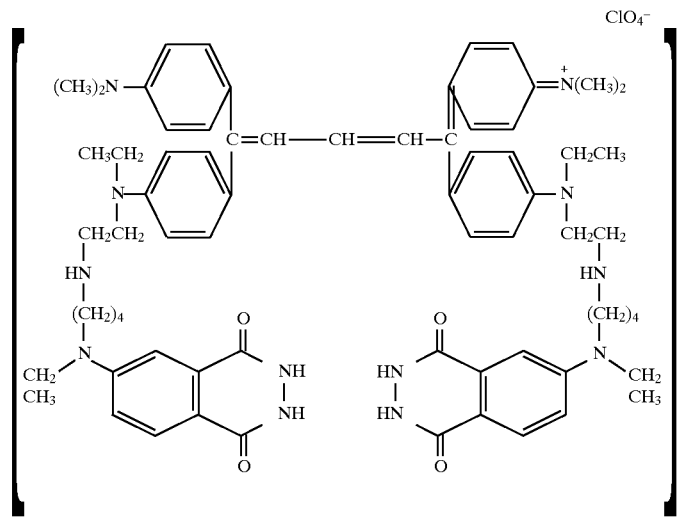

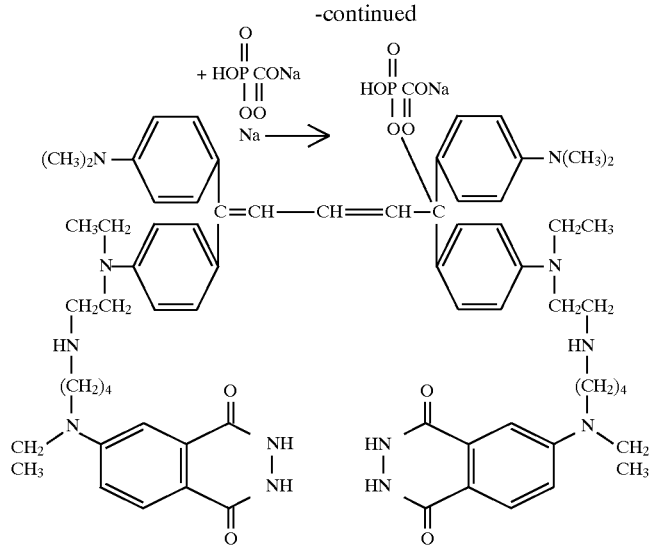

MTL J-1 was prepared by the equimolar addition of disodium phosphonoformate dissolved in $H_2O$ to a DMSO solution of 1,5-di-(p-N-2-(N-(4-aminobutyl)-N-ethylisoluminol)-N-ethylaminophenyl)-1,5-bis(p-N,N-dimethylaniline)-1,3-pentadiene such that the final solvent was 4:3 DMSO/$H_2O$. The reaction mixture was protected from light, and the colorless reaction product solution was packaged in light protecting vials and refrigerated at 4 °C.

Methods of synthesis of triphenylmethane dyes appear in Appendix I.

Methods of synthesis of polymethine dyes appear in Appendix II.

Methods of synthesis of azo and diazopolymethine dyes appear in Appendix III and IV, respectively.

Methods of synthesis of quaternary ammonium salt poly methines appear in Appendix V.

Methods of synthesis of the intermediates, tetramethylortho carbonate and substituted ethylenes appear in Appendix VI.

Methods of synthesis of indoline based dyes appear in Appendix VII.

Methods of synthesis of dyes with more than one chromophore appear in Appendix VIII.

Methods of forming a leucocyanide appear in Appendix IX.

Further Exemplary Material

Example 1.

The compound shown as formula 6 is prepared as follows:

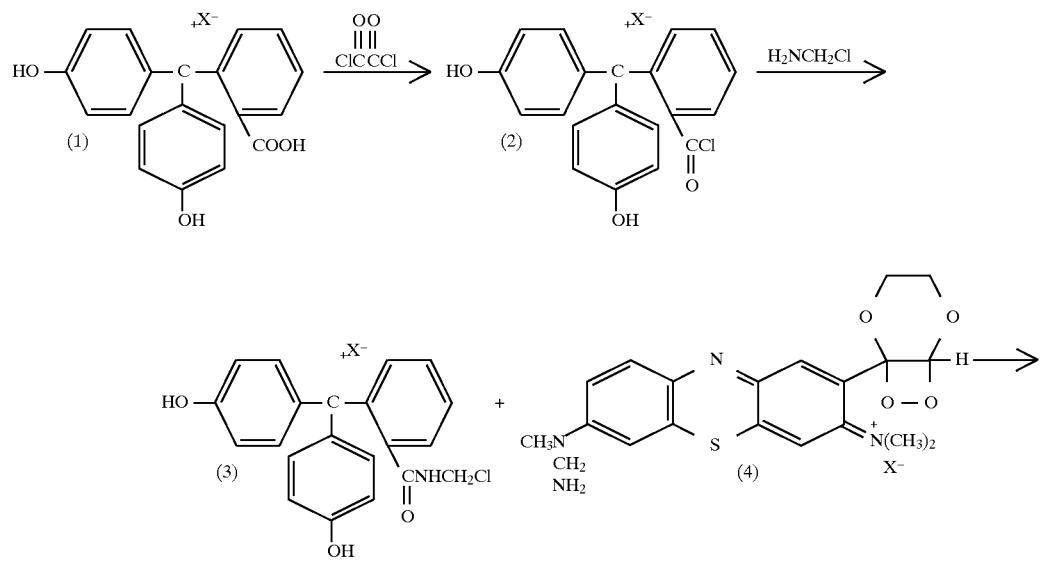

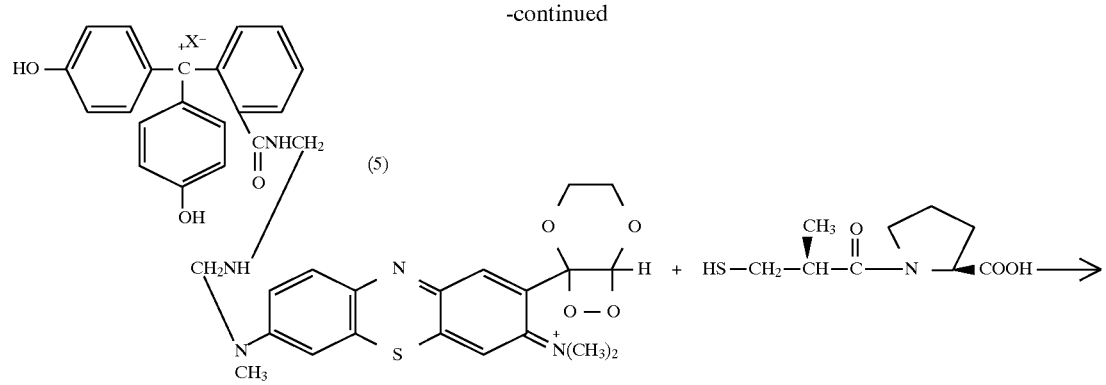

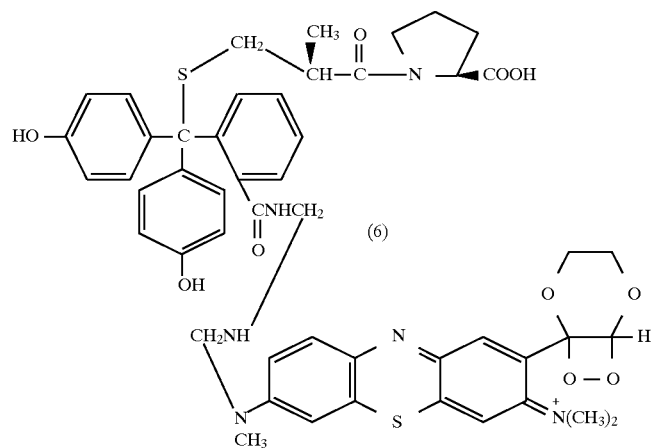

Phenolphthalein is converted to the corresponding acid chloride by treatment with oxalyl chloride. The acid chloride is reacted with chloromethylamine to form the corresponding amide which is in turn reacted with a dioxetan such as compound 4 to give adduct 5 where compound 4 is prepared from the appropriate starting dioxtene by a method described by Schaap. The adduct 5 is converted to the final product by treatment with Captopril.

Example 2.

The compound shown as formula 10 is prepared as follows:

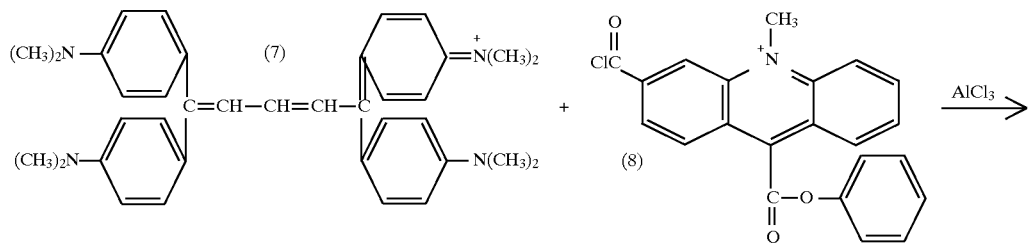

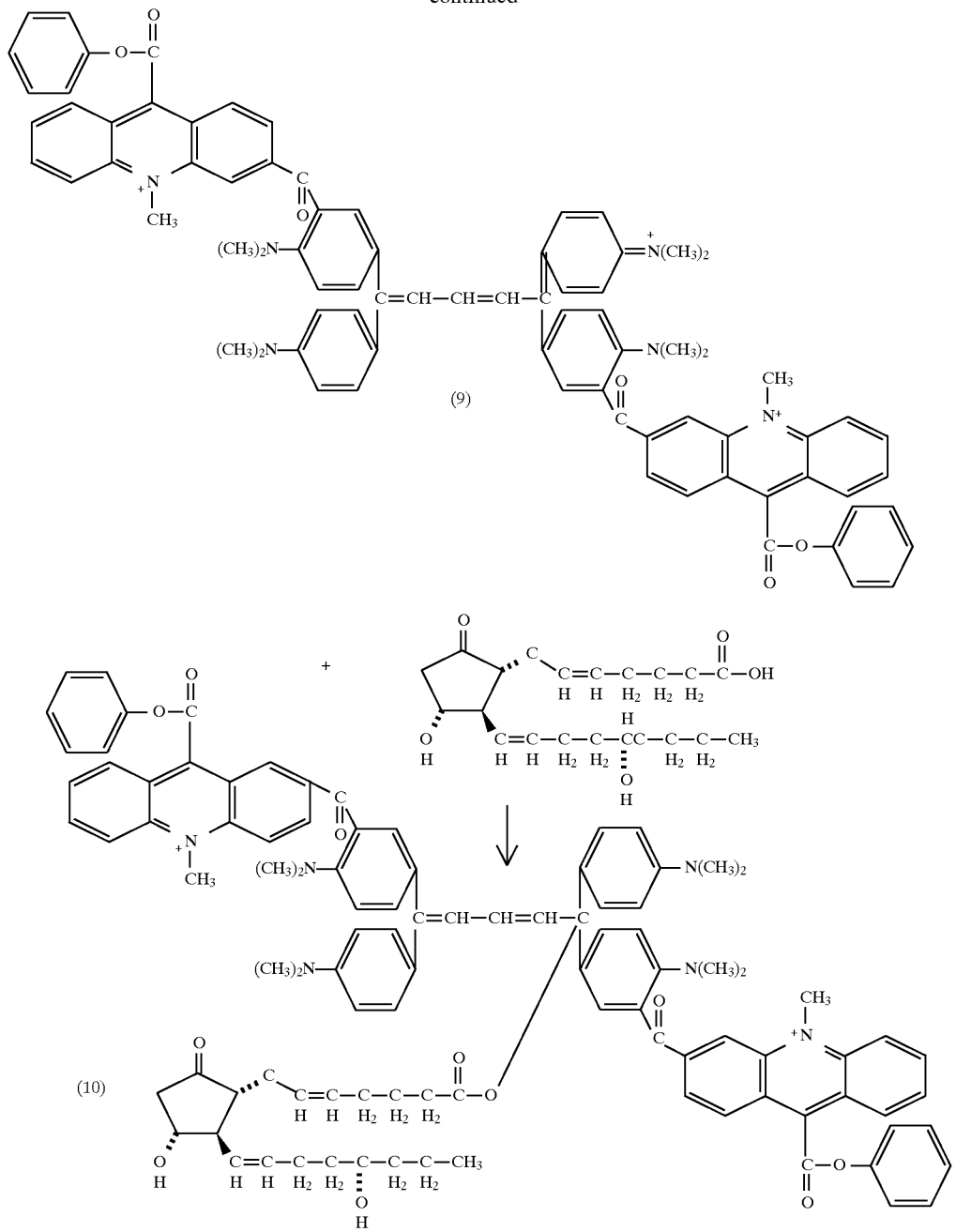
Compound 7 is acylated with an acridinium ester such as compound 8 to give adduct 9 which is treated with prostaglandin E₂ to give the final product 10.
Example 3.
The compound shown as formula 14 is prepared as follows:

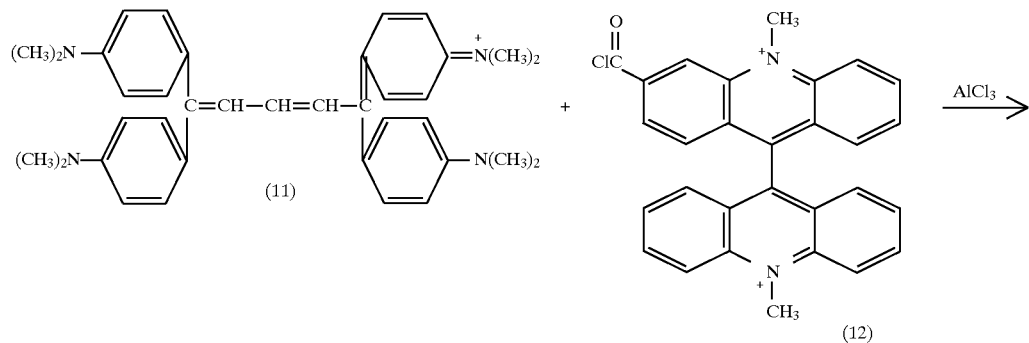
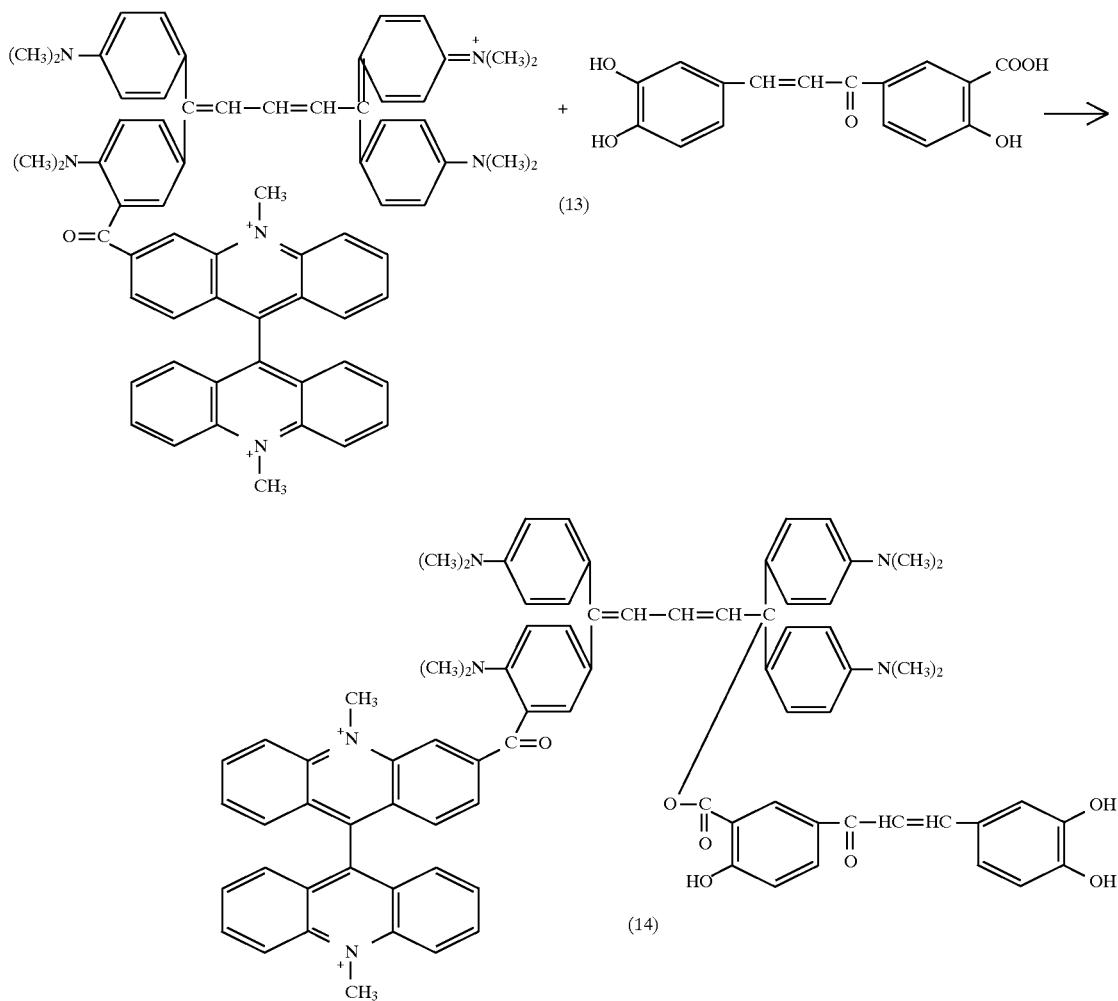
Compound 11 is acylated with a biacridinium derivative such as 12 to give adduct 13 which is treated with 5-(p-sulfamylphenylazo) salicylic acid to give the final product 14.
Example 4.
The compound shown as product 18 is prepared as follows:

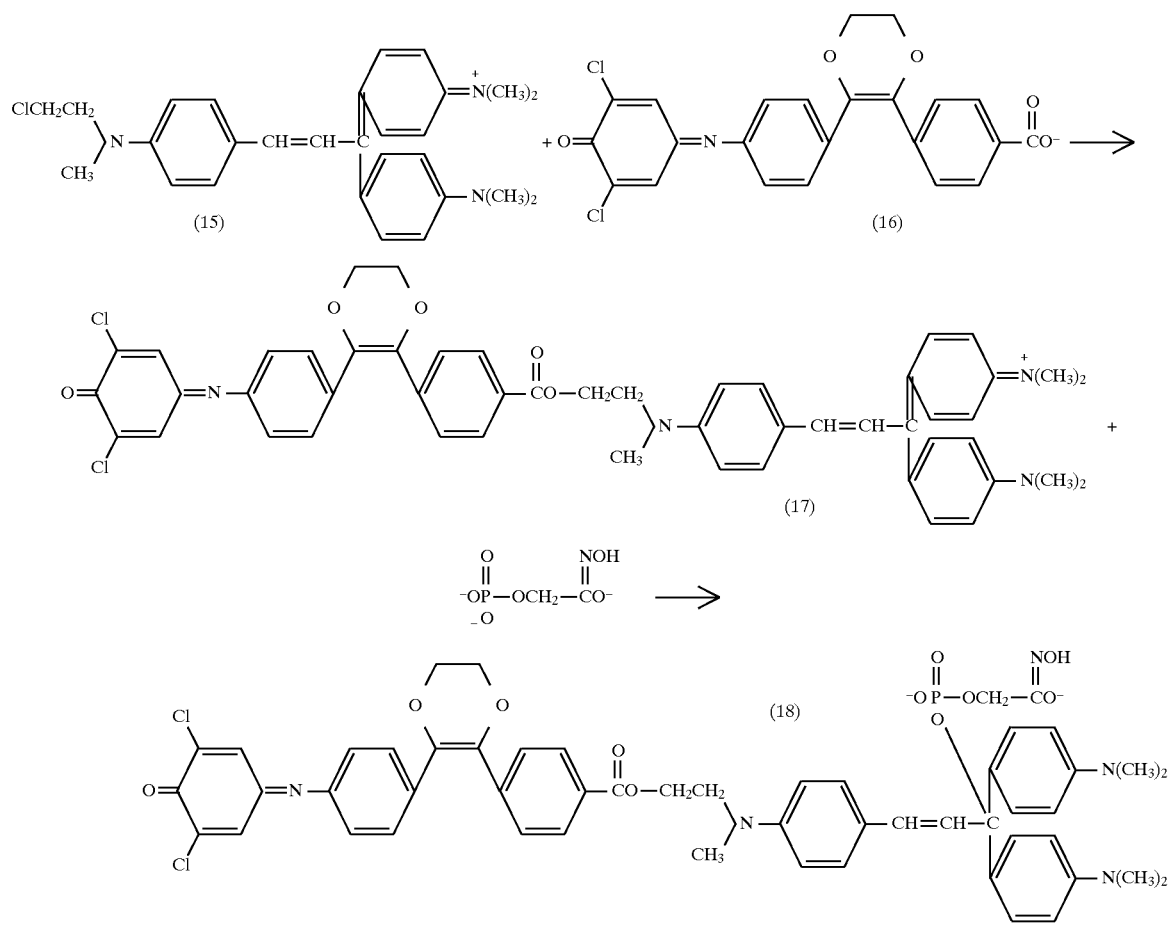
Compound 15 is reacted with the carboxylate 16 to form the ester 17 where 16 is formed by linking an oxidation reduction agent such as a derivative of 2,6-dichloro phenolindophenol with a dioxene carboxylate derivative. The ester 17 is reacted with p-glycolohydroxamate to give the final product.
Example 5.
The compound shown as formula 22 is prepared as follows:
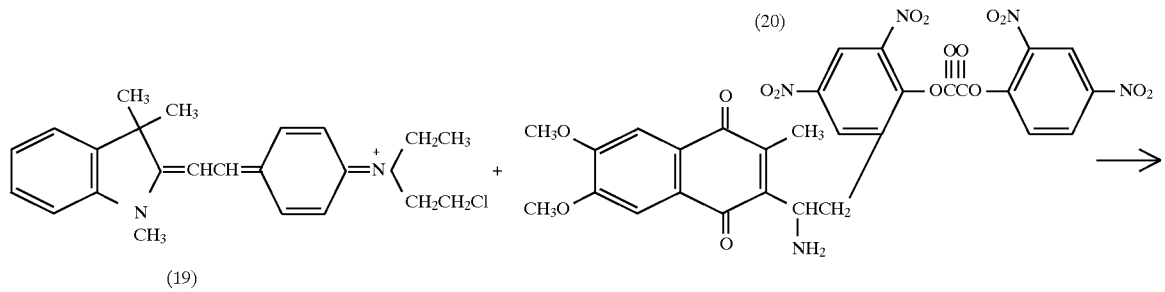

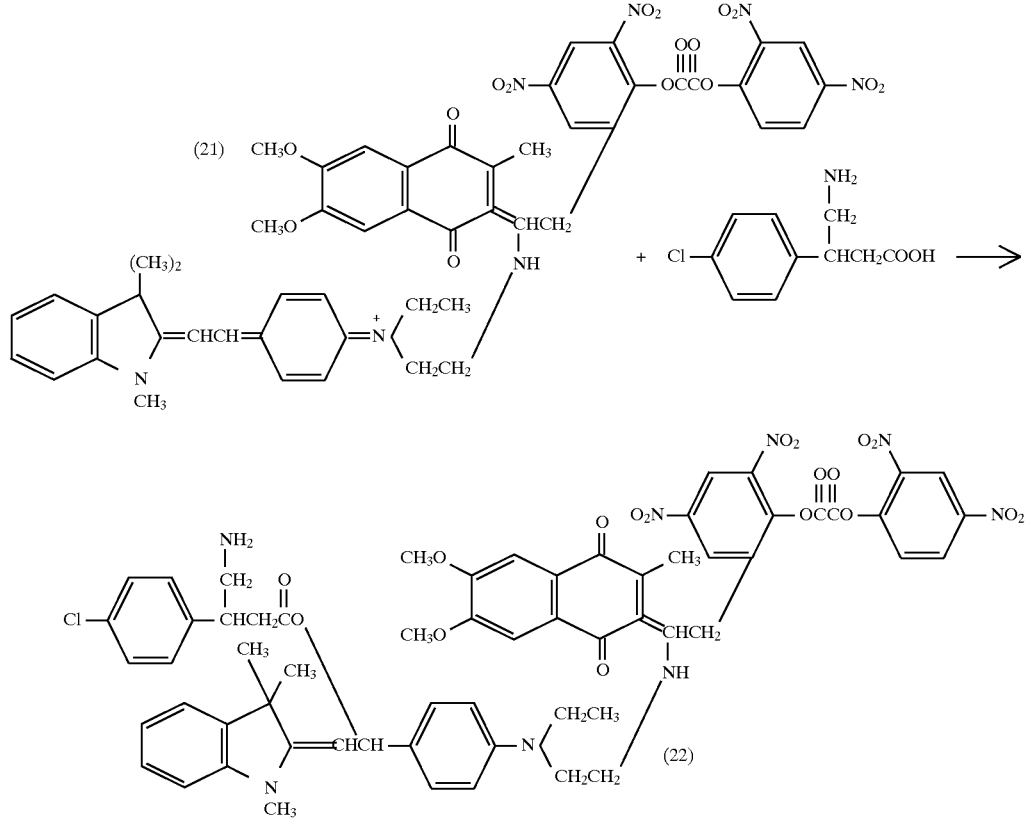

Compound 19 which is formed using an appropriately substituted aniline is reacted with adduct 20 to give adduct 21 where adduct 20 is formed by alkylation of the aromatic ring of an active oxalate derivative with a molecule which can accept electrons via electron transport. Adduct 21 is treated with Baclofen to form the product 22.

Example 6.

The compound shown as formula 26 is prepared as follows:

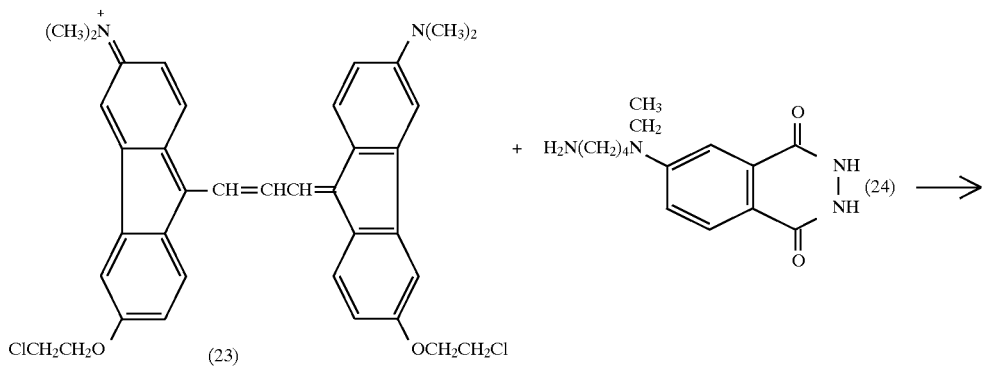

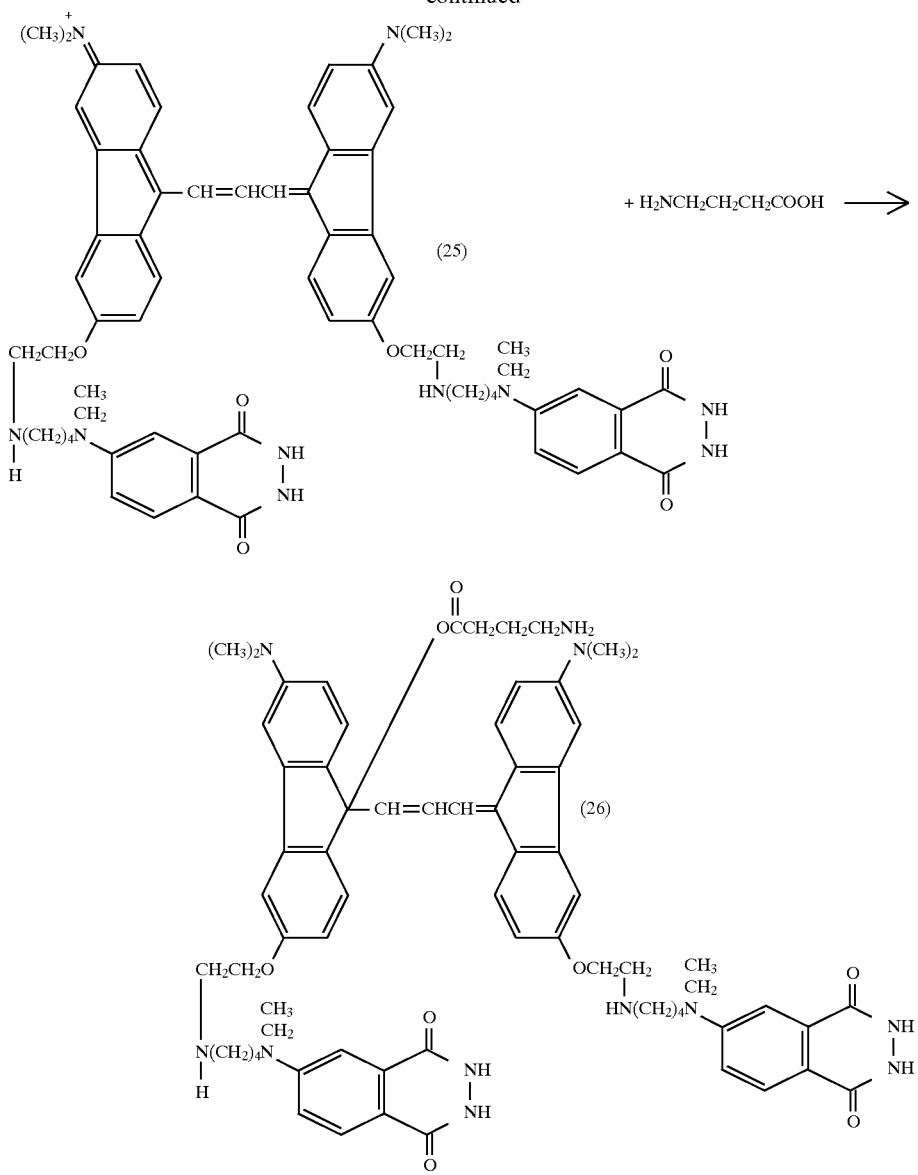
Compound 23 is prepared with the appropriately substituted ethoxy groups which is then reacted with a phthalhydrazide such as 24 to form adduct 25. The final product 26 is formed by treatment of adduct 25 with γ-aminobutyric acid.
Example 7.
The compound shown as formula 30 is prepared as follows:
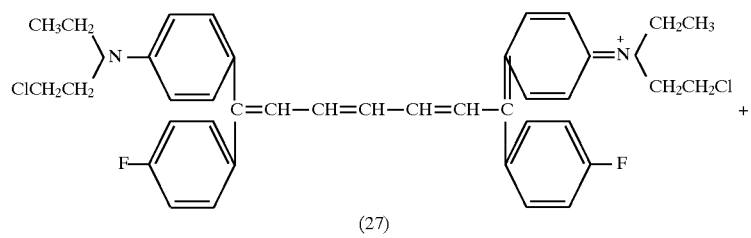

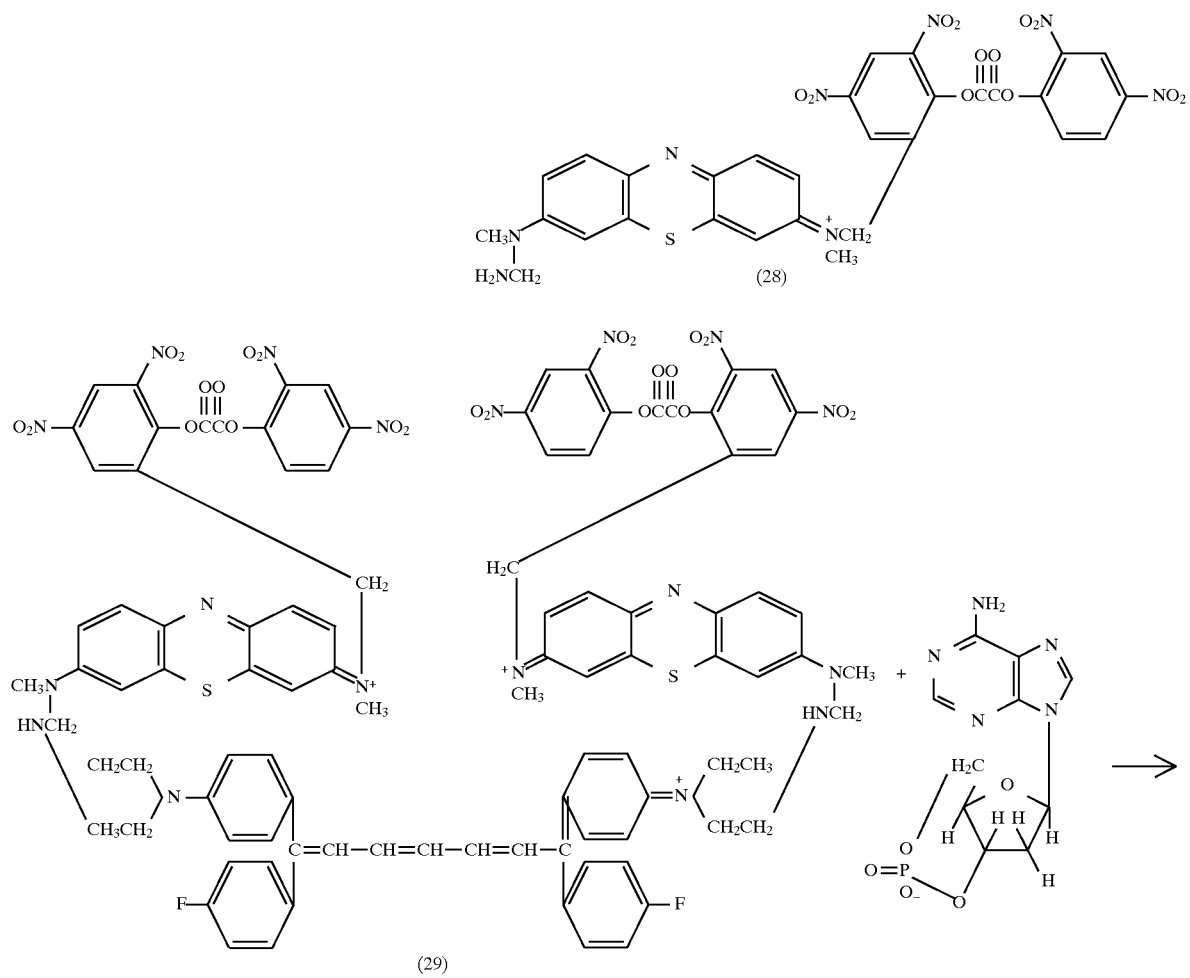

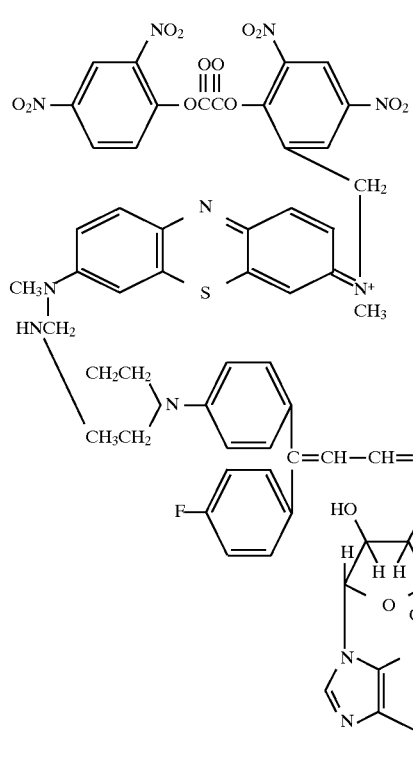
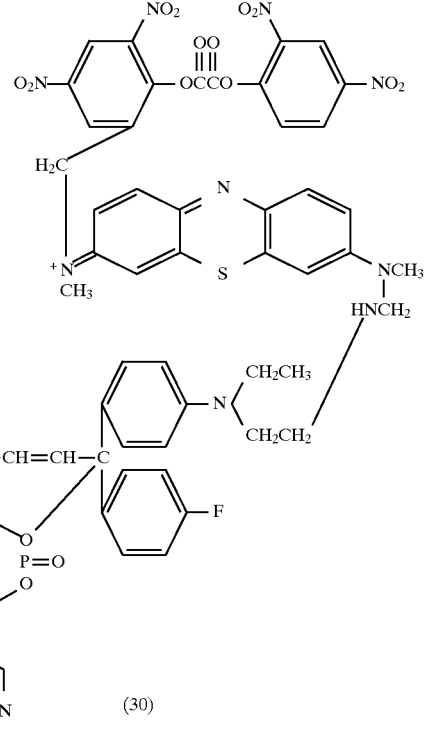
(30)
Compound 27 is reacted with adduct 28 which is formed by akylation of an active oxalate by a methylene blue derivative.
The product adduct 29 is treated with adenosine 3', 5'-cyclic monophosphate to yield the final product 30.
Example 8.
The compound shown as formula 34 is prepared as follows:

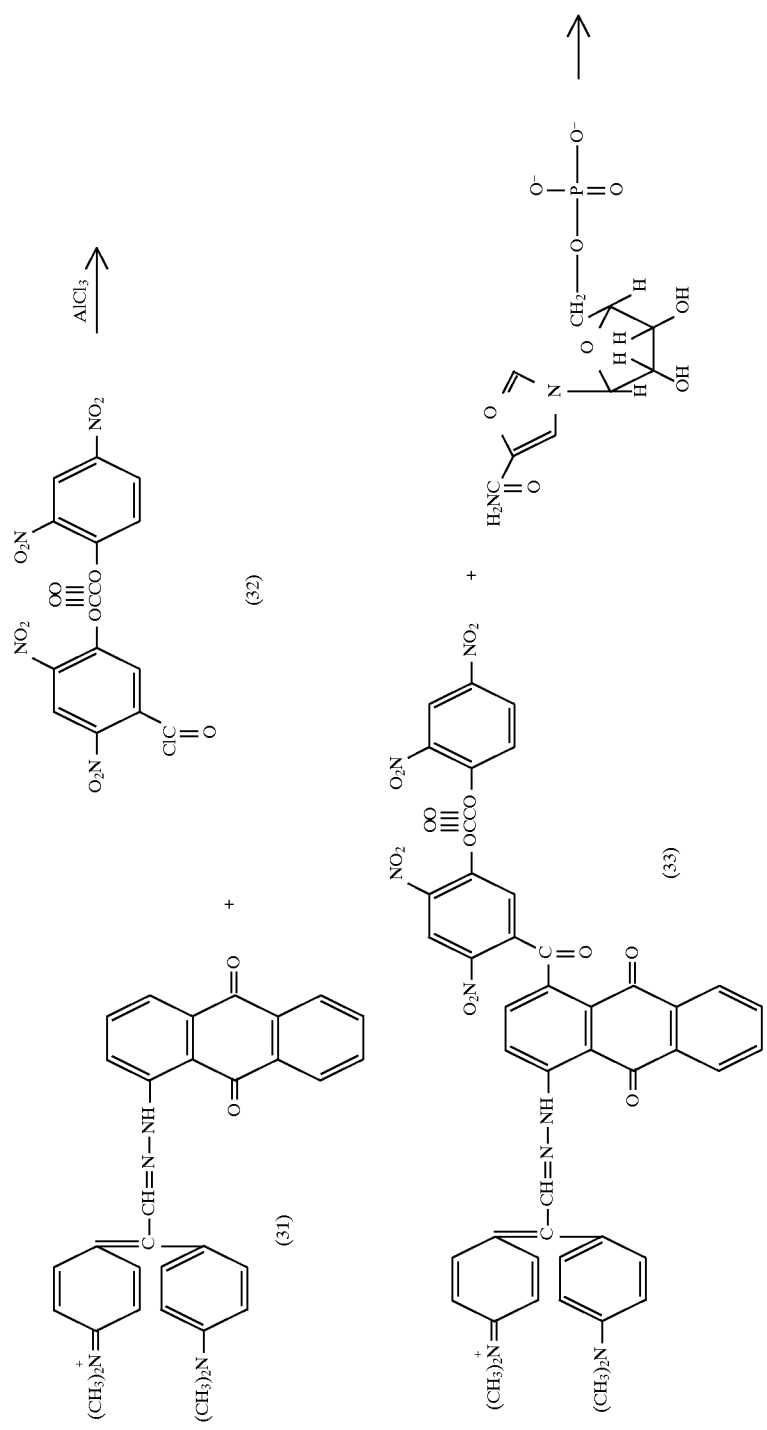

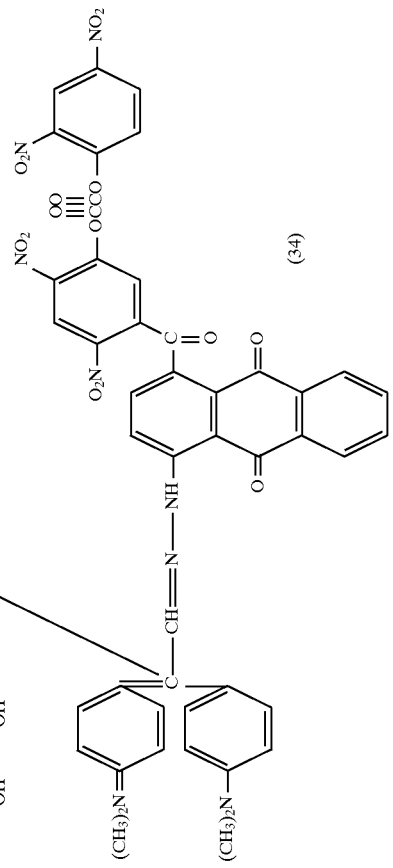
(34)

Compound 31 is acylated with an active oxalate such as 32 to yield adduct 33. Adduct 33 is treated with Ridavirin to yield the final product 34.

Example 9.

The compound shown as formula 38 is prepared as follows:

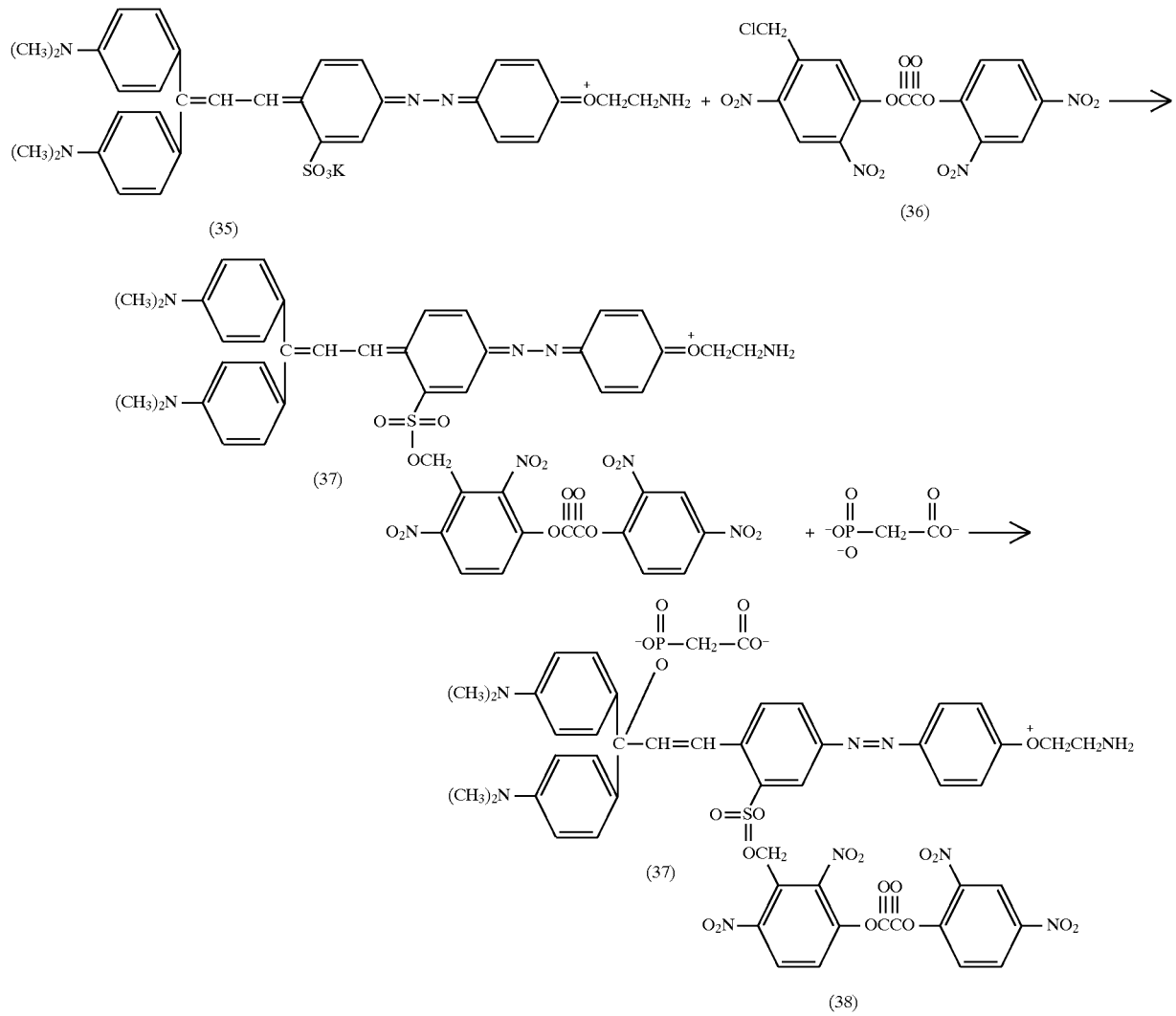

Compound 35 is reacted with an alkyl halide derivatived active oxalate such as 36 to give adduct 37 which is treated with phosphonoacetate to give the final product 38.

Example 10.

The compound shown as formula 42 is prepared as follows:

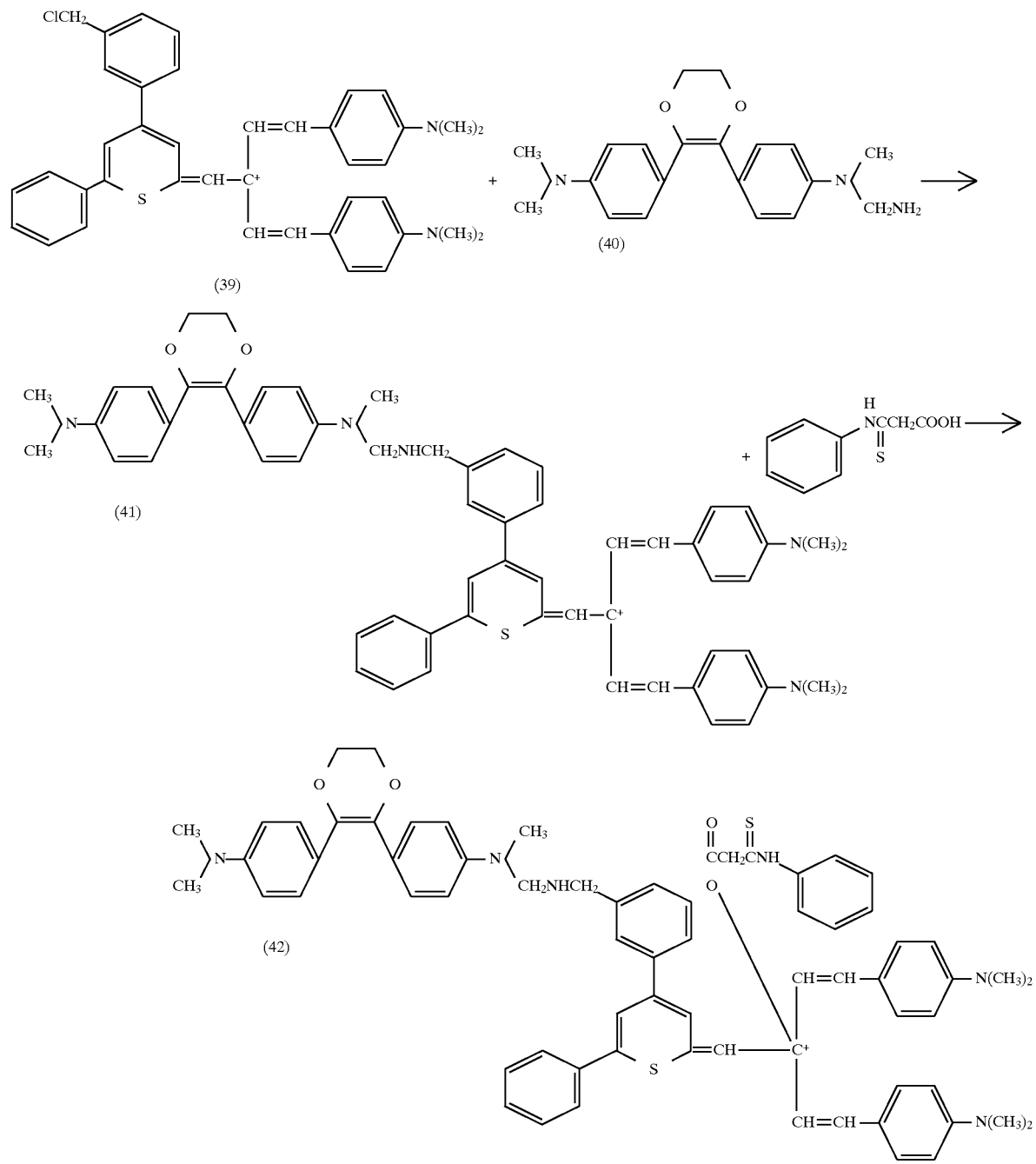
Compound 39 is prepared using the proper chloromethyl substituted benzene and reacted with a dioxene derivative such as 40 to yield adduct 41. Adduct 41 is treated with U-7130 to give the final product 42.
Example 11.
The compound shown as formula 47 is prepared as follows:

111 112
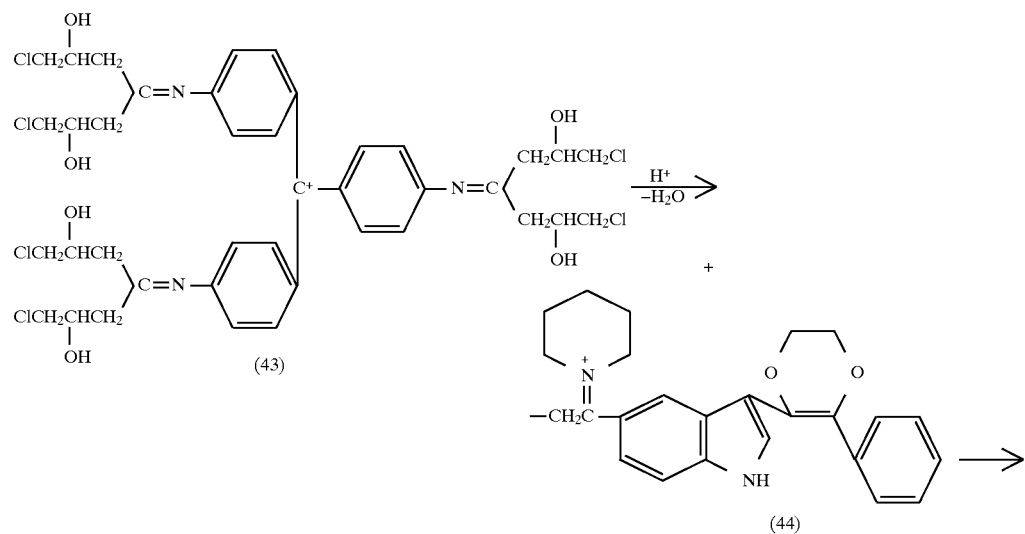
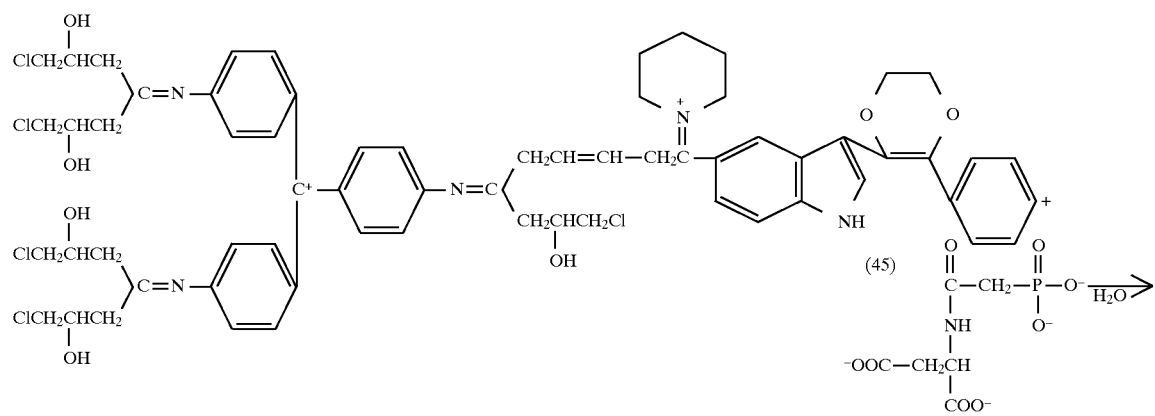
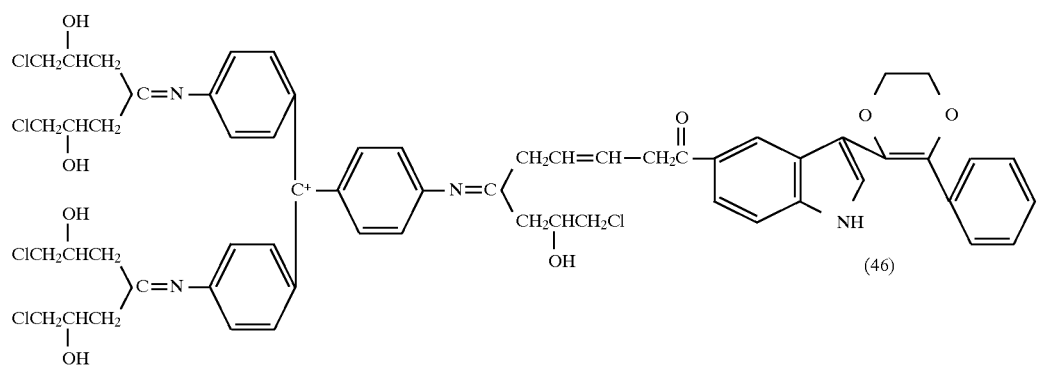

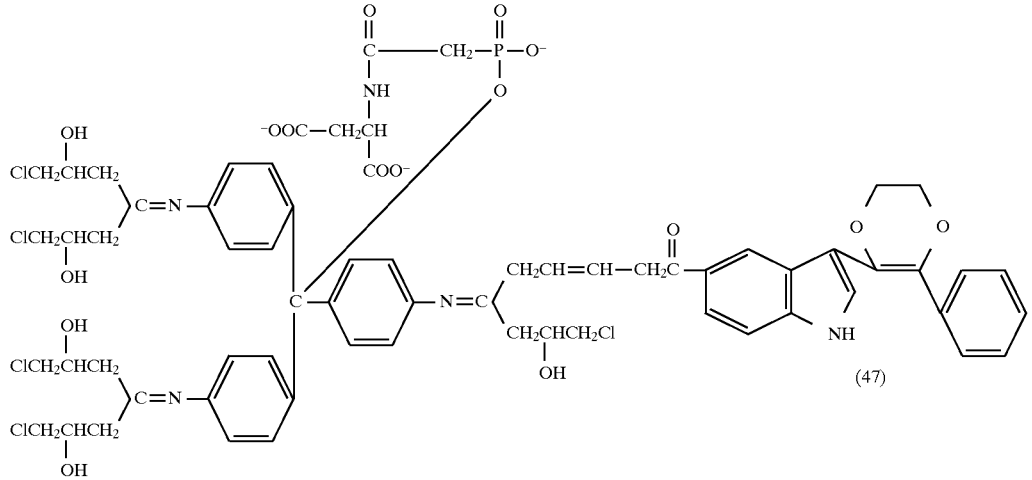
Compound 43 is dehydrated and treated with an indole ketone derivative dioxene such as 44 to give intermediate adduct 45 which is hydrolyzed to the ketone adduct 46. Adduct 46 is treated with N-(phosphonacetyl)-L-asparate to yield the final product 47.
Example 12.
The compound shown as formula 51 is prepared as follows:
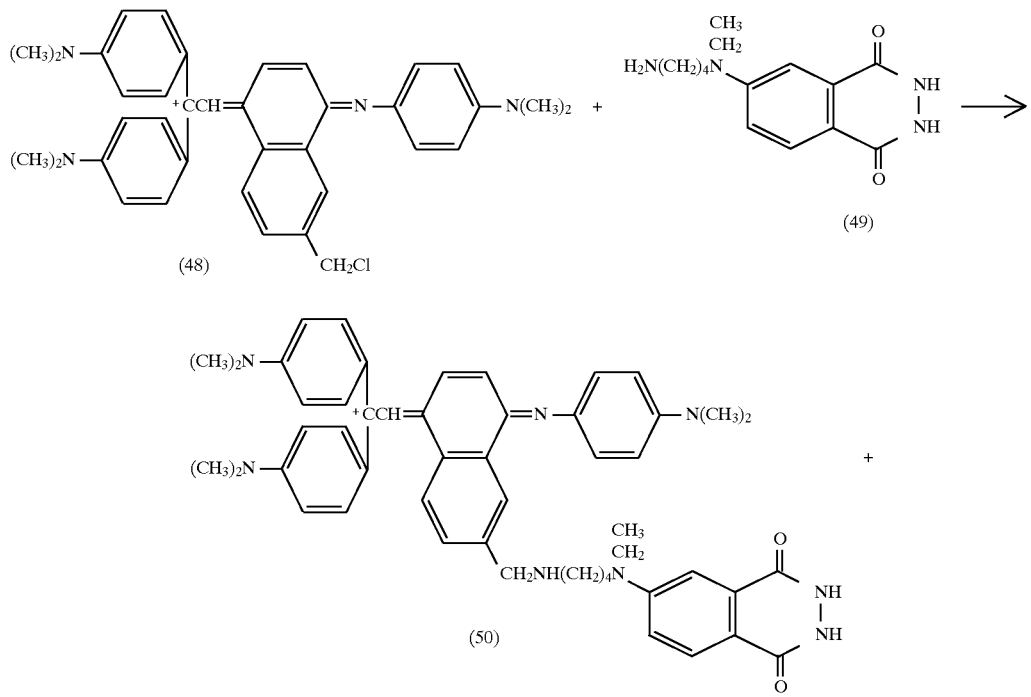

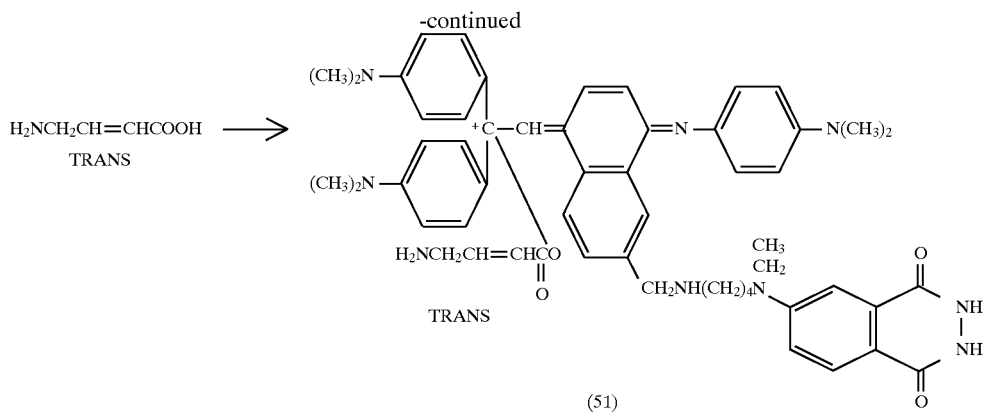
Compound 48 is prepared from the proper chloromethyl, naphthalene and reacted with a phthalhydrazide such as 49 to give adduct 50 which is reacted with trans-4-aminocrotonic acid to give the final product 51.
Example 13
The compound shown as formula 56 is prepared as follows:
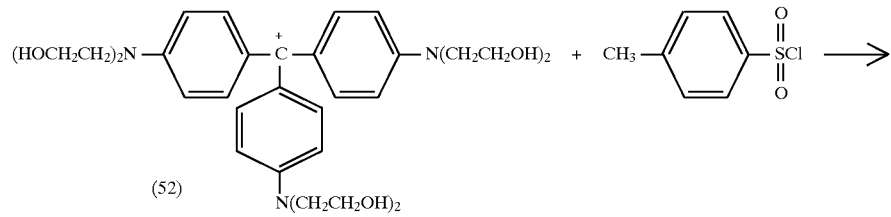
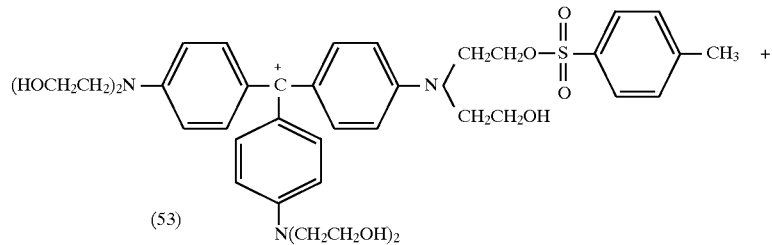
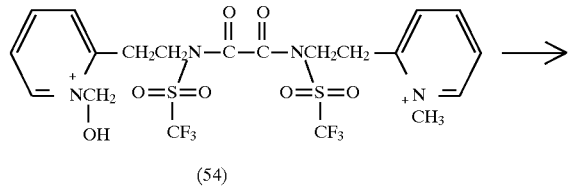
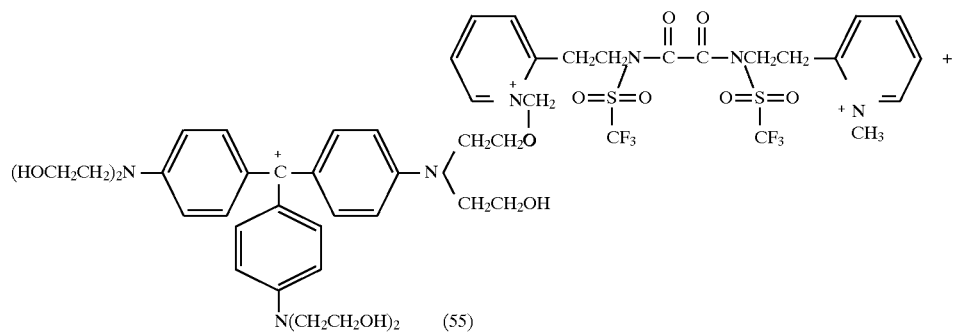

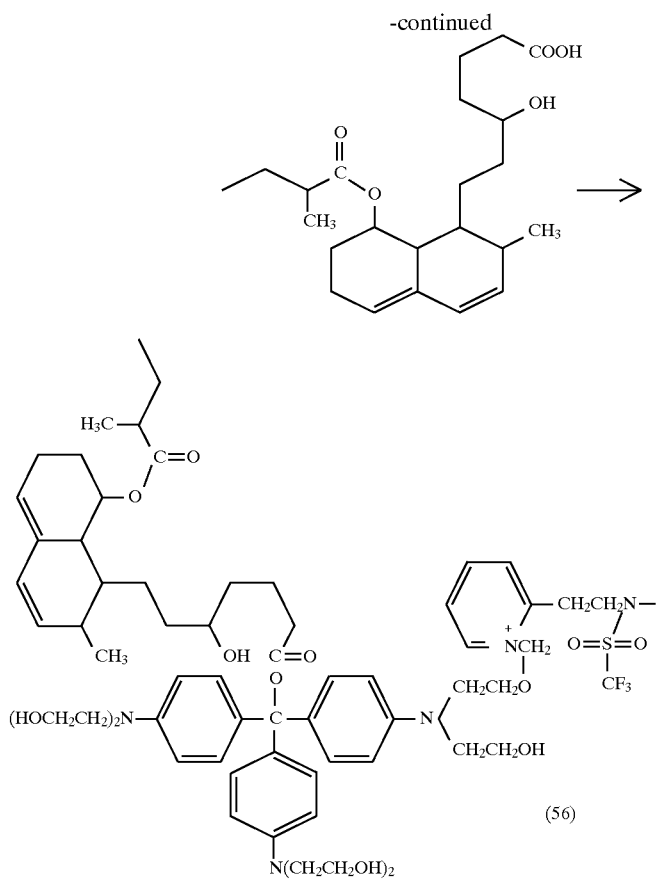

(56)

Compound 52 is reacted with p-toluene sulfonyl chloride to give tosylate adduct 52 which is reacted with an active oxamide that has an alcoholic function such as 54 to give ether adduct 55. The adduct 55 is reacted with compactin to give the final product 56.

Example 14.

The compound shown as formula 62 is prepared as

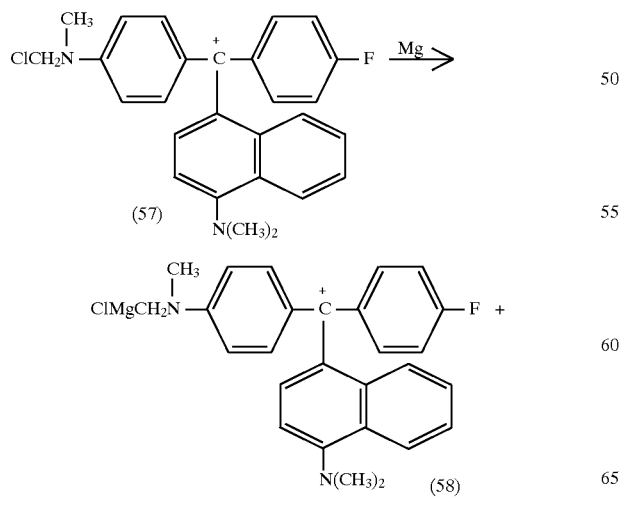

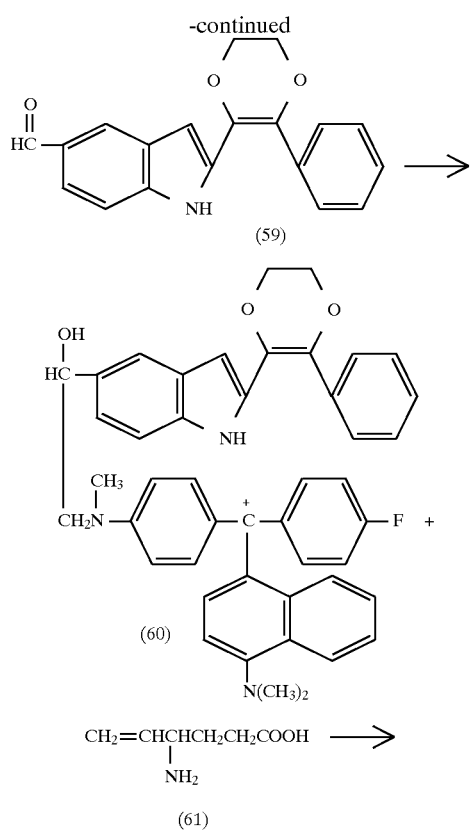

$CH_2=CHCHCH_2CH_2COOH \longrightarrow$
$\quad\quad\quad\quad |$
$\quad\quad\quad\quad NH_2$ (61)

119
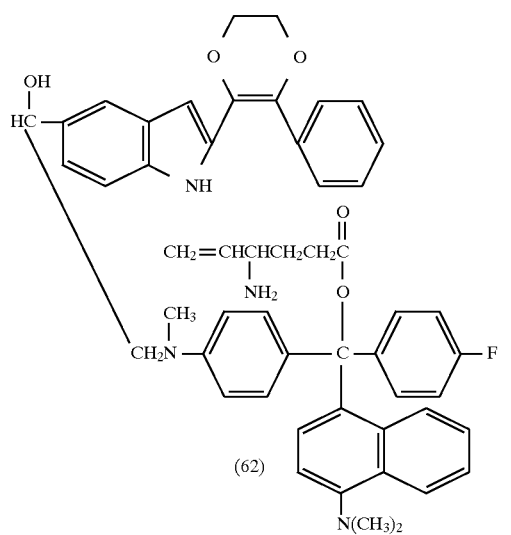
(62)
120
Compound 57 is reacted with Mg to form the Grignard reagent 58 which is reacted with a dioxene indole derivative with an aldehyde or ketone functionality such as 59 to give the alcohol 60. Adduct 60 is reacted with 4-amino-hex-5-enoic acid, 61, to give the final product 62.
Example 15.
The compound shown as formula 67 is prepared as follows:
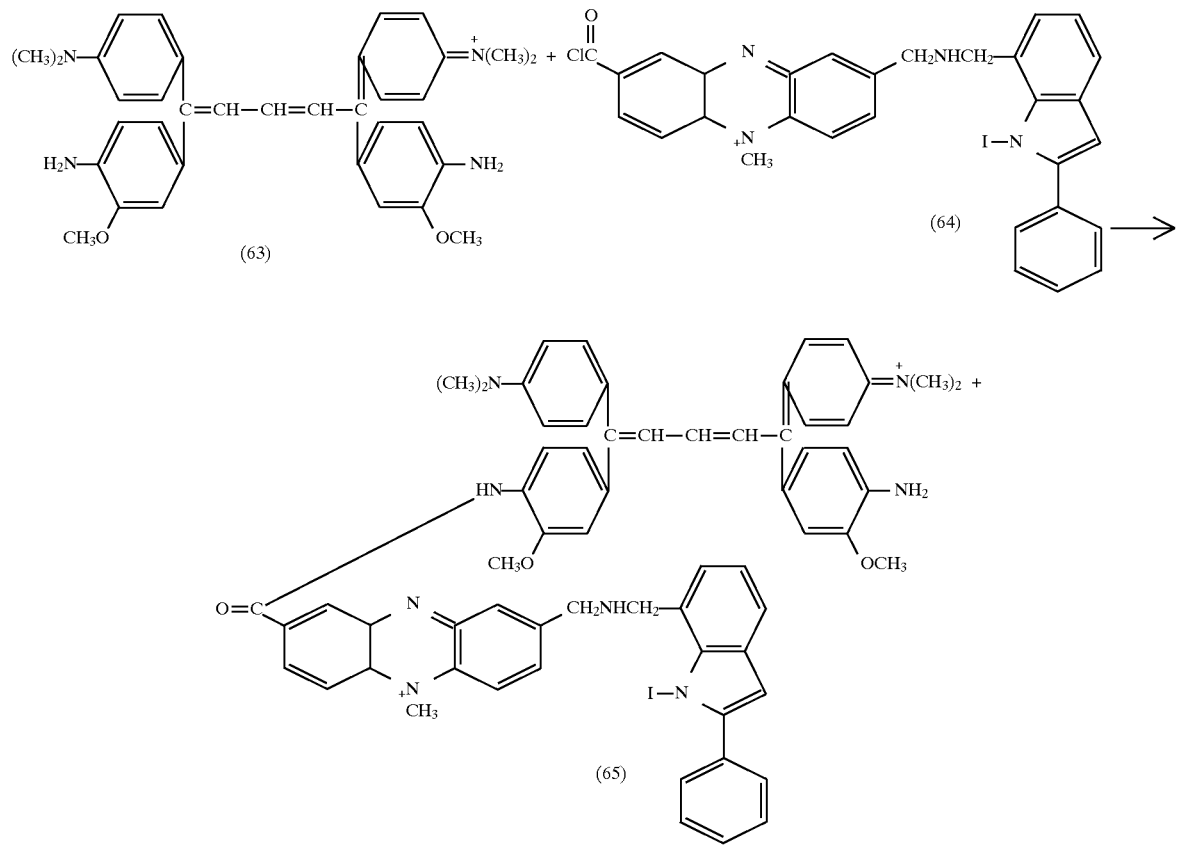

-continued

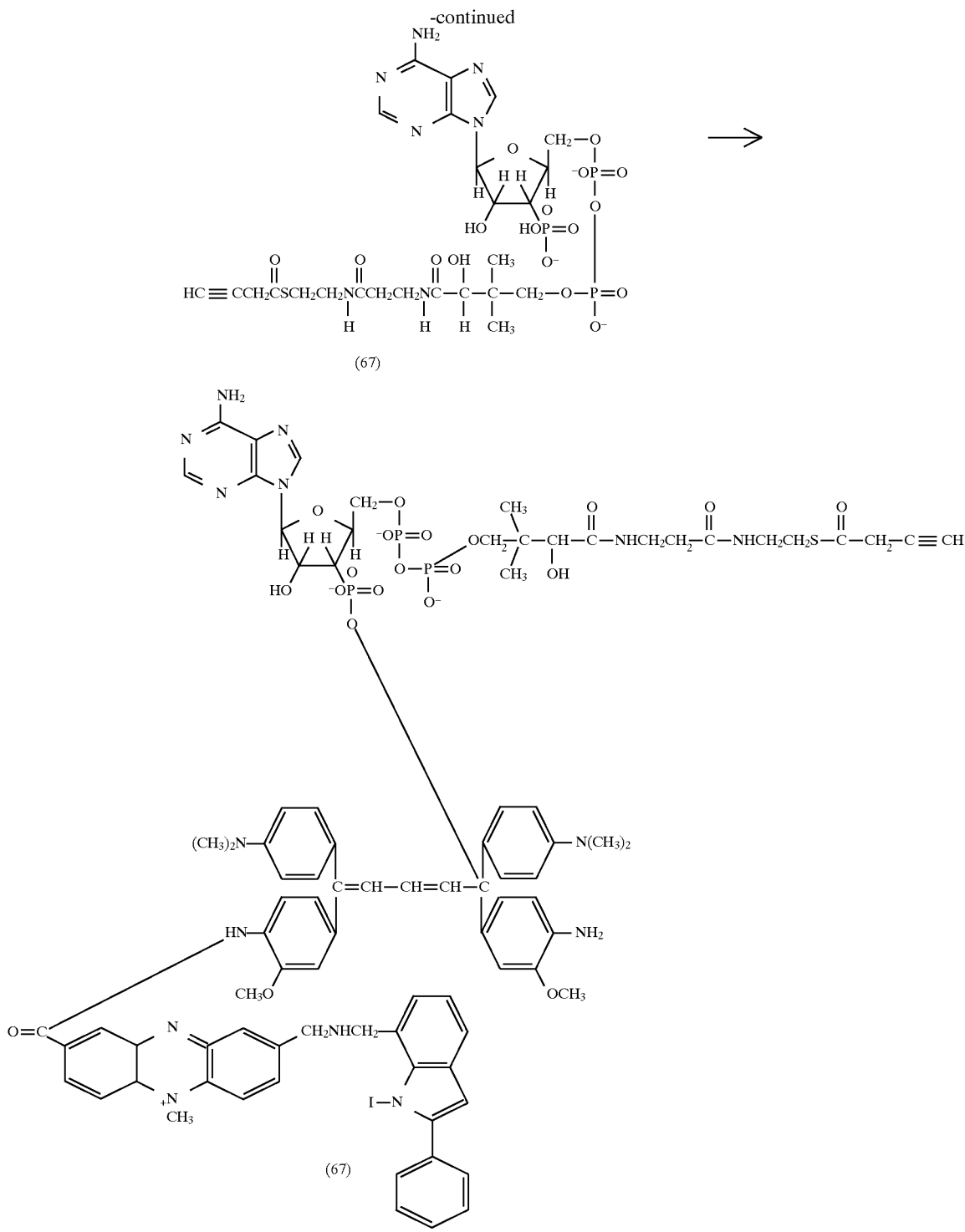

(67)

(67)

The compound 63 is reacted with an acid halide such as 64 to give adduct 65. The acid halide 64 is prepared from the corresponding acid by reaction with oxalyl chloride. The original acid is prepared by reacting a phenazine possessing an alkyl halide and a carboxylic acid function with an indole derivative that has a amino group. The adduct amide 65 is reacted with but-3-ynoyl-CoA, 66, to give the final product 67.

Example 16.

The compound shown as formula 71 is prepared as follows:

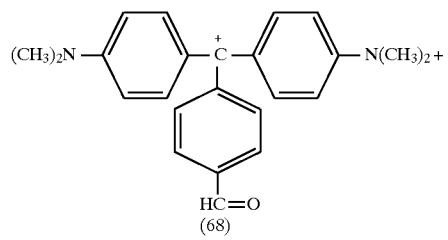

(68)

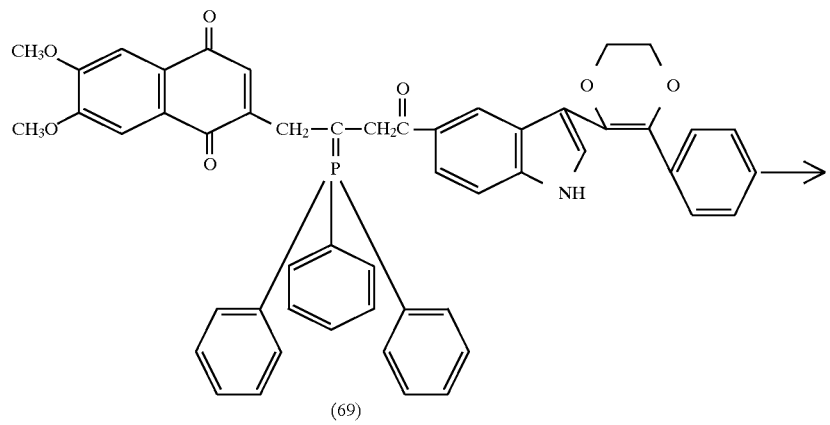

(69)

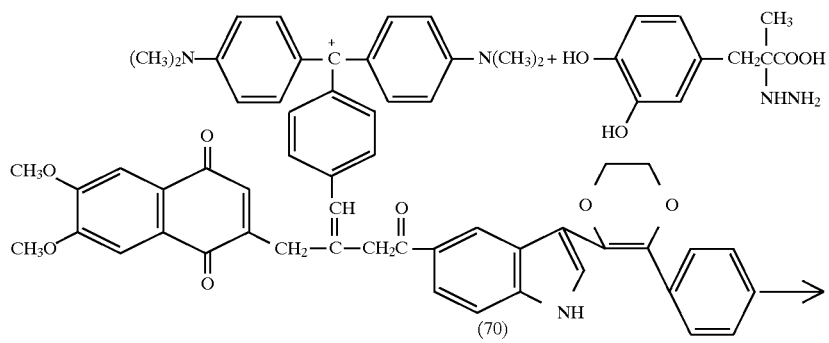

(70)

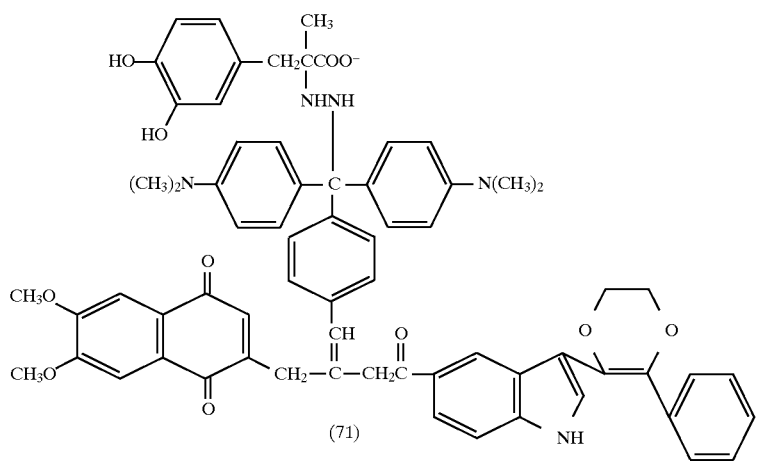

(71)

The aldehyde compound 68 is reacted with a phosphonium ylid of a ubiquinone nucleus linked to a indole dioxene derivative such as 69 to form adduct ethylene 70. (The ylid 69 is formed by an acylation reaction of an indole derivative dioxene with a ubiquinone adduct followed by reaction with triphenylphosphine.) The adduct 70 is reacted with DL-2-hydrazino-α-methyldopa to form the final product 71.

Example 17.

The compound shown as formula 76 is prepared as follows:

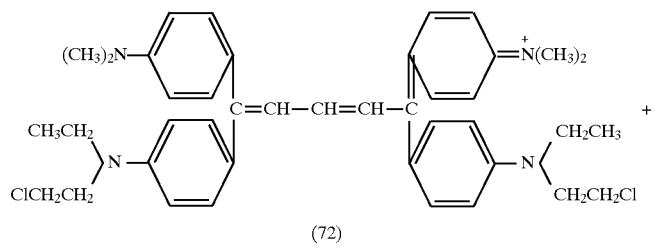

(72)

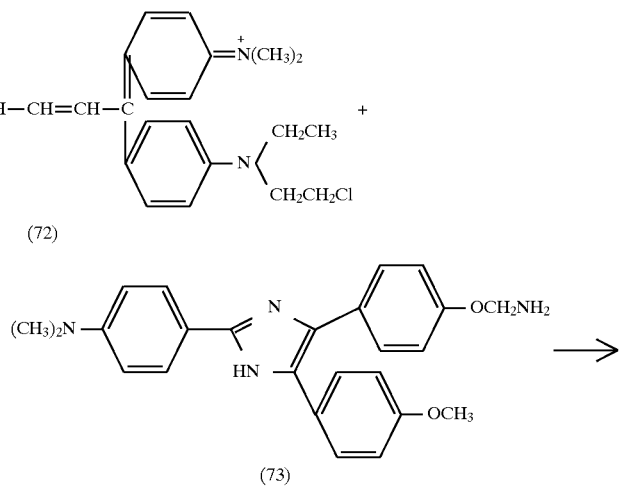

(73)

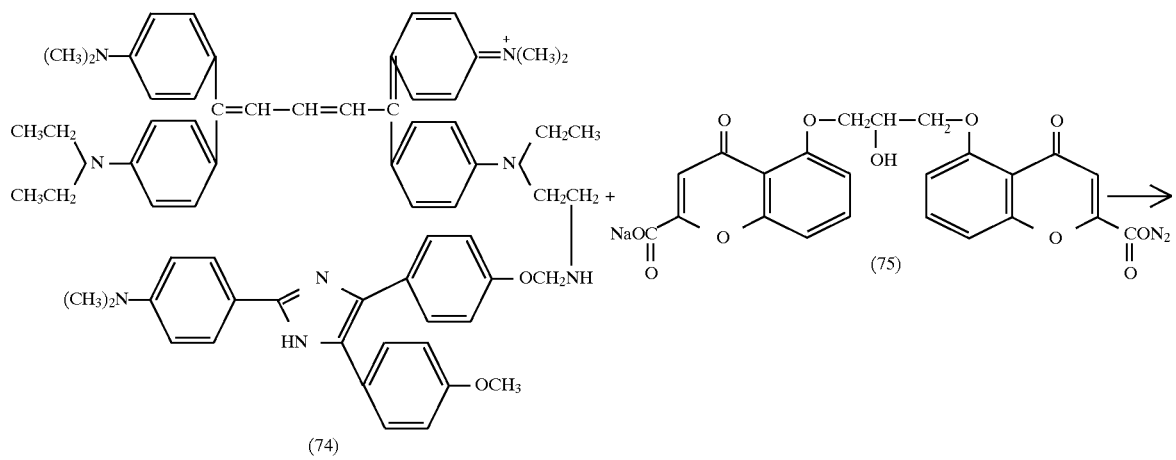

(74) (75)

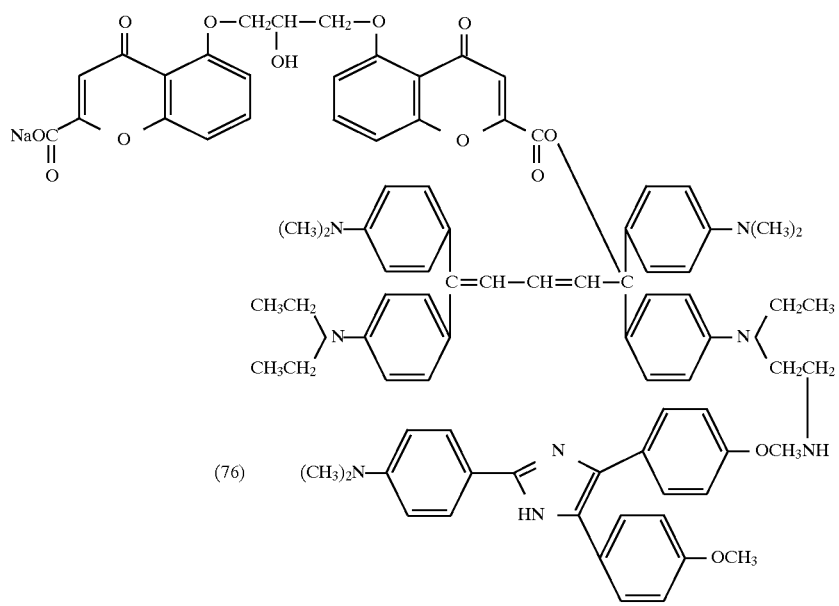

(76)

The alkylchloride 72 is reacted with alkyl amine Lophine derivate 73 to yield adduct 74 which is reacted with disodium cromoglycate, 75, to form the final product 76.

Preparations and Routes of Administration of Luminides

Luminides can be administered orally, intramuscularly or intraveneously.

Medicinal formulations which contain one or more Luminide compounds as the active compound can be prepared by mixing the Luminide (s) with one or more pharmacologically acceptable excipients or diluents, such as, for example, fillers, emulsifiers, lubricants, flavor correcting agents, dyestuffs or buffer substances, and converting the mixture into a suitable galenic formulation form, such as, for example, tablets, dragees, capsules or a solution or suspension suitable for parenteral administration. Examples of excipients or diluents which may be mentioned are tragacanth, lactose, talc, agar - agar, polyglycols, ethanol and water. Suspensions or solution in water can preferably be used for parenteral administration.

Also, Luminides can be prepared as sterile lyophilized powder to which a sterile solvent such as water or dimethylsulfoxide is added. Luminides are also prepared as a sterile lyophilized powder containing deoxycholate to effect a colloidal dispersion of insoluble Luminide. These preparations are administered as injectables including intramuscular and intravenous administration.

Topical Luminides can be prepared as a cream, lotion, gel, and ointment.

It is also possible to administer the active compounds as such without excipients or diluents, in a suitable form, for example in capsules.

Luminides can be packaged employing the usual sorts of precautious which the pharmacist generally observes. For example, the preparations may be packaged in light protecting vials and may be refrigerated if necessary.

EXEMPLARY LUMINIDE PHARMACEUTICALS

Prostaglandins possess potent renal, cardiac, hemodynamic, and other physiological effects; however, the free agents are 95% inactivated during one passage through the pulmonary circulation and are essentially eliminated in 90 seconds from intravascular injection. A luminide which is resistant to intravascular inactivation comprising a C functionality of prostaglandin $A_1$ $A_2B_1E_1$, $E_2$ or an analogue which possesses a vasodilatory effect on coronary arteries and other human vascular beds is an agent for the treatment of ischemic heart disease and is a antihypertensive agent with a long halflife. A luminide which is resistant to intravascular inactivation comprising a C functionality of postaglandin E, F, A or an analogue which possesses a positive cardiac inotropic effect is an inotropic agent with a long halflife. A luminide which is resistant to intravascular inactivation comprising a C functionality of prostaglandin A, E, or an analogue prostaglandin which possesses natriuretic and diuretic activity is a diuretic agent with a long halflife. A luminide which is resistant to intravascular inactivation comprising a C functionality of prostaglandin A, G, $E_1$, $E_2$ or an analogue such as 15(S)-15-methyl PGE 2 methylester, 16,16-dimethyl $PGE_2$,... AY-22,093, AY. . .22,469, AY-22, 443, or 15(R)-15-methyl $PGE_2$ which inhibits gastric acid secretion is an agent for the treatment of peptic and duodenal ulcer disease with a long halflife. A luminide which is resistant to intravascular inactivation comprising a C functionality of prostaglandin $D_2$, $E_1$ or an analogue which inhibits platelet aggregation is an antithromboembolic agent with a long halflife. A luminide which is resistant to intravascular inactivation comprising a C functionality of prostaglandin $E_1$, $E_2$ or an analogue which causes bronchial dilatation is an agent for the treatment of asthma and allergic and hypersentivity reactions with a long halflife. A luminide which is resistant to intravascular inactivation comprising a C functionality of prostaglandin F2 or an analogue which causes abortion by luteolysis is an agent for therapeutic abortion with a long halflife. A luminide which is resistant to intravascular inactivation comprising a C functionality of prostaglandin $A_2$, $E_1$, $E_2$, or an analogue which induces erythropoiesis by stimulating the release of erythropoietin from the renal cortex is an agent for the treatment of anemia. A luminide which is resistant to intravascular inactivation comprising a C functionality of prostaglandin E or an analogue which modulates T lymphocytes to decrease their ability to reject an allogenic graft is an agent to prolong allograft survival.

A cellular permeant luminide comprising a C functionality of cellular impermeant 2'-isopropyl-4'-(trimethylammonium chloride)-5'-methylphenyl piperidine -1-carboxylate (Amo 1618) which inhibits the cyclization of trans-geranyl-geranyl-PP to copalyl-PP during Kaurene synthesis is a fungicidal agent.

A cellular permeant luminide comprising a C functionality of cellular impermeant adenosine cyclic 3', 5'-monophosphate or an analogue which inhibits the release and formation of phlogistic mediators such as histamine and kinins is an agent for treating asthma and hypersensitivity and anaphylactic reactions.

A cellular permeant luminide comprising a C functionality of cellular impermeant 4'-sulfamylphenyl 2-azo -7-acetamid-1-hydroxynaphthalene-3,6-disulfonate (Neoprontosil), 4'-sulfamyl-2, 4-diaminoazobenzene (Prontosil), or 5-(p-sulfamylphenylazo) salicylic acid (Lutazol) which possess potent carbonic acid anhydrase inhibition is a diuretic agent.

A cellular permeant luminide comprising a C functionality of a cellular impermeant analogue of S-adenosyl homocysteine or sinefungin is an oncostatic agent.

A cellular permeant luminide comprising a C functionality of the cellular impermeant phosphoglycolohydroxamate which inhibits Class II aldolases present in bacterial and fungi and is noninhibitory of Class I aldolases present in animals is an antibacterial and antifungal agent.

A cellular permeant luminide comprising a C functionality of a cellular impermeant inosine analogue such as formycin B which inhibits nucleotide phosphorylase during nucleotide metabolism is an agent for disorders of purine metabolism such as gout, is an agent that alters the toxicity and/or antitumor behavior of other analogue-containing nucleosides such as 6-thioguanosine or 6-mercaptopurine ribonueleoside, and is an immunosuppressive agent by disruption of purine metabolism.

A cellular permeant luminide comprising a C functionality of cellular impermeant phosphonoformate (Foscarnet) which inhibits the HIV reverse transcriptase enzyme is an agent for the treatment of acquired immunodeficiency syndrome. The synthesis and the results of treatment of C3H mice infected with Raucher Spleen Focus Forming Virus with MTL J-1, a cellular permeant luminide comprising a C functionality of phosphonoformate, is given in Experimental Secions 1 and 3, respectively.

A cellular and blood-brain barrier permeant luminide comprising a C functionality of cellular and blood brain-barrier impermeant γ-amino-butyric acid (GABA) which is the major inhibitory neurotransmitter in the mannalian central nervous system or comprising a C functionality of a cellular and blood-brain barrier impermeant inhibitor of the GABA-degrading enzyme, GABA: 2-oxoglutarate aminotransferase such as gabaculine, N-(5'-phosphopyridoxyl) -4-aminobutyric acid, ethanolamine -o-sulfate, γ-vinyl GABA, or γ-acetylenic GABA; or comprising a C functionality of a cellular and blood-brain barrier impermeant compound which enhances GABA release such as Baclofen is an anti-convulsant, muscle relaxant, sedative, and anxiolytic agent.

A cellular permeant luminide comprising a C functionality of a cellular impermeant oligonucleotide which binds to RNA or DNA and blocks transcription or translation of HIV or P-glycoprotein gene products is an agent for the treatment of AIDs and chemotherapeutic drug, resistance, respectively.

A blood-brain barrier permeant luminide comprising a C functionality of blood-brain barrier impermeant adenosine which binds to brain purinergic receptors to suppress opiate withdrawal is an agent for the management of opiate withdrawal syndrome.

A slowly releasing peripherally acting luminide comprising a C functionality of adenosine which causes coronary vasodilatation is a long acting agent for the treatment of ischemic heart disease.

A cellular permeant luminide comprising a C functionality of cellular impermeant 3-hydroxy-3-methylglutarate, 3-hydroxybutyrate, 3-hydroxy-3-methylpentanoate, 4-bromocrotonyl-CoA, but-3-ynoyl-CoA, pent -3-ynoyl-CoA, dec -3-ynoyl-CoA, ML-236A, ML-236B (compactin), ML-236C, mevinolin, mevinolinic acid, or a mevalonic acid analogue which is an inhibitor of 3-hydroxy -3-methylglutaryl-CoA reductase which catalyzes the rate-limiting and irreversible step of cholesterol synthesis where inhibition at this step does not lead to the accumulation of nonmetabolizable precursors is an anticholesterol agent.

A cellular permeant luminide comprising a C functionality of cellular impermeant thioinosinate which suppresses T lymphocytes is an immunosuppressant agent.

A cellular permeant luminde comprising a C functionality of cellular impermeant Suramin, which is a powerful inhibitor of energy driven calcium uptake by the sarcoplasmic reticulum and is an intracellular inhibitor of $Na^+$-$K^+$ATPase where both activities increase intracellular calcium concentrations with a concomitant inotropic effect is a cardiac inotropic agent.

A cellular permeant luminide comprising a C functionality of a cellular impermeant norepinephrine N-methyltransferase inhibitor such as 2,3-dichloro-α-methylbenzylamine, 2,3-dichlorobenzylamine, 2,3-dichlorobenzamidine, or 3,4-dichlorophenylacetamidine is a specific epinephrine action blocking agent.

A cellular permeant luminide comprising a C functionality of cellular impermeant adenosine cyclic 3', 5'-monophosphate or a cAMP analogue which blocks the synthesis of fatty acids and cholesterol in the liver is an antilipidemic agent.

A cellular permeant luminide comprising a C functionality of a cellular impermeant inhibitor of dihydroxyphenylalanine decarboxylase during the synthesis of epinephrine and norepinephrine such as psitectorigenin, genistein, 3', 4',5,7-tetrahydroxy-8-methylisoflavone, orbol, 8-hydroxygenistein, 3',5,7-trihydroxy-4',6-dimethylisoflavone, 3',5,7-trihydroxy-4',8-dimethoxyisoflavone, D,L-B-(5-hydroxy-3-indolyl)-α-hydrazinopropionic acid, D,L-α-hydrazino-α-methyldopa, D,L-B-(3-indolyl), -α-hydrazinopropionic acid, a derivative of phenylalanine such as N-methyl-3,4-dopa, α-acetamido-3,4-dimethyoxycinnamic acid, DL-α-methyl-3,4-dopa, α-methyl-B-(3-hydroxy-4-methoxyphenyl)alanine, α-methyl- 3,4-dimethoxyphenylalanine, or d-catechin; D,L-B-(3- indolyl)-α-methyl-α-hydrazinopropionic acid (R)-3 [3,4-dihydroxyphenyl]-1-fluoropropylamine, (S)-α-fluoromethyldopa, (S)-α-fluoromethyltyrosine, 5-(3,4-dihydroxycinnamoyl) salicylic acid, 3-hydroxycinnamic acid, caffeic acid, 3-mercaptocinnamic acid, α-methyl-3-hydroxycinnamic acid, α-ethyl-3-hydroxycinnamic acid, 3-hydroxy-w-nitrostyrene, 3,4-dihydroxyhydrocinnamic acid, 3-hydroxybenzalacetone, 3-hydroxychalone, 3-hydroxybenzal furanyl ketone, 3-hydroxybenzal thiophenyl ketone, 3',4'-dihydroxyflavone, 8-O-glucoseflavone, flavone, 3-hydroxyphenyl pyruvic acid, 3,4-dihydroxyphenylpyruvic acid phenylthiopyruvic acid, 4-hydroxyphenylpyruvic acid, dithiosalicyclic acid, 1-hydroxy-2-naphthoic acid, 3-hydroxy-7-sulfo-2-naphtholic acid, 3,5-dihydroxy-2-naphtholic acid, 4-chlorocinnamic acid, 2-chlorocinnamic acid, 2,4-dichlorocinnamic acid, 3-nitrocinnamic acid, 3,5-dibromo-2-hydroxycinnamic acid, 2,4,6-triiodo -3-hydroxycinnamic acid, 2-hydroxy-4'-cyanochalone, 4-(4-hydroxycinnamoyl) benzylnitrile, 2-(4-hydroxycinnamoyl)-1,4-dihydroxybenzene, quercetin-6'-sulfonic acid, 5-(2-hydroxy-3,5-dibromocinnamoyl) salicylic acid or 5-(3-hydroxycinnamoyl) salicylic acid is an antihypertensive agent.

A sperm permeant luminide comprising a C functionality of sperm impermeant, inhibitors of acrosin, a proteolytic enzyme located in the acrosome of sperm, such as tosyl lysine chloromethyl ketone, N-α-tosyl-L-arginine chloromethyl ketone, or ethyl p-guanidinobenzoate is a contraceptive agent.

A cellular permeant luminide comprising a C functionality of cellular impermeant adenosine cyclic 3',5'-monophosphate (cAMP), $N^6$ , $O^2$-dibutyryladenosine cyclic 3',5'-monophosphate or an analogue which produces an inotropic response is a cardiac inotropic agent.

A cellular permeant luminide comprising a C functionality of a cellular impermeant adenosine kinase enzyme inhibitor such as 6,6'-dithiobis (9-B-D-ribofuranosylpurine) is a chemotherapeutic agent and an immunosuppressive agent.

A mitochondrial and blood-brain barrier permeant luminide comprising a C functionality of a mitochondrial and blood-brain barrier impermeant inhibitor of monoamine oxidase such as phenylhydrazine, phenylethylidenehydrazine, isopropyihydrazine, or iproniazid is an antidepressant.

A cellular and blood-brain barrier permeant luminide comprising a C functionality of a cellular and blood-brain barrier impermeant inhibitor of catechol-o-methyltrasferase such as 3,5-diiodo-4-hydroxybenzoic acid, S-3'-deoxyadenosylL-homocysteine, pyrogallol, R04-4602, gallic acid, 3,5-dihydroxy-4-methylbenzoic acid, 1,3-dihydroxy-2-methoxybenzene, 1-hydroxy-2,3-dimethoxybenzene, 2-hydroxy-1,3-dimethoxybenzene, 1,3-dihydroxy-4-methoxybenzene, catechol, 3,4-dihydroxybenzoic acid, caffeic acid, 5,6-dihydroxyindole, noradnamine, dopacetamide, H 22/54, quercetin, nordihydroguaiaretic acid, U-0521, arterenone, methylspinazarin, MK 486, dopa, papaveroline, isoprenaline, 7,8-dihydroxychlorpromazine, 3-hydroxy-4-pyridone, tetrahydroisoquinoline pyridoxal 5'-phosphate, iodoacetic acid, 3-mercaptotyramine, dehydrodicaffeic acid dilactone, methylspinazorin, 3',5,7-trihydroxy-4',6-dimethoxyisoflavone, 3',5,7-trihydroxy-4',8-dimeth-oxyisoflavone, 6,7-dihydromethylspinazarin, S-adenosylhomocysteine, S-tubercidinylhomocysteine, 3',8-dihydroxy-4',6,7-trimethoxyisoflavone,7-O-methylspi nochrome B, 6-(3-hydroxybutyl)-7-O-methylspinachrome B, 3,5-diiodosalicyclic acid, or pyridoxal-5'-phosphate is an antidepressant agent which increases brain levels of monoamines and is an agent to block the metabolism of L-dopa administered for the treatment of Parkinsonism.

A cellular permeant luminide comprising a C functionality of a cellular impermeant inhibitor of adenosine deaminase which blocks the metabolism of adenosine such as coformycin, arabinosyl-6-thiopurine, 6-methylthioinosine, 6-thioinosine, 6-thioguanosine, $N^1$-methyladenosine, $N^6$-methyladenosine, 2-fluorodeoxyadenosine, 2-fluoroadenosine, inosine, 2'-deoxyinosine, deoxycoformycin, 1,6-dihydro-6-hydroxymethyl purine ribonucleoside, erythro-9-(2-hydroxy-3-nonyl)adenine, or 9-B-D-arabinofuranosyl-6-hydroxylaminopurine is a vasodilatory agent, an immunosuppressive agent, a chemotherapeutic potentiating agent, and an agent to enhance cardiac recovery following ischemia. The mechanism in the first case involves the accumulation of adenosine which is a vasodilatory agent; the mechanism in the second case involves disruption of purine metabolism; the mechanism in the third case involves the disruption of the degradation of purine analogue chemotherapeutic agents; the mechanism in the fourth case involves blocking the loss of catabolic products of adenosine triphosphate in the form of purine nucleotides and oxypurines during ischemia. Additional luminides effective in enhancing post ischemic cardiac recovery by the latter mechanism include those with C moietics of inhibitors of adenylate kinase, 5'-nucleotidase, and adenosine translocase such as $p^1p^5$-diadenosine pentaphosphate, $\alpha,\beta$-methylene adenosine diphosphate, and nitrobenzyl-6-thioinosine, respectively.

A blood-brain barrier permeant luminide comprising a C functionality of a blood-brain barrier impermeant inhibitor of Γ-aminobutyric acid uptake such as D,L-2,4-diaminobutyric acid, D,L-B-hydroxy GABA, (−)-nipecotic acid, trans-4-aminocrotonic acid, cis-3-aminocyclopentane-1-carboxylic acid, trans-3-aminocyclopentane-1-carboxylic acid, B-guanidinopropionic acid, homohypotaurine, 4-aminopentanoic acid, homotaurine, B-alanine, imidazoleacetic acid, 6-aminohexanoic acid, D,L-carnitine, D,L-2,6-diaminopimetic acid, D,L-2-fluoro GABA, guanidino acetic acid, 2-hydrazinopropionic acid, taurine, D,L-ornithine, or sulphanilamine potentiates the inhibitory action of GABA and is a muscle relaxant, anticonvulsant, sedative, and anxiolytic agent.

A cellular permeant luminide comprising a C functionality of cellular impermeant inositol 1,4,5-triphosphate which is a major second messenger for stimulating a whole range of cellular processes such as contraction, secretion, and metabolism is an agent for activating these processes including secretion of neural transmitters to function as an agent for the treatment of mental disorders or secretion of insulin to function as a hypoglycemic agent.

A cellular permeant luminide comprising a C functionality of cellular impermeant guanosine 5' cyclic monophosphate or 8-bromo guanosine 5' cyclic monophosphate which relaxes smooth muscle is an antihypertensive and bronchodilator agent.

A cellular and blood-brain barrier permeant luminide comprising a C functionality of a cellular and blood-brain barrier impermeant inhibitor of the uptake system for glycine, the inhibitory synaptic transmitter of the spinal cord, such as hydrazinoacetic acid is an agent for spinal reflex inhibition.

A cellular permeant luminide comprising a C functionality of a cellular impermeant isoquinoline-sulfonamide inhibitor of protein kinase C, cAMP-dependant protein kinase, or cGMP-dependent protein kinase such as N-(2-aminoethyl)-5-isoquino-linesulfonamide is an agent which blocks the secretion, contraction, and metabolic events regulated by these mediators of external phydsiologic stimuli.

A cellular permeant luminide comprising a C functionality of cellular impermeant Ribavirin which is active against HSV-1 and 2, hepatitis, and influenza viruses, or phosphonoacetic acid which is a highly specific inhibitor of Herpes Simplex virus induced polymerase and is active against HSV-1 and HSV-2, or adenine arabinoside (ara-A), cytosine arabinoside (Ara-C), ara-A 5'-monophosphate (ara-AMP), or hypoxanthine arabinoside (ara-Hx) which is active against HSV or phagicin which is active against vaccinia and HSV, or 4-fluoroimidazole, 4-fluoroimidazole-5-carboxylic acid, 4-fluoroimidazole-5-carboxamide, 5-fluoro-1-B-D-ribofurano- sylimidazole-4-carboxamide, 5-amino-1-B-D-ribofuranosyl- imidazole-4-carboxamide, poly (I)·poly (C), sinefungin, iododeoxyuridine, 9-(2-hydroxy-ethoxymethyl) guanine, gliotoxin, distamycin A, netropsin, congocidine, cordycepin, 1-B-D-arabinofuranosylthymine, 5,6-dihydroxy-5-azathymidine, pyrazofurin, toyocamycin, or tunicamycin is an antiviral agent.

A cellular permeant luminde which comprises a C functionality of a cellular impermeant inhibitor of fungal chitin synthetase such as polyoxin D, nikko-mycin Z, or nikkomycin X; or which comprises a C functionality of an impermeant antifungal agent such as ezomycin $A_1$, $A_2$, $B_1$, $B_2$, $C_1$, $C_2$, $D_1$, or $D_2$ or platenocidin, septacidin, sinefungin, A9145A, A9145C, or thraustomycin is an antifungal agent.

A blood-brain barrier permeant luminide comprising a c functionality of a blood-brain barrier impermeant inhibitor of central nervous system carbonic anhydrase such as methazolamide, or 2-benzoylimino-3-methyl-$\Delta^4$-1,3,4-thiadiazoline-5-sulfonamide subsgituted at the benzolyl group with 3,4,5-trimethoxy, 2,4,6-trimethoxy, 2,4,5-trimethoxy, 4-chloro, 4-bromo, 4-iodo, or hydrogen is an anticonvulsant agent.

A cellular and blood-brain barrier permeant luminide comprising a C functionality of a cellular and blood-brain barrier impermeant inhibitor of dopamine-B-hydroxylase during the synthesis of norepinephrine and epinephrine such as fuscaric acid, 5-(3',4'-dibromobutyl)picolinic acid, 5-(3'-bromobutyl) picolinic acid, 5-(3',4'-dichlorobutylpicolinic acid, YP-279, benxyloxyamine, p-hydroxybenzyloxyamine, U-21,179, U-7231, U-6324, U-0228, U-5227, U-10,631, U-10,157, U-1238, U-19,963, U-19,461, U-6628, U-20,757, U-19,440, U-15,957, U-7130, U-14,624, U-22,996, U-15, 030, U-19,571, U-18,305, U-17,086, U-7726, dimethyldithiocarbamate, diethyldithiocarbamate, ethyldithiocarbamate, 2-mercaptoethylguanidine, thiophenol, 2-mercaptoethylamine, 3-mercaptopropylguanidine, 3-mercap- toprbpyl-N-methylguanidine, 2-mercaptoethanol, 2-mercaptoethyl-N-methylguanidine, 2-mercaptoethyl-N,N'-dimethylguanidine, 4,4,6-trimethyl-3,4-dihydropyrimidine-2-thiol, N-phenyl-N'-3-(4H-1,2,4-trizolyl)thiourea, methylspinazarin, 6,7-dimethylspinazarin, 7-O-methyspinochrome B, 6-(3-hydroxybutyl)-7-O-methylspinachrome B, aquayamycin, chrothiomycin, frenoclicin, N-n-butyl-N'-3-(4H-1,2,4-trazolyl) thiourea, propylthiouracil, mimosine, mimosinamine, or mimosinic acid is an antihypertensive agent.

A cellular permeant luminide of a cellular impermeant inhibitor of histidine decarboxylation during the synthesis of histamine such as $^2$-hydroxy-5-carbomethoxybenzyloxyamine, 4-toluene-sulfonic acid hydrazide, 3-hydroxy benzyloxyamine, hydroxylamine, aminooxyacetic acid, 4bromo-3-hydroxybenzyloxyamine (NSD-1055), rhodanine substituted in the 3 position with p-chlorophenethyl, p-chlorobenzyl, p-methylthiobenzyl, p-methylbenzyl, p-fluorobenzyl, amino, 3,4-dichlorobenzyl, p-bromobenzyl, p-methoxybenzyl, p-bromoanilino, p-iodoanilino, p-chloroanilino, p-toluidino, anilino, 2,5-dichloroanilino, dimethylamino, or p-methoxyphenyl; 2-mercaptobenzimidazole-1,3-dimethylol, 4-bromo-3-hydroxy -benzoic acid, 4-bromo-3-hydroxybenzyl alcohol, 4-bromo-3-hydroxy-hippuric acid, (R,S)-α-fluoromethyl-histidine, (S)-α-fluoromethylester, L-histidine ethyl ester, L-histidinamide, D,L-3-amino-4-(4-imidazolyl)-2-butanone, 2-bromo-3-hydroxybenzyloxyamine, 5-bromo-3-hydroxybenzyloxyamine, 4,6-dibromo-3-hydroxybenzyloxyamine, aminooxypropionic acid, benzyloxyamine, 4-bromo-3-benzenesulfonyloxybenzyloxyamine, 3',5,7-trihydroxy-4',6-dimethoxyisoflavone, lecanoric acid, N-(2,4-dihydroxybenzoyl)-4-aminosalicylic acid, or 3',5,7-trihydroxy-4',8-dimethoxyisoflavone is an agent for the treatment of allergy, hypersensitivity, gastic ulcer, and inflamation.

Luminides also comprise C functionalities of pharmaceutical molecules as appear in *Physicians Desk Reference,* Edward R. Barnhart, 41th ed., 1987, Medical Economics Company Inc., N.J.; *USAN and the Dictionary of Drug Names,* ed. by Mary C. Griffiths, The United States Pharmacopedial Convention, (1986); and The *Pharmacological Basis of Therapeutics,* ed. by A.G. Gilman, L. Goodman, A. Gilman, 7th ed., (1985), MacMillan Publishing Co., N.Y., N.Y., (incorporated by reference) where the pharmacokinetics and/or the pharmacodynamics of these agents are altered via delivery to the site of action by way of a luminide agent such that the therapeutic effect or therapeutic ratio is enhanced. Some examples follow which are not meant to be exhaustive.

A luminide with high permeance to the blood-brain barrier comprising a C functionality of a centrally acting converting enzyme inhibitor such as captopril which possesses a lesser blood-barrier permeance is an agent with increased efficacy of the central nervous system antihypertensive effect of the centrally acting converting enzyme inhibition including captopril.

A luminide with an A moiety which reacts with free radicals and electron carriers in the cytosol of bacteria to effect release of the C moiety and which possesses greater permeance or B-lactamase resistance than its C moiety of a bacterial wall synthesis inhibitor such as a penicillin, cephalosporin, or cephamycin is a more efficacious and broad spectrum antibacterial agent than the free C moiety.

A luminide possessing more favorable pharmacokinetics or pharmacodynamics than its C moiety of an agent which blocks bacterial synthesis of tetrahydrofolate such as a sulfonamide (an analogue of p-aminobenzoic acid) including sulfanilamide, sulfadiazine, sulfamethoxazole, sulfisoxazole, or sulfacetamide or an inhibitor of dihydrofolate reductace including pyrimethamine, cycloguanil, trimethoprin, isoaminopterin, 9-oxofolic acid, or isofolic acid is a more efficacious antibacterial than the free C moiety.

A luminide possessing more favorable pharmacokinetics or pharmacodynamics than it C functionality of a bactericidal agent such as nalidixic acid or oxolinic acid is a more efficacious antibacterial than the free C moiety.

A luminide. possessing more favorable pharmacokinetics or pharmacodynamics than its C moiety of an inhibitor of bacterial protein synthesis such as vancomycin, an aminogylcoside, erythromycin, tetracyclin, or chloramphenicol is a more efficacious antibacterial agent than the free C moiety.

A luminide prossessing more favorable pharmacokinetics or pharmacodynamics than its C moiety of an inhibitor of viral DNA polymerase such as vidarabine is a more efficacious antiviral agent than the free C moiety.

A luminide possessing more favorable pharmacokinetics or pharmacodynamics than its C moiety which is tuberculostatic or tuberculocidal such as isoniazid or aminosalicyclic acid is a more efficacious agent for the treatment of tuberculosis than the free C moiety.

A luminide possessing more favorable pharmacokinetics or pharmodynamics than its C moiety of an anthelmintic agent such as oxamniquine, piperazine, metronidazole, diethylcarbamazine, paromomycin, niclosamide, bithionol, metrifonate, hycanthone, dichlorophen, or niclosamide is a more efficacious anthelmintic agent than the free C moiety.

A luminide possessing more favorable pharmacokinetics or pharmacodynamics than its C moiety of an $H_2$-blocking agent such as cimetidine or ranitidine is a more efficacious anti-ulser agent than the free C moiety.

A luminide possessing more favorable pharmacokinetics or pharmacodynamics than its C moiety of an agent which blocks release of norepinephrine such as sotalol, guanethidine, pindolol, pronethalol, KO 592, practolol, oxprenolol, or pronethalol is an antiarrhythmic, antihypertensive and antipsychotic agent.

A luminide possessing more favorable pharmacokinetics or pharmacodynamics than its C moiety of a xanthine oxidase inhibitor such as allopurinol, thioinosinate, 5,7-dihydroxypyrazolo [1,5-a] pyrimidine substituted at the 3 position with hydrogen, nitro, bromo, chloro, phenyl, 3-pyridyl, p-bromophenyl, p-chlorophenyl, p-acetylanilino, p-tolulyl, m-tolulyl, naphthyl, or 3,4-methylenedioxyphenyl; 8-(m-bromoacetamidobenzylthio) hypoxanthine, 8-(m-bromoacetamidobenzylthio) hypoxanthine, guanine substituted at the 9 position with phenyl, 4-chlorophenyl, 3-chlorophenyl, 3,4-dichlorophenyl, 4-methoxyphenyl, 3,4-dimethoxyphenyl, 4-dimethylaminophenyl, 4-aminophenyl, 3-aminophenyl, 3-trifluormethylphenyl, 4-benzamido, 4-carboxylphenyl, 4-methylpheyl, 4-ethylphenyl, 3-methylphenyl, B-naphthyl, or 4-ethoxyphenyl; 4,6-dihydroxypyrazolo [3,4-d] pyrimidine, 4-trifluoromethylimidazoles substituted at the 2 position with phenyl, p-chlorophenyl, p-methoxyphenyl, p-acetylanilino, p-nitrophenyl, p-dimethylaminophenyl, p-cyanophenyl, p-fluorophenyl, p-carboxyphenyl, m-chlorophenyl, 3,4-dichlorophenyl, 4-pyridyl, 3-pyridyl, 2-quinolyl, 6-quinolyl, 4-quinolyl, 7-quinolyl, 2-pyrazinyl, or 1-(2-pyridyl-4-trifluoromethyl-5-bromoimidazolyl; 5-(4-pyridyl)-1,2,4-triazoles substituted at the 5 position with 4-pyridyl, 3-pyridyl, 2-pyridyl, phenyl, p-chlorophenyl, m-chlorophenyl, p-sulfonamidophenyl, 3,5-dichlorophenyl, 3,5-dicarboxyphenyl, 6-quinolyl, 2-furyl, 4-pyridazinyl, 2-thienyl, 2-pyrimidinyl, 4-pyrimidinyl, or 4-pyrazinyl; difunisal, 4(or 5)-(2-aminoethylthio-azo)imidazole-5(or 4)-carboxamide, 4 (or 5)-diazoimidazole-5(or 4)-carboxamide , or S-[5(or 4)-carbamoyl-4(or 5)-imidazolyl azo] cysteine is a more efficacious agent for the treatment of gout and hyperuricemic conditions than the free C moiety.

A luminide possessing more favorable pharmacokinetics or pharmacodynamics than its C moiety which inhibits DNA synthesis such as a bis-thiosemicarbazone, 3,5-diisopropylsalicyl- hydroxamic acid, 4-hydroxybenzoylhydroxamic acid, 3-methylsalicylhydroxamic acid 2,5-dihydroxybenzoylhydroxamic acid, or 2-hydroxy-3,4,5- trimethoxybenzoylhydroxamic acid; or which inhibits nucleotide synthesis such as N-(phosphoacetyl)-L-aspartate which inhibits asparatate transcarbamylase during pyrimidine synthesis, or azaserine or 6-diazo-5-oxo-L-norleucine which inhibits purine synthesis at the phosphoribosyl-formyl-glycineamidine synthetase step; or which is an antifolate such as methotrexate, 2,4-diamino-5-benxyl-6-(4-phenylbutyl) pyrimidine, 2,4-diamino-5-phenyl-6-(4-phenylbutyl) pyrimidine, 2,4-diamino-5-phenyl-6-(3-anilinopropyl) pyrimidine, 2-amino-4-hydroxy-5-phenyl-6-(3-p-aminobenzoylglutamic acid propyl) pyrimidine, N-(p-[[(2,4-diamino-6-quinazolinyl)methyl]methylamino]benzoyl]-L-glutamic acid, N-[p-[2,4-diamino-5-methylquinazolinyl)methylamino]benzoyl]-L-aspartic acid, N-[p-[[(2-amino-4-hydroxy-6-quinazolinyl) methyl-] methylamino] benzoyl]-L-glutamic acid, 2,4-diaminoquinazolines: CCNSC 105952, CCNSC 112846, CCNSC 121346, CCNSC 122761, CCNSC 122870, CCNSC 529859, CCNSC 529860, or CCNSC 529861; 8-aza GMP, 7-deaza-8-aza GMP, 2'-dGMP, B-D-arabinosyl GMP, pentopyranine A-G, B-ribofuranosyl-1,3-oxazine-2,4-dione, pyrazofurin, 6-(p-chloroacetylanilinomethyl)-5-cetylvinylanilinomethyl)-5-(p-chlorophenyl)-2,4-diaminopyridine, 6-(p-chloroacetyl- ethylanilino-methyl)-5-(p-chlorophenyl)-2,4-diamino pyridine, 6-(p-chlorophenylbutylanilinomethyl)-5-(p-chlorophenyl)-2,4-diamino pyridine, p-(2,6-diamino-1,2-dihydro-2, 2-dimethyl- S-triazin-1-yl) phenylpropionyl sulfanilylfluoride or variants of the propionamide bridge of acrylamido, N-ethylsulfonamido, N-ethylcaboxamido, oxyacetamido, or oxythyloxy; or which inhibits purine or pyrimidine synthesis such as xylosyladenine, 6-azauridine, 5-aminouridine, 5-azaorotic acid; or which inhibits nucleotide interconversion such as hadacidin, 6-mercaptopurine, azathioprine, nitro-dUMP,psicofuranine, decoyinine, 5-fluorouracil, 5-fluorodeoxyuridine, shadowmycin; or which inhibits nucleotide utilization such as cytosine arabinoside, arabinosyladenine; or which becomes incorporated into polynucleotides such as 8-azaguanine, tubercidine, toyocamycin, sangivamycin, formycin, 7-deazainosine, 8-azainosine, or 7-thia-7, 9-dideazainosine; or which is a glyoxalase inhibitor such as Glyo-I, or Glyo-II, is a more efficacious antineoplastic agent than the free C moiety.

A luminide possessing more favorable pharmacokinetics or pharmacodynamics than its C moiety of an agent which blocks synthesis of prostaglandin $A_2$ which effects platelett aggregation such as salicylic acid, pyrogallol, 5,8,11,14-eicosatetraynoic acid, α-naphthol, guaiacol, propylgallate, nordihydroguiaretic acid, N-0164, benzydamine, 9,11-azoprosta-5, 13-dienoic acid, 2-isopropyl-3-nicotinylindole, is a more efficacious antithrombotic agent than the free C moiety.

A luminide possessing more favorable pharmacokinetics or pharmacodynamics than its C moiety of an agent wnich blocks prostaglandin synthetase such as indomethacin, sulindac, tolmetin, mefenamic acid, ibuprofen, naprozen, fenoprofen, fluribprofen, ketoprofen, meclofenamic acid, flufenamic acid, niflumic acid, benzydamine, oxyphenbutazone, asprin, acetaminophen, salicylamide, O-carboxydiphenylamine, tolectin, diclofenac, 2,7-dihydroxynaphthalene, 5-(4-chlorobenzoyl)-1-methylpyrrole-2-acetic acid, 5-(4-methylbenzoyl)-1,4-dimethylpyrrole-2-acetic acid, 5-(4-chlorobenzoyl)-1,4-dimethylpyrrole-2-acetic acid, 5-(4-fluorobenzoyl)-1,4-dimethylpyrrole-2-acetic acid, 5-(4-chlorobenzoyl)-1,4-dimethylpyrrole-2-(2-propionic acid), 5,6-dehydroarachidonate, 11,12-dehydroarachidonate, or 5,8,11, 14-eicosatetraynoate; or of an agent which blocks lipoxygenase or blocks leukotriene action such as BW755C, FPL 55712, or U-60,257 is a more efficacious nonsteroidal antiinflammatory agent than the free C moiety.

A luminide possessing more favorable pharmacokinetics or pharmacodynamics than its C moiety of an antiarrhythmic agent such as procainamide or quinidine is a more efficacious antiarrhythmic agent than the free C moiety.

A luminide possessing more favorable pharmacokinetics or pharmacodynamics than its C moiety of an inhibitor of hepatic synthesis of Vitamin K dependent clotti-ng factors such as warfarin sodium, dicumarol, 4-hydroxycoumarin, phenprocoumon, or acenocoumarol is a more efficacious anticoagulant than the free C moiety.

A luminide possessing more favorable pharmacokinetics or pharmacodynamics than its C moiety which directly relaxes vascular smooth muscle such as hydralazine, minoxidil, or isoxsuprine is a more efficacious antihypertensive agent than the free C moiety.

A luminide possessing more favorable pharmacokinetics or pharmacodynamics than its C moiety of a $Na^+$-$K^+$-ATPase inhibitor such as digtoxigenin, digoxigenin, cymarol, periplogenin, or strophanthidiol, or ouabain glycosides, cardenolides, or basic esters, or ICI-63,632, ICI-63,605, ICI-62-655, ICI-62,838, ICI-69,654, ICI-58, 622, ICI-61,374, ICI-57,267, ICI-61,424, ICI-61,411, ICI-65,199, ICI-70,898, ICI-70,899, ICI-70,900, ICI-70,901, ICI-62,966, ICI-65,210, ICI-63,116, ICI-62,936, ICI-65, 551, ICI-63,978, ICI-62,276, ICI-63,056, ICI-67,135, ICI-67,167, ICI-67,134, ICI-67,875, ICI-67,880, or ICI-61,558 is a more efficacious inotropic agent than the free C moiety.

A luminide possessing more favorable pharmacokinetics or pharmacodynamics than its C moiety which is a calcium channel blocker such as prenylamine, verapamil, fendiline, gallopamil, cinnarizine, tiapamil, diltiazem, bencyclan, or nifedipine; or an agent which stabalizes calcium binding to cellular calcium stores and thereby inhibits the release of this calcium by contractile stimuli such as 8-(N,N-diethylamino)-octyl 3,4,5-trimethoxybenzoate (TMB-8) is a more efficacious vasodilatory agent than its free moiety.

A luminide possessing more favorable pharmacokinetics or pharmacodynamics than its C moiety of a monoamine oxidase inhibitor such as tranylcypromine, phenylethylamine, trans-cinnamic acid, phenelzine, or isocarboxazid is a more efficacious antidepressant agent than the free C moiety.

A luminide possessing more favorable pharmacokinetics or pharmacodynamics than its C moiety of a benzodiazepine compound such as clorazepate is a more efficacious tranquillizer than the free C moiety.

A luminide possessing more favorable pharmacokinetics or pharmacodynamics than its C moiety of an antiseizure agent such as valproic acid is a more efficacious antiepileptic agent than the free C moiety.

A luminide possessing more favorable pharmacokinetics or pharmacodynamics than its C moiety of an agent which causes repression of the synthesis of HMG-COA reductase such as 20-α-hydroxycholesterol, 22-ketocholesterol, 22-α-hydroxycholesterol, 25-hydroxycholesterol, 22-B-hydroxycholesterol, 7-α-hydroxycholesterol, 7-B-hydroxycholesterol, 7-ketocholesterol, or kryptogenin; or of an agent which inhibits HMG-COA reductase such as, lorelco; or of an agent which inhibits lipolysis such as 5-methylpyrazole -3-carboxylic acid (U-19425), nicotinic acid, uridine, inosine, 3,5-dimethylisoxazole (U-21221), 3,5-dimethypyrazole, prostaglandin $E_2$, eritadenine, or eritadenine isoamyl ester; or of an agent which inhibits lipogenesis such as ascofuranone, (−)-hydroxycitrate, or tetrolyl-CoA; or of an agent which is hypocholesterolemic such as lentysine; or of an agent which lowers triglycerides such as lopid; or of an agent which is an inhibitor of acetyl-CoA carboxylase during lipogenesis such as 2-methyl -2-[p-(1,2,3,4-tetrahydro-1-naphthyl)-phenoxy]-propionat e (SU13437), $^2$-(p-chlorophenoxy)-2-methylpropionate, kynurenate, xanthurenate, kynurenine, 3-hydroxyanthranilate, or 2-methyl-2-[p-(p-chlorophenyl) phenoxy] propionate; or of an agent which is an inhibitor of hepatic B-lipoprotein production such as orotic acid is a more efficacious hypolipidemic agent than its free C moiety.

A luminide possessing more favorable pharmacokinetics or pharmacodynamics than its C moiety of a vasodilater such as WS-1228A, or WS-1228B; or of an anti-inflammatory agent such as amicomacin A is a more efficacious vasodilator or anti-inflammatory agent, respectively, than the free C moiety.

A luminide with more favorable pharmacokinetics or pharmacodynamics than its C moiety which is a protease inhibitor such as leupeptin; or which is an inhibitor of pepsin such as a pepstatin, a pepstanone, or a hydroxypepstatin is a more efficacious agent for the treatment of muscular dystrophy or peptic ulcer disease, respectively, than its free C moiety.

A luminide with more favorable pharmacokinetics or pharmacodynamics than its C moiety of an inhibitor of cell surface enzymes such as bestatin, amastatin, forphenicine, ebelactone, or forphenicin is a more efficacious immuno-modifier agent than its free C moiety.

A luminide with more favorable pharmacokinetics or pharmacodynamics such as enhanced permeability relative to its C moiety of a phosphodiesterase inhibitor such as theophyllineacetic acid, theophylline, dyphylline, disodium cromoglycate, 6-n-butyl-2,8-dicarboxy-4,10-dioxo-1,4,7,10-tetrahydro-1,7-phenanthrolin, 2-chloroadenosine, dipyridamole, EG 626, AY-17,605, AY-17,611, AY-22,252, AY-22,241, cis-hinokiresinol, oxy-cis-hinokiresinol, tetrahydro-cis- hinokiresinol, trans-hinokiresinol, dehydrodicaffeic acid, 2,6,4'-trihydroxy-4-methoxybenzophenone, p-hydroxyphenyl crotonic acid, papaverine, 3-(5-tetrazolyl)-thioxanthone-10,10-dioxide, 3-carboxythioxanthone-10,10-dioxide, W-7, HA-558, MY-5445, OPC-3689, OPC-13135, or OPC-13013, reticulol, PDE-I, or PDE-II is a more efficacious cardiac stimulant, diuretic, vasadilator, platelett aggregation inhibitor, .and an agent for the treatment of asthma and allergic reaction than its free C moiety. Such a luminide comprising a C moiety of ICI 74,917 is also a more efficacious agent for the treatment of asthma and allergic reactions.

A luminide possessing more favorable pharmacokinetics or pharmacodynamics such as enhanced cellular or blood-brain barrier permeability or resistance to inactivation by tissue dehalogenases and transaminases than its C functionality of an inhibitor of tyrosine hydroxylase, the enzyme catalyzing the rate-limiting reaction in the biosynthesis of norepinephrine, such as azadopamine, isopropylazadopamine, dimethylazadopamine; triphenolic compounds such as n-propylgallate; diphenolic benzoic acid derivatives such as 3,4-dihydroxybenzoic acid; phenylcarbonyl derivatives such as 3,4-dihydroxybenzaldehyde, arterenone, or adrenalone H 22/54, 3-iodo-L-tyrosine, D,L-α-methyl-p-tyrosine, L-3-iodo-α-methyltyrosine, 3-bromo-α-methyltyrosine, gentistic acid, 3-chloro-α-methyltyrosine, phenylalanine derivatives, 3,5-diiodo-L-tyrosine, 3,5-dibromo-L-tyrosine, 3-bromo-α-methyl-L-tyrosine, 3-fluro-α-methyl-L-tyrosine, catechol analogues, 3,4-dihydroxyphenylethylacetamide, 3,4-dihydroxyphenyliso- proplyacetamide, 3,4-dihydroxyphenylbutylacetamide, 3,4-dihydroxyphenylisobutylacetamide, D,L-α-methylphenylalanine, D,L-3-iodophenylalanine, D,L-4-iodophenylalanine, D,L-α-methyl-3-iodophenylalanine, D,L-a-methyl-3-bromophenylalanine, D,L-α-methyl-3-chlorophenylalanine, D,L-α-methyl-3-fluorophenylalanine, mimosine, mimosinamine, mimosinic acid, 7-O-methylspinochrome B, 6-(3-hydroxybutyl)-7-O-methylspinachrome B, aquayamycin, chrothiomycin, frenolicin, fuscaric acid, pentylpicolinic acid, dopstatin, methylspinazarin, 6,7-dihydroxymethylspinazarin, 3-ethyl-α-methyltyrosine, 3-methyl-α-methyltyrosine, 3-isopropyl-x-methyltyrosine, 3-allyl-α-methyltyrosine, 3-[4-hydroxy-3-(2-methylallyl)-phenyl]-2-methylalanine,, 3-[3-(2,3-epoxypropyl)-4-hydroxyphenyl]-2-methylalanine, 3-isobutyl-α-methyltyrosine, 3-methylvinyl-α-methyltyrosine, 5-methyl-6,7-diphenyltetrahydropterin, 3-(2,3-dihydro-2,2-dimethyl-5-benzofuranyl]-2-methylalanine, 3-[2,3-dihydro-2,2-dimethyl-5-benzofuranyl]-2-methylalan ine, α-methyldopa, or ethyl-3-amino-4H-pyrrolo [3,4c] isoxazole carboxylate is a more efficacious antihypertensive agent than the free C moiety.

In addition, luminides which provide controlled extracellular release of biologically active substances such as drugs and proteins including enzymes and hormones are herein disclosed as macromolecular luminides. Luminides, each comprising a C functionality of a drug or protein such as insulin, erythropoietin, interleuken 2, interferon, growth hormone, atrial natriuretic factor, tissue plasminogen activator, an anti-inflammatory drug, an antihypertensive drug, an inotropic drug, a contraceptive drug, etc., are attached to a polymeric material to which an enzyme is immobilized to form a macromolecular luminide. The enzyme molecules react with molecules in the ambient extracellular environment at a rate in proportion to their concentration to produce peroxide or free radicals which react with the A functionality molecules causing them to achieve a high energy electronic state which is followed by the release of the C molecules where the release of C is in proportion to the ambient concentration of, the substrate of the enzyme.

For example, a macromolecular luminide which provides a release of insulin in proportion to the ambient glucose concentration comprises luminide molecules, each comprising a C functionality of insulin, covalently bound to a biocompatible polymer to which the enzyme glucose oxidase is immobilized. The immobilized enzyme reacts with glucose at a rate proportional to the ambient glucose concentration to produce peroxide which reacts with the A functionality molecules of the attached luminide molecules to effect release of insulin. Because the insulin release is in proportion to the glucose concentration this macromolecular agent represents a very effective diabetic therapy.

As an additional example, cardiac ischemia results in the production and release of degradation products of purines such as xanthine. The enzyme xanthine oxidase oxidizes xanthine and directly reduces oxygen to hydrogen peroxide. Furthermore, tissue plasminogen activator (TPA) is an effective agent for the treatment of myocardial infarction because this agent effects the lysis of fibrin clots in coronary arteries to establish reperfusion. Cardiac recovery is enhanced by diminishing the delay between the occlusion event and the administration of TPA. Thus, a macromolecular luminide comprising luminide molecules, each comprising a C functionality of TPA, bound to a biocompatible polymer to which xanthine oxidase is immobilized is an agent which releases TPA in proportion to the products of cardiac ischemia. Thus, it is a highly effective agent to resolve myocardial infarctions.

In another embodiment, luminide molecules, each comprising an A functionality which achieves a high energy electronic state via a reduction reaction, are attached to a conducting polymer to which an enzyme is immobilized. The immobilized enzyme oxidizes molecules in the ambient environment and transfers electrons to the conducting polymer which reduces the A functionality molecules directly or indirectly via the optional D functionality molecules to effect release of the C molecules.

In the latter embodiment, the conducting polymer derivatized with an enzyme, can be replaced with an electrocatalytic polymer which is reduced directly by molecules in the ambient environment and transfers the electrons to the luminide molecules to effect release of the C molecules. For example, polyvinylferrocene and poly-[N-(9,10-anthroquinone)- ethylenimine are conductive polymers and electrocatalytically oxidize glucose. Thus, a macromolecular luminide for the treatment of diabetes comprises a conducting polymer such as polyvinylferrocene to which glucose oxidase is optionally bound and to which luminide molecules are bound where the A functionality molecules of the polymer attached luminides achieve a high energy electronic state via a reduction reaction. The polymer is reduced when glucose oxidase accepts electrons from glucose and transfers them to the polymer. Or, the electrocatalytic polymer is reduced directly by glucose. The reduced polymer reduces the A functionality molecules directly or indirectly via the optional D functionality molecules to effect release of insulin molecules in proportion to the ambient glucose concentration.

Furthermore, macromolecular luminides can be directed to a specific extracellular target site such as an anatomical or biological compartment or organ by further attaching monoclonal antibody molecules to the polymer of the macromolecular luminide which bind to a molecule at the desired target site.

In addition to pharmaceutical agents, luminides also comprise pesticides including. herbicides, fungicides, miticides, nematocides, fumigants, growth regulators, repellants, defoliants, rodenticides, molluscicides, algicides, desicants, antehelmintics, and bactericides. These luminides can be obtained by one skilled in the art by combining the functionalities, A, B, and optionally, D, of energy donor, energy acceptor, and electron transfer functionality, respectively, with a C moiety which possesses pesticidal activity. C moieties include those that appear in *Chemical Week Pesticides Register,* Robert P. Ovellette and John A. King, 1977, McGraw-Hill Book Company (incorporated by reference) and analogues of these agents. Enhanced pesticidal effectiveness is acheived via improved delivery of these agents to their target receptors by way of luminide molecules which possess desirable properties such as increased permeance to the cells of the organism relative the free C moieties.

EXPERIMENTAL 2

Release Reaction

MTL 7-3 was tested for release of the nitrile group as free cyanide during the reaction of the isoluminol group with hydrogen peroxide as follows:

$1.2 \times 10^{-5}$ moles of 1, 5-di-(p-N-2-(N-(4-aminobutyl)-N-ethylisoluminol) -N-ethylaminophenyl)-1,5-bis-(p,N,N-dimethylaniline) -1,3-pentadiene was reacted with an excess of cyanide in a 4/4/1 DMSO/pyridine/$H_2O$ solvent. The solution was acidified to pH one and distilled under vacuum until gas no longer evolved. The product was split into six equal aliquots of approximately one milliliter volume. A volume of 0.1 ml of 1M NaOH was added to all aliquots. A volume of 0.05 ml of 3% hydrogen peroxide was added to 3 of the aliquots. After five minutes cyanide was assayed following the proceedure of Gunther and Blinn.

This proceedure involves the addition of acid to the sample which is heated to distill hydrocyanic acid which is captured in a basic solution to which a colorimetric reagent is added to develop a color which is compared to a standard curve. The results are as follows:

| Sample | Released cyanide (ug) |
|---|---|
| TEST ONE | |
| Blank | 0 |
| MTL 7-3 | 22.2 |
| MTL 7-3/$H_2O_2$ | |
| 26.4 | |
| TEST TWO | |
| Blank | 0 |
| MTL 7-3 | 21.5 |
| MTL 7-3/$H_2O_2$ | |
| 27.0 | |
| TEST THREE | |
| Blank | 0 |
| MTL 7-3 | 15.0 |
| MTL 7-3/$H_2O_2$ | |
| 30.5 | |

The release reaction test was repeated as follows: $4.5 \times 10^{-6}$ moles of 1,5-di-(p-N-2-(N-(4-aminobutyl)-N-ethylisoluminol) -N-ethylaminophenyl)-1,5-bis-(p-N,N-dimethylaniline) -1,3-pentadiene was reacted with excess cyanide in a 1:1 DMSO/$H_2O$ solvent. The solution was acidified to ph one and was distilled for 90 minutes under reduced pressure. The volume of the solution was made 4 milliliters by addition of $H_2O$. The solution was made basic by addition of 1M NaOH and was split into two equal volume aliquots. 0.05 milliliters of 3% $H_2O_2$ was added to one aliquot. Both aliquots stood for 5 minutes, and then cyanide was determined as previously described. The results are as follows:

| TEST FOUR | |
|---|---|
| Sample | Released cyanide (ug) |
| Blank | 0 |
| MTL 7-3 | 73.4 |
| MTL 7-3/$H_2O_2$ | |
| 109. 1 | |

The results indicate that cyanide was released as a result of a reaction of hydrogen peroxide with the luminide compound. The release of lesser amounts of cyanide during the control experiment is consistent with the thermochromic properties of the luminide compound at elevated temperatures as the samples were heated during the cyanide determination proceedure.

EXPERIMENTAL 3

Efficacy of Treatment of C3H Mice Infected with Raucher Spleen Focus Forming Virus with Luminide MTL J-1.

The effectiveness of MTL J-1 was tested in C3H mice against the virus RSFFV (Raucher Spleen Focus Forming Virus) which is a retrovirus and is a valid animal model for HIV infection by application to the above identified mice according to the following procedure:

Three groups of two month old C3H mice, each comprising four animals were provided as one control and two test groups wherein, the three groups (I-III) were subjected to an infectious dose of RSFFV on day one. The first group (I) served as control and received no treatment. Group II and III were treated with 10uM total body weight concentration of the drug Foscarn.et and the test compound MTL J-1, respectively which was administered each day for days 5 through 9. The animals were sacrificed on day 14, where upon the spleens where removed and weighed. The results are summarized in the following table:

TABLE 1

|  | I | II | III |
|---|---|---|---|
| Ending Weight (grams) | 21.1 | 21.2 | 22.5 |
| Weight change (grams) | 1.675 | 0.15 | 2.25 |
| Spleen weight Normalized (grams) | .083 | .079 | .068 |

The tests were redone with a second control group (IA) having no infection of RSFFV and receiving no treatment with any drug, wherein groups I and IA comprise four mice each, and groups II and III comprise five mice each, providing the results summarized below:

TABLE 2

|  | IA | I | II | III |
|---|---|---|---|---|
| Ending Weight (grams) | 18.5 | 18.6 | 19.6 | 19.2 |
| Weight change (grams) | +1.0 | +1.8 | +1.6 | +1.5 |
| Spleen weight Normalized (grams) | 0.046 | 0.060 | 0.061 | 0.049 |

These results indicate that MTL J-1 was nontoxic as demonstrated by an absence of weight loss and that MTL J-1 was highly effective as demonstrated by the absence of splenomegaly in the animals administered this compound.

The biologically active substances not specifically mentioned are included in, and functionally applicable as a drug in the compound of the present invention. Also, the references referred to herein or filed herewith are hereby incorporated by reference. Modifications and substitutions made by one of skilled in the art are considered to be within the scope of the present invention, which is not to be limited except by the claims.

APPENDIX I

Triphenyl Methanes

Triphenyl methane dyes have been known and used for many years. Consequently many general-type syntheses have been worked out and published. The following four synthesis methods have been used almost exclusively for the 15 triphenyl methane dyes synthesized.

Method A. Michler's Ketone Method

To equal molar quantities of a p-amino benzophenone or di-(p-amino) benzophenone (Michler's type ketones) and aromatic amines, such as anilines and naphthyl amines, sufficient toluene-phosphorous oxychloride solution is added (3–5) to dissolve the reactants at 50° C. The temperature is raised to 80° C. and the solution is stirred for approximately 45 minutes or until the mass becomes very viscous. The sample is cooled and 10 ml of water added for each ml of phosphorous oxychloride used, and heated to boiling. The solution is cooled and treated with 6N sodium hydroxide solution until the pH is 8 or more. The sample is steam-distilled to removed the last trace of any toluene or steam volatile unreacted amine. It is cooled and the aqueous phase poured off. The organic phase is dissolved in hot methanol-acetic acid (1:1) solution. The sodium salt of the anion for the dye form desired is then added.

The sample is cooled and ether added slowly, while stirring to effect crystallization of dye.

This method varies slightly from the known published methods, but has been found to have several advantages for laboratory preparation of dyes of the types:

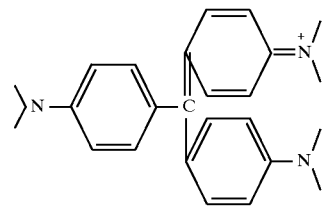

where any one of the phenyl groups may be replaced by a naphthyl group.

Method B. Michler's Hydrol Method Part 1.

Triphenylmethane type compounds may be produced by the condensation of a diphenyl substituted secondary alcohol and an aromatic ring. The secondary alcohol is of a type called Michler's hydrol of the general type formula:

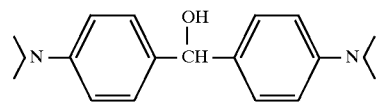

which is produced by the controlled reduction of the corresponding ketone with sodium amalgam in alcohol alcohol-water mixture, dried, and stored in a vacuum dessicator.

The hydrol is then condensed with the desired substituted benzene ring of the general-type formula:

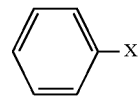

in concentrated sulfuric acid and at a temperature below 60° C. for several hours. The reaction mixture is diluted with water and the acid neutralized until the condensation product is precipitated out. The product has the general-type formula:

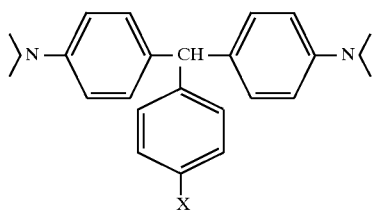

Part 2

The condensation product is then oxidized with lead peroxide in an acidic-aqueous media to the general-type formula:

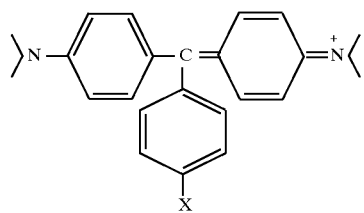

Any excess lead peroxide is neutralized with sodium carbonate. The lead is precipitated with sodium sulfate and filtered off. The acid is neutralized to a pH of 7 and the dye salted out as the chloride or as the zinc chloride double salt.

This method was found to be useful in preparing triphenyl methane dyes where one of the phenyl groups is to have substituents other than an amino group.

APPENDIX II

Method C. Aniline - Benzaldehyde Method

Under reflux, a two-mole quantity of an aniline and one mole of a benzaldehyde is heated with zinc chloride as a catalyst to produce the true leuco form of the desired dye.

A stoichiometric quantity of lead dioxide paste and hydrochloric acid is added to a weighed quantity of the leuco dye. This is stirred for 30 minutes and then filtered. Sodium sulfate is added to precipitate any soluble lead salts, which is then filtered and the filtrate neutralized. A neutral salt is added to salt out the dye. (The salt chosen for salting out will depend on the anion form of the dye desired.)

Method D. Alkyl Halide Method

Dyes of the type

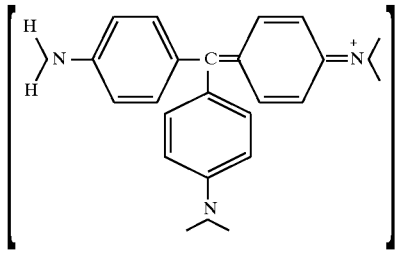

may be reacted with alkyl iodides in an alkaline methanol solution to replace the hydrogen on each amino group with the alkyl group of the alkyl iodide to yield dyes of the type:

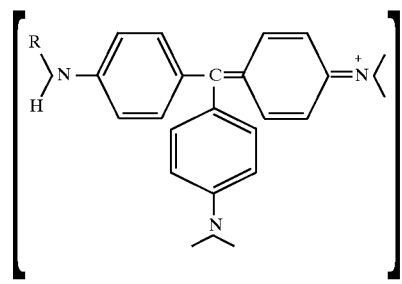

of the 15 triphenyl methan dyes synthesized, 6 were found to be phototropic and were previously tabulated under 3.2.6.1. For the other nine dyes, no phototropic systems have yet been developed.

Polymethines

Polymethines (refs. 13, 18, 19) may be classified generally by the degree of symmetry around the conjugated carbon chain. If we represent the polymethines by the general formula:

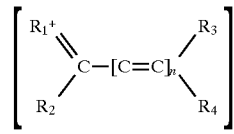

we may further classify the dyes on the basis of the identify of the various R groups. It is prerequisite to this family that at least two of the R groups be capable of extending the conjugation of the chain by accepting a positive charge,

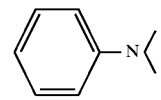

being such a group.

Where $R_1$ and $R_4$ meet the prerequisite of the family and either $R_2$ or $R_3$ or both are hydrogen, the dyes may be prepared by methods I and II of the four general methods given in the succeeding pages.

Where $R_4$ is hydrogen and $R_1$, $R_2$ and $R_3$ are other than hydrogen and at least two of them meet the prerequisite of the family, the dyes may be prepared by methods I or IV.

Where none of the R's are hydrogens, the dyes may be prepared by methods II or III; the choice of method will depend on the value of n and the degree of symmetry desired. When the value of n is to exceed 1, method III cannot be used. Method III has the advantage of giving any choice of symmetry from totally unsymmetrical to totally symmetrical, but the value of n is limited to 1.

Method I. Reaction of a p-aminophenyl alkene and a P-aminophyenl alkene aldehyde Equimolar quantities of a p-aminophenyl alkene of the class

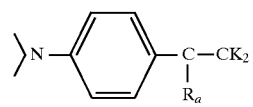

(where $R_a$ can equal H, aryl, alkyl, or arylamine groups) and p-aminophenyl alkene aldehyde of the class

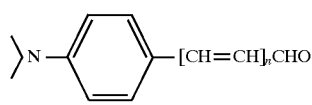

WHERE N = 0,1

(where n=0,1) are allowed to react in a nonaqueous solvent with an acid catalyst such as acetic acid, or acetic anhydride, and the acid of the desired dye form. The reaction mixture is allowed to stand for 5 days at room temperature. This is poured into water and neutralized until the dye precipitates. The precipitate is filtered off, dried, and recrystallized from anhydrous alcohol. This will produce a dye of the general-type formula as depicted below:

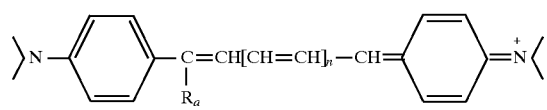

Method II. Reaction of p-Aminophenyl alkene and an Orthoester

Method IIa. (for compounds having 5 or more methine carbon atoms)

Two molar proportions of a p-aminophenyl alkene of the class

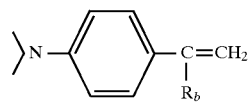

(where $R_o$ can equal H, aryl, alkyl, or arylamine group) with one mold of an orthoester of the class

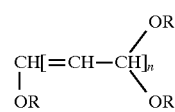

WHERE N = 0,1,2, OR 3

(where m=O, 1, 2, or 3) are allowed to react in a nonaqueous solvent, containing an acid catalyst such as acetic anhydride and the acid to form the desired carbonium compound. The reaction mixture is allowed to stand at room temperature for several hours. Ether is added to precipitate the dye. The precipitate is filtered and washed with ether or an ether-polar solvent mixture. The precipitate is dried in vacuum. This will produce a compound of the general-type formula as pictured below:

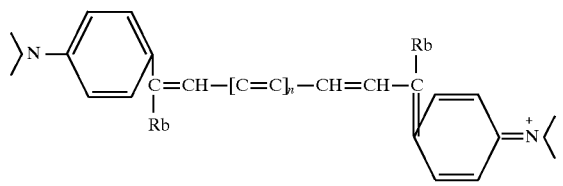

(where n=0, 1, 2, 3, or 4).

Method II*b*

By substituting tetramethyl ortho carbonate for the orthoester of method IIa and by increasing the p-aminophenyl alkene to a molar proportion of three, a new type of compound was prepared, having the general structure:

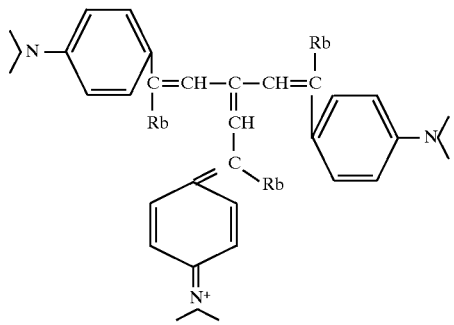

A nitrogen determination on

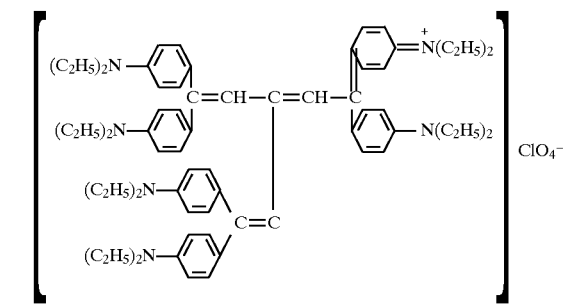

using a Coleman nitrogen analyzer found 8.58 percent nitrogen (theoretical 8.61).

Method III. Reaction of a Ketone and a 1-(P-Aminophenyl)-1-(R) Alkene

A ketone of the general-type formula

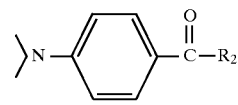

is refluxed with a substituted alkene, of the general-type formula

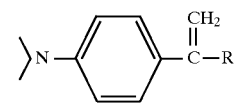

where R is something other than hydrogen with phosphorous oxychloride as the solvent catalyst. At the end of the reflux, the reaction mixture is cooled and poured into water and treated with a salt of the acid to yield the desired anion form of the dye. The aqueous mixture is neutralized with solid sodium acetate until the dye precipitates.

This method yields a dye of the general-type formula

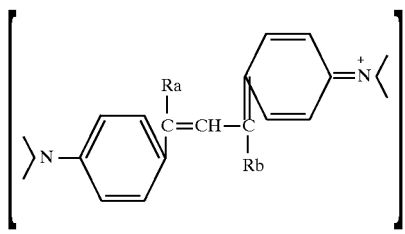

where $R_a$ and $R_b$ may be equal or different.

Method IV. Reaction of a Ketone and a p-Aminophenyl Alkene

A ketone of the general-type formula

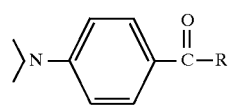

is refluxed for 5 hours with a substituted alkene of the general-type formula

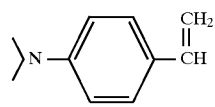

with phosphorous oxychloride as a solvent catalyst. At the end of the 5-hour reflux time, the reaction mixture is cooled and poured into water and treated with a salt of the acid to yield the desired anion form of the dye. The aqueous mixture is neutralized with solid sodium acetate until dye precipitates.

This method yields a dye of the general-type formula:

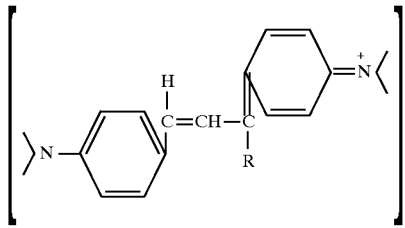

where $R_a$ and $R_b$ may be equal or different.

Organic Synthesis Procedures

Method No. 1: Polymethine dyes
Example: Preparation of dye PP 2109

Step A: Preparation of p-Fluorobenzanilide

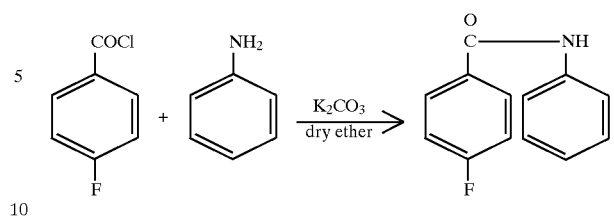

A solution of aniline, 23.7 g (0.255 mole) in 250 ml of dry ether containing 55.3 g of potassium carbonate was heated to reflux temperature. To the refluxing mixture, 50 g (0.32 mole) of p-fluorobenzoyl chloride was added over a period of one hour. The reaction mixture was refluxed for four hours and the ether distilled off. Cold water was added to the residue and the p-fluorobenzanilide collected by filtration. Yield: 64 g, metling point 196° C., white crystalline powder.

Step B. Preparation of p-N,N-Di-n-propylamin-p-fluorobenzophenone

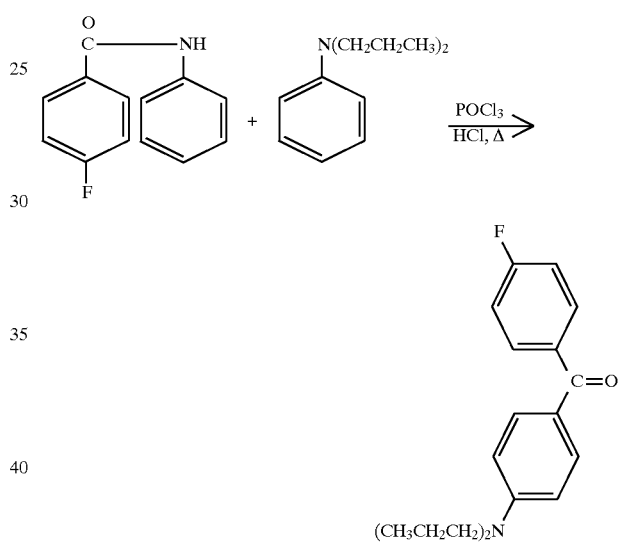

64 g (0.3 mole) of dry, powdered p-fluorobenzanilide, 100 g (0.6 mole) of N,N-di-n-propylaniline, and 55 ml of phosphorous oxychloride were mixed in a 500 ml three-necked flask fitted with a stopper, a thermometer and a reflux condenser having a $CaCl_2$ drying tube on top. The reaction mixture was warmed gently until the temperature reached 100°–112° C., at which point an exothermic reaction occurred and the temperature rose to 160° C. As soon as the exothermic reaction was noted, the mixture was immediately cooled by swirling the flask in ice water. The cooling was continued until the temperature dropped to 100°–105° C. This temperature range was held for three hours. The reaction mixture was then hydrolyzed in a three liter beaker by the addition of 58 ml concentrated hydrochloric acid in 445 ml water. The reaction mixture was allowed to stand for eight to twelve hours to complete the hydrolysis. An additional 4100 ml of water was then added to precipitate the ketone formed. This was filtered, washed thoroughly with cold water, reslurried and refiltered. Yield: 45 g, light green sandy crystals, melting point 85°–87° C.

Step C: Preparation of 1-(4-N,N-Di-n-propylamino-phenyl)-1-(4-fluorophenyl) ethylene

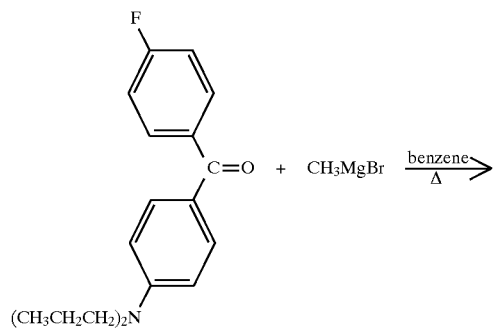

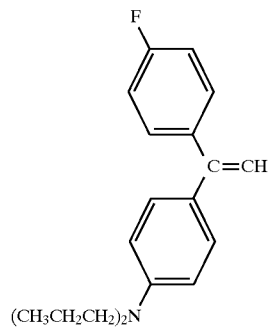

Sixty ml of a 3 molar etherial solution of methyl magnesium bromide was evaporated almost to dryness under reduced pressure in a 500 ml three-necked flask equipped with thermometer and nitrogen sparger. The grey moist residue was suspended in 75 ml of dry benzene. The flask was then equipped for refluxing by the addition of a condenser fitted with a $CaCl_2$ drying tube and an addition funnel. A 0.1 mole portion of the ketone dissolved in 250 ml of boiling benzene was then placed in the addition funnel and added dropwise to the warmed methyl magnesium bromide-benzene slurry over a half-hour period. The resulting reddish solution was refluxed for three hours. The termination of the reaction was indicated by the fading of the initial reddish color to a pale yellow. The reaction mixture was then cooled to room temperature and cautiously treated with 45 ml of saturated ammonium chloride solution. This mixture was filtered and the filtrate boiled with 0.1 g of p-toluenesulphonic acid until the evolution of water was completed. The acid contained in the reaction mixture was then removed by the addition of 0.5 g of sodium bicarbonate. The volume was reduced to one half by evaporation under reduced pressure. Five hundred ml of dry ethanol was added to the remaining solution, which was then allowed to cool with the subsequent precipitation of the ethylene compound.

The precipitate was filtered, washed with 50 ml ice cold ethanol, and the crystals dried in a vacuum oven. Yield: 86 percent of theory: melting point 101°–102° C.

Step D: Preparation of a perchlorate of 1,5-di-(p-fluorophenyl)-1,5-bis-(p-N,N-di-n-propylanilino)-1,3-pentadiene

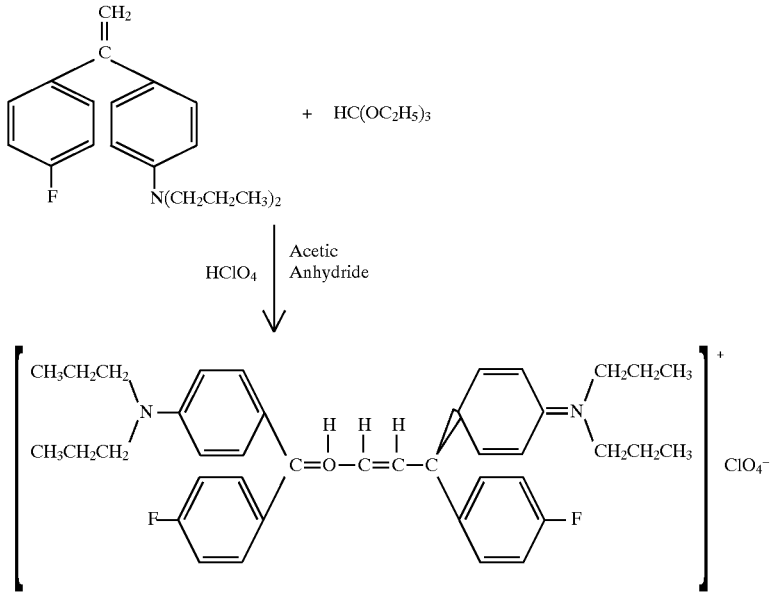

A mixture of 23.6 g (0.08 mole) of 1(4-N,N-di-n-propylaminophenyl)-1-(4-fluorophenyl)ethylene, 12 ml of ethyl orthoformate and 50 ml of acetic anhydride was treated with an ice-cold solution of 4 ml of 72 percent perchloric acid dissolved in 50 ml of acetic anhydride. The resulting dark red solution was heated in a water bath at 85° C. for one hour, after which another 12 ml of ethyl orthoformate was added. The mixture was than allowed to stand at room temperature for 18 hours to precipitate the condensation product. The precipitate was collected and washed with acetic acid, ethanol and ether. Yield: 68 percent based on perchloric acid, golden brown crystals melting with decomposition at 277° C. Method No. 2: Polymethine dyes Example: Preparation of dye PP 2110 Step A: Preparation of 3-Amino-4-methoxy-4'-N,N-Dimethylaminobenzophenone

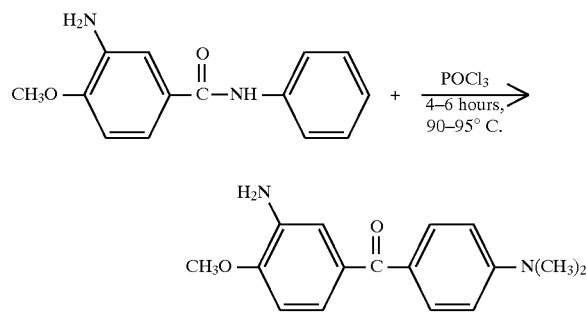

Fifty grams (0.2 mole) of 3-amino-4-methoxybenzanilide, 70 g (0.58 mole) N,N-dimethylaniline and 36 g $POCl_3$ were heated on a water bath at 90° C. to 95° C. for 4 to 6 hours. The product was then cautiously poured into a solution of 23 ml of concentrated hydrochloric acid in 250 ml water. The resulting solution was warmed at 80° C until the initial reddish color disappeared, indicating that the aniline was completely hydrolyzed. A liter of water was added to precipitate the ketone, which was filtered, washed with cold water, and recrystallized from a 2:1 aqueous alcohol solution. Yield: 38 g of slightly yellowish crystals, metling point 82° C.

Step B: Preparation of 1(4-N,N-Dimethylaminophenyl)-1-(3-amino-4-methoxyphenyl)ethylene

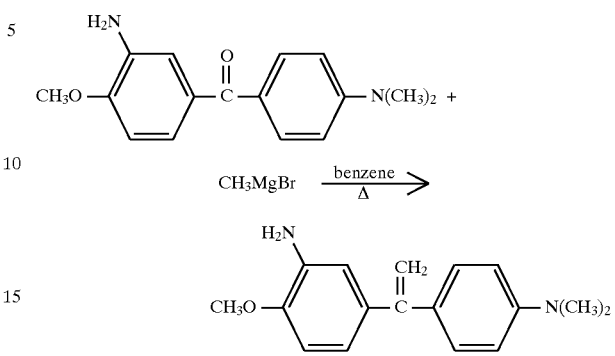

Fifty ml of a 3 M ethereal solution of methyl magnesium bromide was evaporated almost to dryness under reduced pressure. Dry nitrogen was admitted to the reaction flask and the gray residue was suspended in 75 ml of dry benzene. The slurry was warmed, then 26.6 g (0.1 mole) of the ketone compound dissolved in 250 ml boiling benzene was added over a 15-minute period. The resulting solution was refluxed until the pale yellow color faded to colorless (45 minutes). The mixture was cooled and treated with 50 ml of a saturated $NH_4Cl$ solution. The colorless solution was filtered through a folded filter paper without applying vacuum and in the absence of strong light. The filtrate was boiled with 0.1 g p-teluenesulfonic acid until the evolution of water was complete. The cooled solution was neutralized by the addition of 0.2 g dry $NaHCO_3$ and then reduced to ¼ volume by evaporating the solvent under reduced pressure. The remaining solution was diluted with 250 ml of dry ethanol and the ethylene product allowed to precipitate over 12 hours. Yield: 34 percent of theory, yellow hygroscopic flakes, melting point 118° C.

Step C: Condensation Reaction Leading to Dye (A perchlorate of 1,5-di-(3-amino-4-methoxyphenyl)-1,5-bis-(p-N,N-dimethylaniline)-1,3-pentadiene.

A mixture of 26.9 g (0.1 mole) of 1(4-N,N-dimethylaminophenyl)-1-(3-amino-4-methoxyphenyl) ethylene, 15 ml of ethyl orthoformate and 45 ml acetic anhydride was treated with a solution of 4 ml of 72 percent perchloric acid and 40 ml acetic acid previously cooled to 0° C. The resulting mixture was allowed to stand at room temperature for 5 days, after which it was treated with 25 ml of ether and kept an additional day at room temperature. The precipitate formed was filtered and washed with acetic acid, ethanol, and ether, and dried in a vacuum dessicator.

Product: sandy crystals, dark brown, melting point 209°–210° C.

Note: The reaction should be run at room temperature. Condensation at elevated temperatures yields a black, insoluble polymerization product.

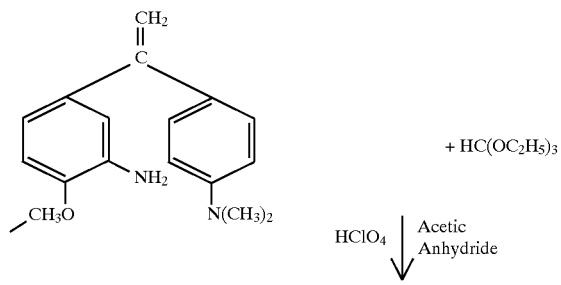

-continued

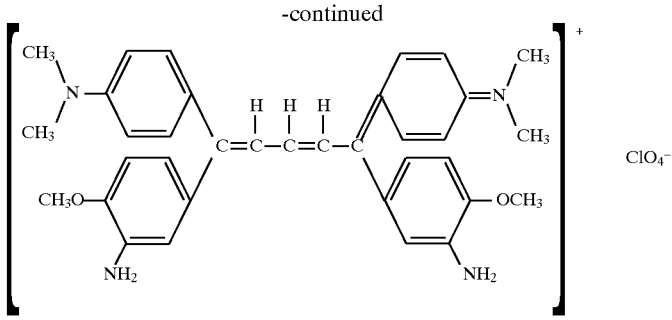

APPENDIX III

Azo Polymethines

Dyes of the general structural type

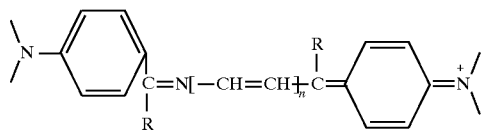

are prepared by condensation of p-aminophenyl alkene aldehydes or ketones with auramine-type hydrochlorides. One such dye was prepared:

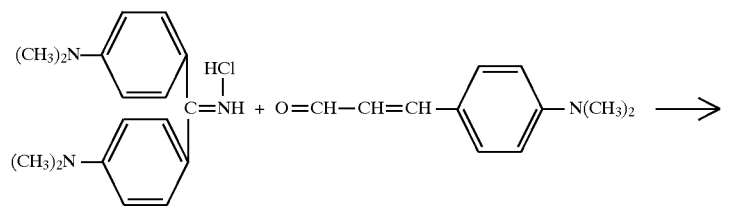

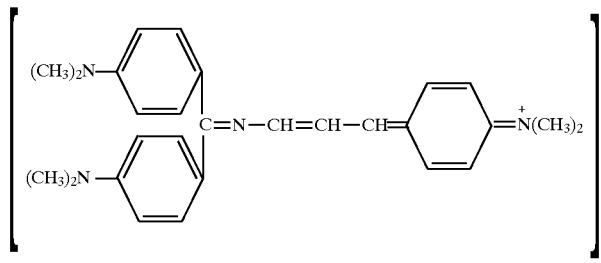

1,1,5-tris-4(N,N-dimenthyamino)phenyl-2-azo, pentene carbonium chloride which showed only very slight yellow phototropy.

APPENDIX IV

Diazo Polymethines

A new type of dye, believed to have the general structures,

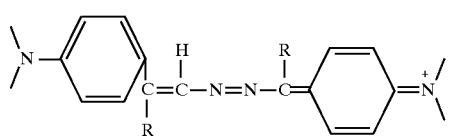

was prepared by nitrosation of auramine-type structures

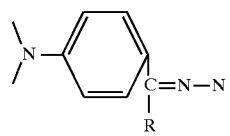

with nitrous acid to yield

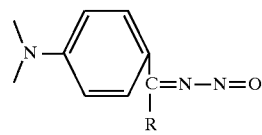

This is then reacted with p-aminophenyl alkenes to yield structures of Type A. Confirmation of structure is incomplete, but significant to this work is that the above series of reactons yield phototropic materials.

The position of the -N-N- group in the carbon chain may be changed to occupy the 1 and 2 positions, as well as the above shown 2 and 3 petitions, by using a secondary amine in place of B in the above series of reactions. With nitrogen atoms in the 1 and 2 positions, the 1 position nitrogen becomes a quaternary ammonium atom in one of the resonance states of the molecule.

One dye of each of these types was prepared. Both were found to phototropic. They are:

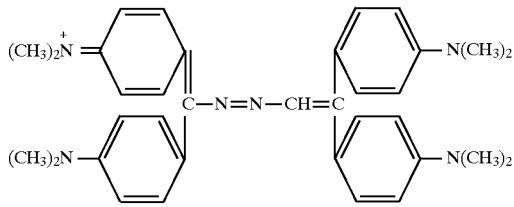

1,1,5,5-tetrakis-[4-(N,N-dimethylamino)phenyl]-2,3-diazo pentene carbonium (Code PP2031)

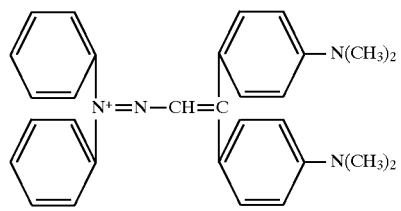

1,1-bux-[4-(N,N-dimethylamino)phenyl-3,4-bis-(phenyl)]-3,4-diazo butene carbonium (Code PP 2030)

APPENDIX V

Quaternary Ammonium Salt Polymethines

Three dyes of the type

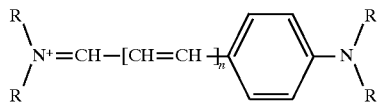

were prepared and tested for phototropy.

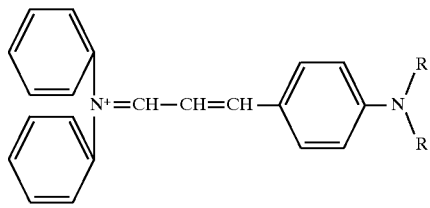

N-(p-dimethylamino cinnamylidine)-N,N-diphenyl ammonium proved to be phototropic but broke down rapidly under ultraviolet light

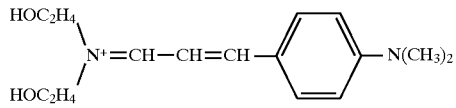

N-(p-dimethylamino cinnamylidine)-N,N-diethanol ammonium, and

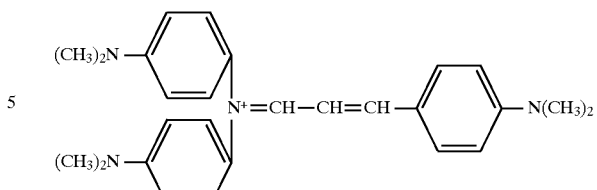

N-(p-dimethyl amino cinnamylidine) N,N-di-4(N,N-dimethylamino)phenyl ammonium were not phototropic.

The dyes where prepared by the condensation of dimethylamino cinnamic aldehyde with the hydrochloride of secondary amines in warm, anhydrous alcohol according to the method of Brooker.

APPENDIX VI

Intermediates

Although most types of dye intermediates are available, specific compounds necessary to this work were not available on the commercial market. It was necessary to synthesize 13 such intermediates.

The syntehsis or type synthesis of these intermediates are for the most part given in standard works on synthesis dyes and dye intermediates.

The synthesis of tetramethyl orthocarbonate and ethylenes of the type are reported herein.

Synthesis of Tetramethyl Ortho Carbonates

To 500 grams of cold dry methanol under reflux, 80 grams of metallic sodium in large pieces are added. (The alcohol solution has to be cooled externally with ice water to prevent loss of methanol through the reflux condenser.) Before all of the sodium has dissolved, 100 grams of chloropicrin that has been diluted with 200 ml of methanol is slowly dropped in. The solution is refluxed for one hour. The methanol is distilled off until the residue seems almost dry. This is then dissolved in 600 cc of water, and the aqueous solution is extracted with three 200-ml portions of ether. The composited ether extracts are dried over calcium chloride. The ether is fractionated from the dried solution and a little sodium methoxide in methanol is added to the residue to react with any unreached chloropiorin. This is allowewd to stand overnight. The solution is fractionated, collecting one fraction between 110°–115° C.

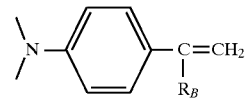

Methyl magnesium bromide in ethyl ether is placed into a round bottom flask equipped with a condenser and an addition funnel. The ether is distilled off, and the methyl magnesium bromide then taken up with anhydrous benzene. A ketone is dissolved in anhydrous benzene and added dropwise to the Grignard reagent with continuous heating. After the addition is completed, the mixture is refluxed for three more hours. After cooling, sufficient ammonium chloride solution (saturated aqueous solution) is very carefully added in order to dissolve any free magnesium. The Grignard complex is decomposed with hydrochloric acid. After decomposition of the complex is complete, the solution is allowed to come to room temperature. After making sure the solution is alkaline to phenolphthalein, the benzene solution is decanted off of the solids. The solids are washed with two 50-ml positions of ether and the washings combined with the benzene solution. The ether-benzene solution is dried over anhydrous sodium sulfate.

The ether and benzene are then distilled off leaving a residue. This residue is vacuum-distilled at 2–5 mm of Hg.

APPENDIX VII

Method No. 3: Indoline base dyes Example: Preparation of dye PP 1210 Step A: Synthesis of p-[N-(2-chloroethyl)-N-ethyl]aminobenzaldehyde

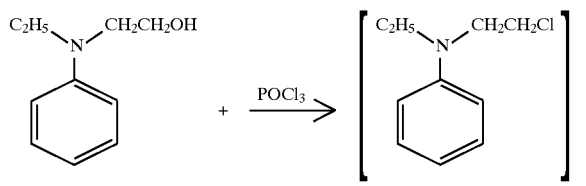

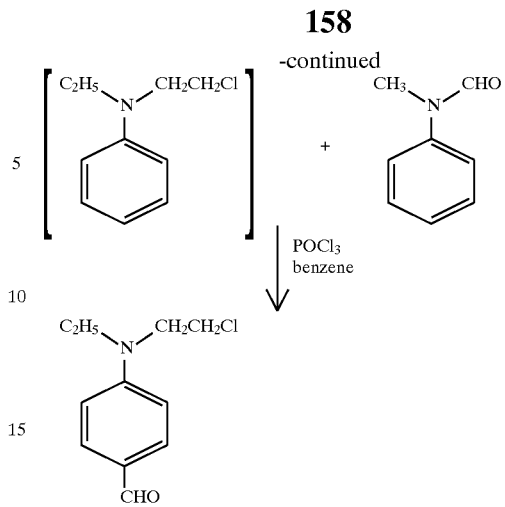

At 50° C. 82.5 parts by weight of N-(2-hydroxyehtyl)-N-ethylaniline were added dropwise to 90 parts by weight of phosphorous oxychloride. The solution was then heated at 90° C. for 6 hours. After colling to 0° C., a mixture of 150 parts by weight of N-methylformanilide, 170 parts by weight of phosphorus oxychloride, and 120 parts by weight of benzene was added to the above solution. The mixture was heated for a few hours at 30°–35° C. After neutralization with an aqueous solution of sodium hydroxide, the benzene solution of the aldehyde product was separated. After evaporating the benzene, p-N-chloroethyl-N-ethylamino benzaldhyde remained as a slightly yellow oil which hardened on standing and could be recrystallized from ethanol. The recrystallized aldehyde had a white flaky appearance and a melting point of 283° C.

Step B: Synthesis of dye PP 2120, Chloride of 2,3,3-trimethyl-2-[p-(N-2-chloroethyl-N-ethyl)amino-β-s tyryl] indoline.

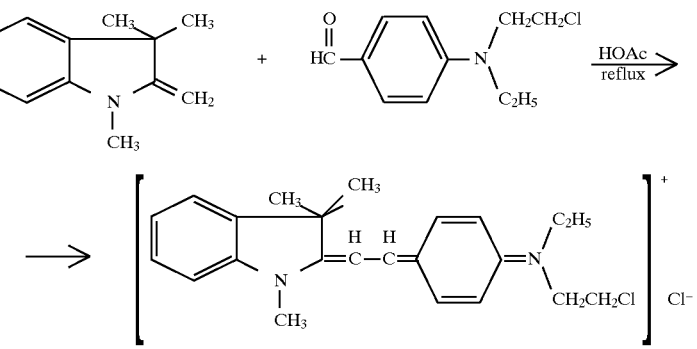

p-(N-Chloroethyl-N-ethyl)amino benzaldehyde (12.5 parts by weight) was refluxed for 6 hours at 100° C. with 8.5 parts by weight of 1,3,3-trimethyl-2-methlyene-indoline in 60 parts by weight of glacial acetic acid. The mixture was then poured into water and the condensation product was salted out with sodium chloride. The crude dyestuff was obtained as a dark bronze resinous liquid which hardened upon standing and could be crushed into shiny bronze particles. The pure dye was obtained by recrystallization from hot water, m.p. 167°–168° C.

APPENDIX VIII

Method No. 4: Dyes with more than one chromophore Example: Preparation of dye PP 2131
Step A: Synthesis of phenetolazobenzaldehydsulphonic acid One hundred grams of Chrysophenin G concentrate, which was equivalent to about 92 grams of the pure compound, was dissolved in 6 liters of boiling water. The solution was cooled to 0°–5° C. by the addition of ice and then saturated with sodium chloride.

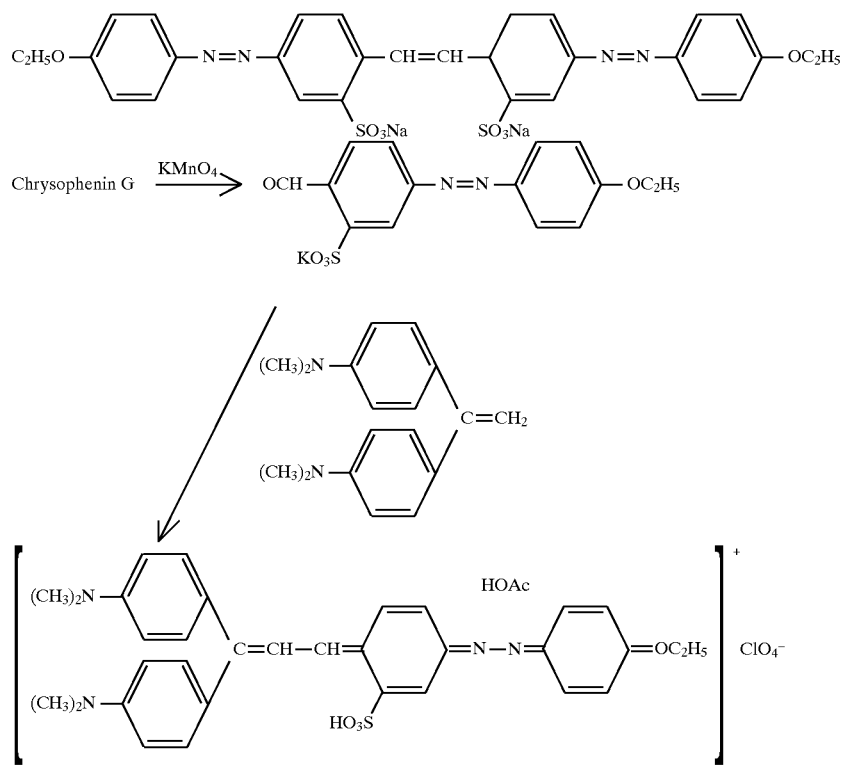

A 3 percent solution of potassium permanganate was slowly added with vigorous agitation until a pale pink color persisted. (The quantity of permanganate required was 29 grams.) The precipitate which formed during the reaction was allowed to settle and was collected by siphoning off the supernatant liquor. The product was isolated by boiling the precipitate two or three times with one liter of water, filtering off the manganese dioxide and adding potassium chloride to the hot water solution until precipitation was complete. An additional small quantity of aldehyde was isolated by salting it out of the supernatant liquor with potassium chloride. The product precipitated from water in orange-colored microscopic needles.

Step B: Synthesis of Dye PP 2131, perchlorate of 1,1-bis-(p-N,N-dimethylamino)phenyl-3-[2-sulfonato-4-(p -ethoxyphenylazoo] phenyl propene.

Phenetoleazobenzaldehyde sulphonic acid (1.86 parts by weight) was refluxed for 6 hours at 100° C. with 1.33 parts by weight of 1,1-bis-(4-N,N-dimethylamino)phenyl ethylene is 25 parts by weight of glacial acetic acid. The condensation product was then poured into water and salted out. The dyestuff was obtained as a thick dark green liquid which hardened upon standing to a crushable solid, melting point 78°–92° C. An attempt to recrystallize the dye using a variety of solvents was unsuccessful.

APPENDIX IX

Example 1 - Xylene Blue VS cyanide

To a solution of 25 g. of commercial Xylene Blue VS, Colour Index No. 672, in 150 ml. of water is added 4.5 g. of 95% sodium cyanide and the mixture is heated in a pressure bottle for 1 hour. Suitable precautions should be taken to avoid cuts by glass wet with sodium cyanide solution in the event of the explosion of the bottle. The solution is then cooled, allowed to stand for 1 day at 25° C. and filtered from the precipitated Xylene Blue VS cyanide disodium salt having the formula

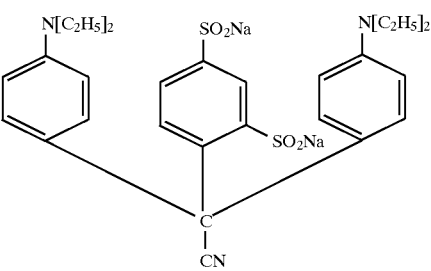

The disodium salt is readily soluble in water to yield a colorless solution that slowly becomes blue on exposure to radiation of wave length 2537 A. The color change is much slower than with a solution of a representative basic dye cyanide, such as malachite green syanide in alcohol, and thus is useful in the actinometry of more intense radiation.

The free acid form of Xylene Blue VS cyanide, having the formula

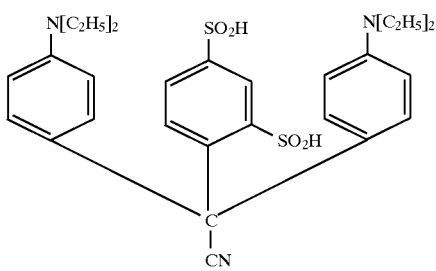

may be prepared by treatment of a solution of 11 g. of the disodium salt in 100 ml. of water with 11.2 ml. of concentrated hydrochloric acid. After the mixture has stood at room temperature for 2 days, the colorless precipitated from acid is collected on a filter, washed with water, and air dried. It is sparingly soluble in water. A dilute, colorless, aqueous solution of the free acid color blue on ultra-violet irradiation at a speed intermediate between that of the solutions of the sodium salt and of alcoholic solutions of malachite green cyanide.

The barium salt of Xylene Blue VS cyanide having the formula

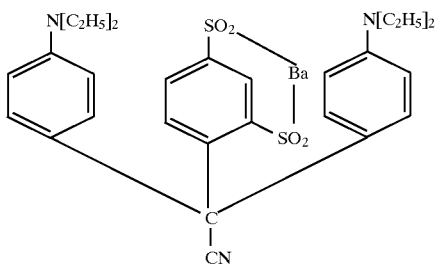

may be prepared by neutralization of a hot ½ of 1% aqueous solution of the free acid to pH 3.4 with N10 barium hydroxide solution. The neutralized solution is cooled to room temperature, allowed to stand for 3 days, and filtered from the colorless, crystalline barium salt. The barium salt is less soluble in water than the free acid, but quite sufficiently soluble to give photosensitive solutions that behave on exposure to ultra-violet like solutions of the sodium salt.

References

1. Schuster, G.B., Schmidt, S.B., *Bioluminescense and Chemiluminescence,* edited by Marlene A. Deluca and William D. McElroy, (1981), pp. 23–29.
2. Berger, A.W., et al., Photochemistry and Photobiology, Vol. 4, (1965), pp. 1123–1127.
3. Philbrook, G.E., et al., Photochemistry and Photobiology, Vol. 4, (1965), pp. 1175–83.
4. White, E.H., et al., Photochemistry and Photobiology, Vol. 4, (1965), pp. 1129–55.
5. Philbrook, G.E., et al., Photochemistry and Photobiology, Vol. 4, (1965), pp. 869–76.
6. Rauhut, M.M., et al., Photochemistry and Photobiology, Vol. 4, (1965), pp. 1097–1110.
7. McCapra, F., et al., Photochemistry and Photobiology, Vol. 4, (1965), pp. 1111–1121.
8. McCapra, F., et al., Chemical Communications, No. 15, (1966), pp.522–23.
9. Gorsuch, J.D., "Studies of the Chemiluminescence of Luminol," M.I.T. Ph.D. Thesis, 1969.
10. Legg, K.D., "The Chemiluminescence of Lucigenin," K.I.T. Ph.d. Thesis, 1969.
11. Lytle, F.E., "Chemiluminescence and Photoluminescence of Ruthenium Chelates," M.I.T. Ph.D. Thesis, 1968.
12. Allen, R.C., *Chemical and Biological Generation of the Excited State,* edited by Adam Waldeman, 1982, pp. 309–45.
13. Bowen, E.J., "Chemiluminescence in Solutions," in *Luminescence in Chemistry,* Edited by E.J. Bowen, D. Van Nostrand Co. Ltd, London; (1968) pp. 183–190.
14. Tuemmler, W.B., and Widi, B.S., J Amer Chem Soc, Vol. 80, (1958), pp. 3772–75.
15. Mac Nair, R.N., Photochemistry and Photobiology, Vol. 6, (1967), pp. 779–97.
16. Chalkley, L., U.S. Patent No. 2,885,303, (1958).
17. Chalkley, L., U.S. Patent No. 2,936,235, (1957).
18. Chalkley, L., U.S. Patent No. 2,829,148, (1958).
19. Chalkley, L., U.S. Patent No. 2,839,542, (1958).
20. Chalkley, L., U.S. Patent No. 2,839,543, (1958).
21. Brown, Glenn, *Photochromism,* pp. 294–375.
22. Wilkinson, F., "Intramolecular Electronic Energy Transfer Between Organic Molecules," in *Luminescence in Chemistry,* Edited by E. J. Bowen, D. Van Nostrand Co. LTD., London, (1968), pp. 154–182.
23. Lippman, R.D., *Bioluminescence and Chemiluminescence,* Edited by Marlene A. Deluca and William D. McElroy, (1982), pp. 373-81.
24. Dreyer, J.F., "Self-Attenuating Ophthalmic Filter," Rept. WADD-TR-60-632 Feb., 1961. AD 322820.
25. Dreyer, J.F., Harries, R.W., MacNair, R.N., Feldman, D., "Investigation of Materials and Systems for Protection Against Flash Blindness Effects of Nuclear Detonations," Rept. 68–38-CM, AD 688692.
26. Polacoat, Inc., "Development of a Means to Provide Protection for Eyes Against the Dazzle Effects of Nuclear Detonations," Quart. Rept. No. 5 on Contract DA-19-129 qm-1534, April 1961, AD 446865; also AD 447113 and 298225.
27. Van Dyke, K., *Bioluminescence and Chemiluminescence,* Vol. 1, CRC Press, Inc., 1985, pp. 1–42.
28. Zaklike, K.A., et. al., Photochemistry and Photobiology, Vol. 30, (1979), pp. 35–44.
29. Schaap, A.P., Burns, P.A., and Zaklika, K.A., J. Am. Chem. Soc., 99 (1977), pp. 1270–1272.
30. D'Iorio, A., Mavrides, C., Canadian Journal of pp. 1779–1784.
31. Vrang, L.,. Oberg, B., Antimicrobial Agents and Chemotherapy, (1986), 29, pp. 867–872.
32. Schnebli, H.P., et. al., Journal of Biological Chemistry, (1967), Vol. 242, pp. 1997–2004.
33. Roberts, E., Biochemical Pharmacology, (1974), Vol. 23, pp. 2637–2649.
34. Rando, R., Bangerter, F. W., Journal of the American Chemical Society, (1976), Vol. 98, pp. 6762–6764.
35. Tunnicliff, G., et. al., Experientia, (1977), Vol. 33, pp. 20–22.
36. Kobayashi, K., et. al., Febs Letters, (1977), Vol. 76, pp. 207–210.
37. Medicinal Chemistry A Biochemical Approach, Thomas Nogrady, (1985) Oxford University Press, N.Y., N.Y., pp. 193–203.
38. Jung, J.M., Metcalf, B.W., Biochemical and Biophysical Research Communications, (1975), 67, pp. 301–306.
39. Rando, R., Bangester, F.W., Biochemical and Biophysical Research Communications, (1977), Vol. 76, pp. 1276–1281.
40. Buu, N.T., Van Gelder,, N.M. Br. J. Pharmac, (1974,), 52, pp. 401–406, 41. *Enzyme Inhibitors,* edited by Urs Brodbeck, (1980) pp. 85–95.
42. *Enzyme Inhibitors,* ed. by Urs Brodbeck, (1980), pp. 61–74.
43. *Drug Action* and *Design: Mechanism Based Enzyme Inhibitors,* ed. by Kalman,, (1979), pp. 13–27.
44. Fuller, R.W., Nagarajan, R., Biochemical Pharmacology, (1978) pp. 1981–1983.
45. Barchardt, R.T., Wu, Y.S., Journal of Medicinal Chemistry, (1975), 18, pp. 300–303.
46. Enzyme Inhibitors, ed. by Urs Brodbeck, (1980), pp. 2.23–244.
47. Receptor Binding in Drug Research, ed. by Robert A. O'Brien, pp. 235–259.
48. Kandutsch, A.A., Chen, H.W., Journal of Biological Chemistry, (1973), 248, pp. 8408–8417.
49. Fimognari, G.M., Rodwell, V.W., Biochemistry, (1965) 4, pp. 2086–2090.
50. Bloxham, D.P., Biochem J., (1975), 147, pp. 531–539.
51. 3-Hydroxy-3-MethylQlutarYl Coenzvme A Reductase,ed., by John R. Sabine, CRC Series in Enzyme Biolpgy, CRC Press, Inc. Boca Raton, Florida.
52. *Design of Active-Site-Directed Irreversible Enzyme Inhibitors,* B.R. Baker, (1975), p. 9.
53. *Inhibitors of DNA and RNA Polymerases,* International Encyclopedia of Pharmacology and Therapeutics, Section 103, edited by Prem S. Sarin and Robert C. Gallo, Pergamon Press, N.Y., N.Y.
54. Mao, J.C., Robishaw, E.E., Biochemistry, (1975), 4, pp. 5475–5479.
55. Layton, D., Azzi, A., Biochemical and Biophysical Research Communications, (1974) 59, pp. 322–325.
56. Saari, W.S., et. al., J. Am. Chem. Soc., (1967), 10, pp. 1008–1014.
57. Bergstrand, H., et. al., Molecular Pharmacology, (1977), 13, pp. 38–43.
58. Fuller, R.W., et. al., Journal of Medicinal Chemistry, (1975), 18, p. 304.
59. Bricker, L.A., Levey, G.S., Journal of Biological Chemistry, (1972), 247, pp. 4914–4915.
60. Khwaja, T.A., et. al., Biochemistry, (1975), 14, pp. 4238–4244.
61. Bertelli, A., et. al., Experientia, (1976), 32, pp. 261–262.
62. *Medicinal Chemistry A Biochemical Approach,* Thomas Nogrady, (1985) Oxford University Press, N.Y., N.Y., pp. 274–285.
63. *Prostaglandin Synthetase Inhibitors: New Clinical Applications,* (1980) Alan R. Liss Inc., N.Y., N.Y., pp. 231–256.
64. The Pharmacological Basis of Therapeutics, ed. by A.G. Gilman, L. Gilman, 6th ed., (1980) MacMillan Publishing Co., N.Y., N.Y., pp 668–681.
65. Way, L., Durbin, R.P., Nature, (1969), 221, pp. 874–875.
66. Kattlove, H.E., Biochimica et. Biophysica Acta, (1974), 372, pp. 135–140.
67. *Medicinal Chemistry A Biochemical Approach,* Thomas Nogrady, (1985), Oxford University Press, N.Y., N.Y., pp 358–361.
68. Porter C.C., Watson, L.S., J. Am. Chem. Soc., (1967), 10, pp. 852–855.
69. Spurkes, T.L., Arch. Biochem. Biophys., (1954), 51, pp. 444–456.
70. Hartman, W.J., et. al., J. Biol. Chem., (1955), 216, pp. 507–529.
71. Collins, R.D., Stark, G.R., Journal of Biol. Chem. (1971), 246, pp. 6599–6605.
72. Lienhard, G.E., Science, (1973), 180, pp. 149–154.
73. Fall, R.R., West C.A., Journal of Biol. Chem., (1971), 246, pp. 6913–6928.
74. Coleman, J.E., Journal of Biol, Chem., (1968), 243, pp. 4574–4587.
75. Agarwal, R.P., et. al., Biochemical Pharmacology, (1975), 24, pp. 693–701.
76. Agarwal, R.P., et. al., Biochemical Pharmacology, (1977) 26, pp. 359–367.
77. Sheen, M.R., et. al., Mol. Pharmacol., (1968), 4, pp. 293–299.
78. *Analysis of Insecticides and Acaricides,* Gunther and Blinn, (1955), Interscience, N.Y., N.Y., pp. 401–404.
79. *The PharmacoloQical Basis of Therapeutics,* ed., by A.G. Gilman, L. Goodman, A. Gilman, 6th ed., (1980), MacMillan Publishing Co., N.Y., N. Y.
80. Berridge, M.J., Ann. Rev. Biochem., (1987), 56, pp. 159–93.
81. *Calcium Antagonists and Cardiovascular Disease,* edited by L. H. Opie, (1984), Raven Press, N. Y., pp. 165–173.
82. Johnston, G.A.R., Iversen, L.L., Journal of Neurochemistry, (1971), 18, pp. 1951–1961.
83. Chiou, C. Y., Malagodi, M. H., Br. J. Pharmac., (1975), 53, 279–285.
84. Inagaki, M., et. al., J of Biol. Chem., (1985), 260, pp. 2922–2925.
85. Inagaki, M., et. al., Biochemistry, (1984), 23, 5036.
86. Weinstock, M., Life Sciences, (1976), 19, pp. 1453–1466.
87. Hare, L.E. et. al., Journal of Medicinal Chemistry, (1974), 17, pp. 1–5.
88. Levitt, M., et. al., Biochemical Pharmacology, (1972), Vol. 16, pp. 1313–1321.
89. Nagatsu, T., et. al., Biochemical Pharmacology, (1972), Vol. 21, pp. 1945–1953.
90. Taylor, R.J., et. al., Biochemical Pharmacology, (1968), 17, pp. 1779–1788.
91. Nagatsu, T., et. al., J. Biol. Chem., (1964), 239, pp. 2910–2917.
92. Taylor, R.J., Ellenbogen, L., Life Sciences, (1967) 6, pp. 1463–1466.
93. Undenfriend, S., et. al., Biochemical
94. Weinhold, P.A., Rethy, V.B., Biochemical Pharmacology, (1969), 18, pp. 677–680.
95. Uretsky, N.J., et. al., The Journal of Pharm. and Exp. Therp., (1975), 193, pp. 73–87.
96. El Masry, M.H., et. al., Journal of Medical Chemistry., (1975), 18, pp. 16–20.
97. Counsell, R.E., et. al., Journal of Medical Chemistry, (1970), 13, pp. 1040–1042.
98. Robert, A., et. al., Life Sciences, (1974), 14, pp. 533–538.
99. Kollonitsch, J., et. al., Nature, (1978), 274, 906–908.
100. Polakoski, K.L., McRorie, R.A., Journal of Biol. Chemistry, (1973), 248, pp. 8183–8188.
101. Way, L. Durbin, R.P., Nature, (1969), 221, pp. 874–875.
102. Lippmann, w., Seethaler, K., Experientia, (1973), 29, pp. 993–995.
103. Lippmann, W., Experientia, (1973), 29, pp. 990–991.
104. Chen, F.W.K., et. al., Prostaglandins, (1977), 13, pp. 115–125.
105. Hidaka, H., Nautre, (1971), 231, pp. 54–55.
106. Hidaka, H., et al., MQl. Pharm., (1973), 9, pp. 172–177.

107. Van Der Schoot, J.B., et. al., Journal of Pharm. Exp. Therp., (1963), 141, pp. 74–78.
108. Hidaka, H., et. al., Journal of Pharm. Exp. Therp., (1974), 191, pp. 384–392.
109. Johnson, G.A., et. al., Journal of Pharm. Exp. Therp., (1969), 168, pp. 229–234.
110. Nagastu, T., et. al., Experientia, (1972), 28, pp. 779–780.
111. Lippmann, W., Lloyd, K., Biochemical Pharmacology, (1969), 18, pp. 2507–2516.
112. Diliberto, E.J., et. al., Biochemical Pharmacology, (1973), 22, pp. 2961–2972.
113. Porter, C.C., Torchiana, M.L., Biochemical Pharmacology, (1971), 20, pp. 183–191.
114. Oyama, H., et. al., Biochemical Pharmacology, (1976), 25, pp. 277–280.
115. Catignani, G.L., Neal, R.A., Life Sciences, (1975), 16, 1915–1922.
116. Hashiguchi, H., Takahashi, H., Mol. Pharm., (1977), 13, pp. 362–367.
117. Symes, A., Sourkes, T.L., Biochemical Pharmacology (1974), 23 pp. 2045–2056.
118. Tipton, K.F., Biochem. J., (1972), 128, pp. 913–919.
119. McEwen, C.M., et. al., Biochemistry, (1969), 8, pp. 3963–3972.
120. Baldessarini, R.J., Greiner, E., Biochemical Pharmacology, (1973), 22, pp. 249–256.
121. Guldberg, H.C., Marsden, C.A., Pharmacological Reviews, (1975), 27, pp. 135–206.
122. Olsen, R.W., et. al., Mol. Pharm., (1975), 11, pp. 558–565.
123. Johnson, G.A., et. al., Journal of Neurochemistry, (1976), 26, pp. 1029–1032.
124. Johnson, G.A., Iversen, L.L., Journal of Neurochemistry, (1971), 18, pp. 1939–1950.
125. Simon, J.R., Martin, D.L., Archives of Biochemistry and Biophysics, (1973), 157, pp. 348–355.
126. Springer, R.H., et. al., Journal of Med. Chem., (1967), 19, pp. 291–296.
127. Baker, B.R., Kozma, J., Journal of Med. Chemistry, (1967), 10, pp. 682–685.
128. Baker, B.R., Wood, W.F., Journal of Med. Chemistry, (1967), 10, pp. 1101–1105.
129. Spector, I., Johns, D.G., Journal of Biol. Chemistry, (1970), 245, pp. 5079–5085.
130. Baldwin, J.J., et. al., Journal of Med. Chemistry, (1975), 18, pp. 895–900.
131. Duggan, D.E., et. al., Journal of Med. Chemistry, (1975), 18, pp. 900–905.
132. Ferraccioli, G., et. al., J. Rheumatol, (1984), 11, pp. 330–332.
133. Iwata, H., et. al., Biochemical Pharm., (1969), 18, pp. 955–957.
134. Iwata, H., et. al., Biochemical Pharm., (1973), 22, pp. 1845–1854.
135. Huszti, Z., Sourkes, T.L., Journal of Pharm. Exp. Therp., (1975), 192, pp. 432–440.
136. Leinweber, F.J., Braun, G.A., Mol. Pharm., (1970), 6, pp. 146–155.
137. Lorenz, W., Werle, E., Bioch. Pharm., (1969), 17, pp. 539–549.
138. Ellenborgen, L., et. al., Biochem. Pharm., (1973), 22, pp. 939–947.
139. Ellenborgen, L., et. al., Biochem. Pharm., (1969), 18, pp. 683–685.
140. Alston, T.A., Abeles, R.H., Biochemistry, (1987), 
141. Ellenbogen, L., et. al., Biochem. Pharm., (1969), 18, pp. 683–685.
142. Lukes, J.J., Neiforth, K.A., Journal of Med. Chemistry, (1975), 18, pp. 351–354.
143. Collins, D., Journal of Biol, Chemistry, (1974), 249, pp. 136–142.
144. Kandutsch, A.A., Chen, H.W., Journal of Biol. Chemistry, (1974), 249, pp. 6057–6061.
145. Kandutsch, A.A., Chen, H.W., Journal of Biol. Chemistry, (1973), 248, pp. 8408–8417.
146. Kupiecki, F.P., Marshall, N.B., Journal of Pharm. Exp. Therp., (1968), 160, pp. 166–170.
147. Kypson, J., Hait, G., Journal of Pharm. Exp. Therp., (1976), 199, pp. 565–574.
148. Pereira, J.N., Holland, G.F., Journal. Pharm. Exp. Therp., (1967), 157, pp. 381–387.
149. Dulin, W.E., et. al., Proceedings of the Society for Experimental Biology and Medicine, (1965), 118, pp. 499–501.
150. Dulin, W.E., Gerritsen, G.C., Proceedings of the Society for Experimental Biology and Medicine, (1966), 121, pp. 777–779.
151. Waldvogel, E.R.F., et. al., Mol. Pharm., (1967), 3, pp. 429–441.
152. Lowenstein, J.M., Journal of Biol. Chemistry, (1971), 246, pp. 629–632.
153. Maragoudakis, M.E.,. Journal of Biol. Chemistry, (1971), 246, pp. 4046–4052.
154. Maragoudakis, M.E., Hankin, H., Journal of Biol. Chemistry, (1971), 246, pp. 348–358.
155. Hashimoto, T., et. al., Eur, J., Biochem., (1971), 24, pp. 128–139.
156. Maragoudakis, M.E., Biochemistry, (1970), 9, pp. 413–417.
157. Brady, R.O., Biochem. Biophys. Acta, (1963), 70, pp. 467–468.
158. Rokujo, T., et. al., Life Sciences, (1970), 9, pp. 379–385.
159. Dalton, C., et. al., Prostaglandins, (1974), 7, pp. 319–327.
160. Windmueller, H.G., Levy, R.I., Journal of Biol. Chemistry, (1967), 9, pp. 2246–2254.
161. Roheim, P.S., et. al., Biochem. Biophys. Research. Comm., (1965), 20, pp. 416–421.
162. Smith, D.A., et. al., Geriatics, (1987), 42, pp. 55–62.
163. Falcon, M.G., Jones, B.R., Journal of Gen. Virol., (1977), 36, pp. 199–202.
164. Meek, E.S., Takahashi, M., Nature, (1968), 220, p. 882.
165. De Clercq, E., Luczak, M., Life Sciences, (1975), 17, pp. 187–194.
166. Becker, Y., Pharmac. Ther., (1980), 10, pp. 119–159.
167. Asano, T., Ochiai, Y., Mol. Pharm., (1977), 13, pp. 400–406.
168. Iwai, H., Journal of Biochem., (1974), 76, pp. 419–429.
169. Lippmann, W., Experientia, (1974), 30, pp. 237–239.
170. Nikaido, T., et. al., Planta Medica, (1981), 43, pp. 18–23.
171. Vigdahl, R.L., et. al., Biochem. Biophys. Research Comm., (1971), 42, pp. 1088–1094.
172. Tateson, J.E., Trist, D.G., Life Sciences, (1976), 18, pp. 153–162.
173. Evans, D.P., Thomson, D.S., Br. J. Pharmac., (1975), 53, pp. 409–416.
174. Simmonds, H.A., et. al., Lancet, (1978), Jan. 14, pp. 60–63.
175. Trotta, P.P., et. al., Mol. Pharm., (1978), 14, pp. 199–209.

176. Deibel, M.R., et. al., Biochemical Medicine, (1981), 25, pp. 288–297.
177. Humphrey, S.M., et. al., Journal of Surgical Research, (1987), 43, pp. 187–195.
178. Beard, N.A., et. al., Br. J. Pharmac., (1975), 54, pp. 65–74.
179. Chignard, M., Vargafting, B.B., Prostaglandins, (1977), 14, pp. 222–240.
180. Panganamala, R.V., et. al., Prostaglandins, (1977), 14, pp. 261–271.
181. Kulkarni, P.S., Eakins, K.E., Prostaglandins, (1976), 12, pp. 465–469.
182. Downing, D.T., et. al., Biochem., Biophys. Research Comm., (1970), 40, pp. 218–223.
183. Gorman, R.R., et. al., Biochem. Biophys. Research Comm., (1977), 79, pp. 305–313.
184. Cushman, D.W., Cheung, H.S., Biochem. Biophys. Acta, (1976), 424, pp. 449–459.
185. Taylor, R.J., Salata, J.J., Biochemical Pharmacology, (1976), 25, pp. 2479–2484.
186. Ku, E.C., et. al., Biochemical Pharmacology, (1975), 24, pp. 641–643.
187. Burghuber, O.C., et. al., Am. Rev. Respir. Dis., (1985), 131, pp. 778–785.
188. Michelot, R.J., et. al., Mol. Pharm., (1977), 13, pp. 368–373.
189. Kessel, D., McElhinney, R.S., Biochemical Pharmacology, (1975), 24, pp. 133–137.
190. Gale, G.R., et. al., J. Med. Chem., (1970), 13, pp. 571–574.
191. The Molecular Basis of Antibiotic Action, ed. by E.F. Gale, (1981), pp. 258–401.
192. Hillcoat, B.L., et. al., J. Biol. Chem., (1967), 242, pp. 4777–4781.
193. Carlin, S., et. al., Mol. Pharm., (1974), 10, pp. 194–203.
194. Johns, D.G., et. al., Biochemical Pharmacology, (1970), 19, pp. 1528–1533.
195. Baker, B.R., et. al., J. Med. Chem., (1967), 10, pp. 1134–1138.
196. Baker, B.R., Lourens, G.J., J. Med. Chem., (1989), 1, pp. 666–672.
197. Nair, M.G., et. al., J. Med. Chem., (1974), 17, pp. 1268–1272.
198. Ferone, R., J. Biol. Chem., (1970), 245, pp. 850–854.
199. LaFon, S.W., et. al., J. Biol. Chem., (1985), 260, pp. 9660–9665.
200. Spector, T., Miller, R.L., Biochemica et. Biophysica Acta, (1976), 445, pp. 509–517.
201. *Advances in Enzymology*, ed. by Alton Meister, (1987) pp. 59-101.
202. Umezawa, H., Ann. Rev. Microbiol., (1982), 36, pp. 75–99.
203. Walsh, C.T., Ann. Rev. Biochem., (1984), 53, pp. 493–535.
204. Demain, A., Biochem. Soc. Symp., (1983), 48, pp. 117–132.
205. Suhadolnik, R.J., Progress in Nucleic Acid Research and Moleulor Biology, (1979), 22, pp. 193–291.
206. Free, C.A., et. al., Biochem. Pharm., (1971), 20, pp. 1421–1428.
207. Enzymes Dixon M. and Webb, F.C., Academic Press Inc., N.Y., N.Y. (1964), p. 407.
208. Kondo, T., et. al., Diabetes Care, (1982), vol. 5, Number 3, pp. 218–221.
209. Higgins, I.J., Hill, H.A.O., Plotkin, E.V., Eur. Pat. Appl. EP78,636.
210. Miller, L.L., J. Electroanal. Chem., (1981), 117, pp. 267–281.
211. Mills, R.L., U.S. Patent Appl. 784,243.
212. Gros, P., et. al., Cell, (1986), 47, pp. 371–380.
213. Sanchez-Pescador, R., et. al., Science, (1985), 277, pp. 484–492.
214. *The Enzymes,* ed. by Paul D. Boyer, (1975), 3rd edition, Vol. XII, Part B, Academic Press, N.Y., N.Y.
215. De Clercq, E., and Balzarini, J., Antiviral Research, Suppl. I, (1985), pp. 89–94.

What is claimed is:

1. A chemical compound having the formula A-B-C, where

A is a chemiluminescent moiety which reacts with peroxides and oxygen free radicals and is capable of transferring energy from its own excited state to B;

B is a photochromic moiety covalently bonded to A which receives energy from A to achieve an excited state, wherein the emission spectrum of A overlaps the absorption-release reaction spectrum of B in the wavelength range of 250 nm to 420 nm; and C is a biologically active agent covalently bonded to B, wherein relaxation of the excited state of B causes heterolytic cleavage of the covalent bond between B and C, thereby releasing C from B.

2. The chemical compound of claim 1, wherein said chemiluminescent moiety is a lophine, an acridinium ester, an acridan, a tetraphenylpyrrole, a phthalhydrazide, an acyloin, a biacridinium salt, a vinylcarbonyl, a vinylnitrile, an acylperoxide, an indole, a tetracarbazole, an active oxalate, 2,6-diaminopyrene, a dioxetan, a dioxetanone, an imidazole, a sulfonyloxamide, a tetrakis (dialkylamino) ethylene, 2,5,7,8-tetraoxabicyclo-[4.2.0.]octane, a lucigenin, a diphenyl peroxide, or a dioxene.

3. The chemical compound of claim 1, wherein said photochromic moiety comprises a cationic dye which demonstrates photochromic behavior with electromagnetic radiation and bleaching agents.

4. The chemical compound of claim 3, wherein said cationic dye is a di or triarylmethane dye, a triarylmethane lactone or a cyclic ether dye, a cationic indole, a pyronine, a phthalein, an oxazine, a thiazine, an acridine, a phenazine, an anthocyanidin, a cationic polymethine dye, an azo or a diazopolymethine, a styryl, a cyanine, a hemicyanine, or a dialkylaminopolyene.

5. A chemical compound having the formula A-B-C, where

A is a chemiluminescent moiety which undergoes an oxidation reduction reaction and is capable of transferring energy from its own excited state to B;

B is a photochromic moiety covalently bonded to A which receives energy from A to achieve an excited state, wherein the emission spectrum of A overlaps the absorption-release reaction spectrum of B in the wavelength range of 250 nm to 420 rnm; and C is a biologically active agent covalently bonded to B, wherein relaxation of the excited state of B causes heterolytic cleavage of the covalent bond between B and C, thereby releasing C from B.

6. The chemical compound of claim 5, wherein said chemiluminescent moiety is a cation radical or a ruthenium chelate.

7. The chemical compound of claim 5, wherein said chemiluminescent moiety is selected from the group consisting of tris-2,2'-bipyridinedichlororuthenium (11) and 2 6-diaminopyrene.

8. A chemical compound having the formula A-B-C, where

A is a phthalhydrazide capable of transferring energy from its own excited state to B;

B is a polymethine dye covalently bonded to A which receives energy from A to achieve an excited state, wherein the emission spectrum of A overlaps the absorption-release reaction spectrum of B in the wavelength range of 250 nm to 420 nm; and C is a biologically active agent covalently bonded to B, wherein relaxation of the excited state of B causes heterolytic cleavage of the covalent bond between B and C, thereby releasing C from B.

9. The chemical compound of claim 8, wherein C is selected from the group consisting of 3,5-diiodo-4-hydroxybenzoic acid, y-aminobutyric acid, gabaculine, N-5'-phosphopyridoxyl-4-aminobutyric acid, baclofen, trans-4-aminocrotonic acid, compactin, [3-hydrox-3-methylglutarate]3-hydroxy-3-methylglutarate, p-glycolohydroxamate, N-(phosphonoacetyl)-L-aspartate, phosphonoacetate, mimosine, 2-mercaptoethylamine, NSD 1055, polvoxin D D,L-hydrazino-α-methyldopa, and phosphonoformate.

10. The chemical compound of claim 1, wherein C is a drug molecule which effects a therapeutic functional change by a mechanism selected from the group consisting of receptor mediated mechanisms and nonreceptor mediated mechanisms.

11. The chemical compound of claim 1, wherein C is selected from the group consisting of antilipidemic drugs, anticholesterol drugs, anticoagulants, antihypertensive drugs, cardiac inotropic drugs, antineoplastic drugs, antidepressant drugs, agents for the treatment of asthma and hypersensitivity reactions, diuretics, antifungal agents, antibacterial drugs, anxiolytic agents, sedatives, muscle relaxants, anticonvulsants, agents for the treatment of ischemic heart disease, agents which activate the effects of secondary messengers, agents to block spinal reflexes, and antiviral agents.

12. The chemical compound of claim 1, wherein C is an antihypertensive agent.

13. The chemical compound of claim 12, wherein C is selected from the group consisting of 3,5-diiodo-4-hydroxybenzoic acid, mimosine, D,L-hydrazino-(I-methyldopa, and 2-mercaptoethylamine.

14. The chemical compound of claim 1, wherein C is an antiviral agent.

15. The chemical compound of claim 14, wherein C is selected from the group consisting of phosphonoacetate and phosphonoformate.

16. The chemical compound of claim 1, wherein C is an anticholesterol agent.

17. The chemical compound of claim 16, wherein C is selected from the group consisting of compactin and 3-hydroxy-3-methylglutarate.

18. The chemical compound of claim 1, wherein C is an anticonvulsant agent.

19. The chemical compound of claim 18, wherein C is selected from the group consisting of gabaculine, N-5'-phosphopyridoxyl-4-aminobutyric acid, baclofen, trans-4-aminocrotonic acid, and 7-aminobutyric acid.

20. The chemical compound of claim 1, wherein C is an antibacterial or antifungal agent.

21. The chemical compound of claim 20, wherein C is selected from the group consisting of p-glycolohydroxamate and polyoxin D.

22. The chemical compound of claim 1, wherein C is an antineoplastic agent.

23. The chemical compound of claim 22, wherein C is N-(phosphonoacetyl)-L-aspartate.

24. The chemical compound of claim 1, wherein the chemical compound is covalently bound to a biocompatible polymer to which an enzyme is immobilized.

25. The chemical compound of claim 24, wherein C is insulin and the enzyme is glucose oxidase.

26. The chemical compound of claim 24, wherein C is tissue plasminogen activator and the enzyme is xanthine oxidase.

* * * * *

UNITED STATES PATENT AND TRADEMARK OFFICE
CERTIFICATE OF CORRECTION

PATENT NO. : 5,773,592
DATED : June 30, 1998
INVENTOR(S) : Randell Lee Mills

It is certified that error appears in the above-indentified patent and that said Letters Patent is hereby corrected as shown below:

At claim 9, line 5-6, delete "[3-hydrox-3-methylglutarate]".

At claim 9, line 9, after "1055", delete "." and insert --,--.

At claim 13, line 3, delete "(I" and insert --α--.

At claim 19, line 4, delete "7" and insert --γ--.

Signed and Sealed this

Seventeenth Day of November, 1998

*Attest:*

BRUCE LEHMAN

*Attesting Officer*     Commissioner of Patents and Trademarks